US012122822B2

United States Patent
Kim et al.

(10) Patent No.: US 12,122,822 B2
(45) Date of Patent: *Oct. 22, 2024

(54) ANTI-BAG2 ANTIBODY AND METHODS OF TREATING CANCER

(71) Applicant: MEDPACTO, INC., Seoul (KR)

(72) Inventors: Seong Jin Kim, Seoul (KR); Dong Woo Kang, Seoul (KR)

(73) Assignee: MEDPACTO, INC., Seoul (KR)

( * ) Notice: Subject to any disclaimer, the term of this patent is extended or adjusted under 35 U.S.C. 154(b) by 940 days.

This patent is subject to a terminal disclaimer.

(21) Appl. No.: 16/758,930

(22) PCT Filed: Feb. 12, 2020

(86) PCT No.: PCT/IB2020/051136
§ 371 (c)(1),
(2) Date: Apr. 24, 2020

(87) PCT Pub. No.: WO2020/165794
PCT Pub. Date: Aug. 20, 2020

(65) Prior Publication Data
US 2023/0183324 A1    Jun. 15, 2023

(30) Foreign Application Priority Data

Feb. 12, 2019  (KR) ........................ 10-2019-0016347
Feb. 12, 2019  (KR) ........................ 10-2019-0016359

(51) Int. Cl.
| C07K 16/18 | (2006.01) |
| A61P 35/00 | (2006.01) |
| C12N 15/63 | (2006.01) |
| G01N 33/574 | (2006.01) |
| G01N 33/68 | (2006.01) |

(52) U.S. Cl.
CPC .............. *C07K 16/18* (2013.01); *A61P 35/00* (2018.01); *C12N 15/63* (2013.01); *G01N 33/57484* (2013.01); *G01N 33/6854* (2013.01); *C07K 2317/24* (2013.01); *C07K 2317/565* (2013.01); *G01N 2333/4703* (2013.01)

(58) Field of Classification Search
CPC .................... C07K 16/18; C07K 2317/76
See application file for complete search history.

(56) References Cited

U.S. PATENT DOCUMENTS

| 2008/0292546 A1 | 11/2008 | Clarke et al. |
| 2009/0275608 A1 | 11/2009 | Ossovskaya et al. |
| 2010/0204055 A1* | 8/2010 | Bonner-Ferraby ... G01N 33/564 506/18 |
| 2010/0255470 A1 | 10/2010 | Bankaitis-Davis et al. |

FOREIGN PATENT DOCUMENTS

| KR | 10-2018-0101052 A | 9/2018 |
| KR | 20180101052 A | 9/2018 |
| RU | 2016107874 A | 9/2017 |
| WO | 2019083262 A1 | 5/2019 |

OTHER PUBLICATIONS

Qin et. al. (Cellular & Molecular Biology Letters 21(18):1-11 (2016) (Year: 2016).*
Almagro et. al., Front. Immunol. 2018; 8:1751 (Year: 2018).*
Rudikoff et al., Proc. Nat'l Acad. Sci. USA, 79:1979-83 (1982) (Year: 1982).*
Brown et al., J. Immunol., 156(9):3285-91 (1996) (Year: 1996).*
Rabia et. al. (Biochemical Engineering Journal 137:365-374. (2018)) (Year: 2018).*
Marvin et. al., Biochemistry, 42(23):7077-7083 (2003) (Year: 2003).*
Ho et. al. (Methods Mol Biol. 525:293-308 (2009)) (Year: 2009).*
Kuo et. al. (Plos One 13(2): 1-22. (2018)) (Year: 2018).*
Notification of Transmittal of the International Search Report and the Written Opinion for corresponding PCT Application No. PCT/IB2020/051136, mailed May 25, 2020 (15 pages).
Hong Ying-Cai et al., BAG2 overexpression correlates with growth and poor prognosis of esophageal squamous cell carcinoma, Open Life Sci 2018, Vo. 13, p. 582-588, cm. c.584 "2.7 Western blotting analysis".
Ivan Roitt et al., "Immunology", fifth edition, Mosby 2000, 4 pages.
Yang, Kyung-Min, "Co-chaperone BAG2 determines the pro-oncogenic role of cathepsin B in triple-negative breast cancer cells", Cell Reports, (Dec. 5, 2017), vol. 21, No. 1010, doi:10.1016/j.celrep.2017.11.026, ISSN 2211-1247, pp. 2952-2964, XP055595394.
Yoon C I et al: "Prognostic impact of BAG2 expression on breast cancer is highlighted in patients with large tumor or lymph node metastasis", European Journal of Cancer, Elsevier, Amsterdam NL, vol. 92, Mar. 28, 2018 (Mar. 28, 2018), XP085366970, ISSN: 0959-8049, DOI: 10.1016/S0959-8049(18)30357-5.

* cited by examiner

*Primary Examiner* — Jessica H Roark
*Assistant Examiner* — Francesca Edgingtongiordan
(74) *Attorney, Agent, or Firm* — FisherBroyles, LLP; Joseph Hyosuk Kim

(57) ABSTRACT

The present application discloses an antibody or antigen-binding fragment thereof that binds specifically to a BAG2 polypeptide or fragment thereof, and a method of treating cancer thereof.

27 Claims, 27 Drawing Sheets

Specification includes a Sequence Listing.

ANTI-BAG2 ANTIBODY AND METHODS OF TREATING CANCER

This application is the U.S. national phase of International Application No. PCT/IB2020/051136 filed Feb. 12, 2020 which designated the U.S. and claims priority to Korean Patent Application Nos. 10-2019-0016347 filed Feb. 12, 2019, and 10-2019-0016359 filed Feb. 12, 2019, the entire contents of each of which are hereby incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 6987_0310_Substitute_Sequence_Listing.txt. The text file is 51,663 bytes, was created on Feb. 17, 2021, and is being submitted electronically via EFS-Web.

BACKGROUND OF THE INVENTION

1. Field of the Invention

The present disclosure relates to an antibody or antigen-binding fragment thereof that specifically binds to a BAG2 polypeptide or fragment thereof. The present application also relates to an anti-cancer therapeutic agent using the inventive composition.

2. General Background and State of the Art

The co-chaperone Bcl-2-associated athanogene (BAG) protein family mediates a variety of physiological processes, including intracellular protein folding, stress response, neuronal differentiation, apoptosis, and cell proliferation, and functionally binds to various cooperative proteins. BAG2, one of the members of the BAG domain family with anti-apoptosis activity, is a negative regulator of the C-terminus of Hsc70-interacting protein (CHIP), which is a chaperone-associated ubiquitin ligase. The main role of BAG2 in the regulation of proteins through inhibiting CHIP activity is associated with neurodegenerative diseases and autosomal recessive disorders through the stabilization of chaperone related proteins such as PINK1 and CFTR. It is reported that BAG2 has a pro-apoptotic activity in such a way that expression of BAG2 increases proteasome inhibitor-induced apoptosis, and BAG2 knockdown partially inhibits apoptosis when thyroid carcinoma cells are exposed to proteasome inhibitor MG132. Apart from the formation of the BAG2-Hsp70 complex, the BAG protein functionally interacts with a variety of binding partners and regulates various cellular processes such as stress signaling, cell division, apoptosis and cell differentiation. It is also reported that, in various mutant K-Ras-induced tumors, overexpression of BAG2 promotes the stabilization of STK33 protein, which is a potent tumor gene, and thus promotes the development of tumor. In addition, it has been suggested that the expression and location of BAG2 protein may vary according to the histopathological and molecular genetic pathology of cancer cells during the progression or metastasis of breast cancer. It was found that BAG2 protein is secreted out of the cell by interacting with cathepsin B, which is the protein degrading enzyme, during tumorigenesis, and it is confirmed that the loss of BAG2 protein completely inhibits cancer formation and metastasis to the lung in animal models of breast cancer. As a result, the development of BAG2 inhibitors will contribute to the treatment and survival of cancer patients.

Despite these findings, however, the role of BAG2 in the progression and metastasis of cancer is not clearly known. In addition, no specific studies have been conducted on BAG2 monoclonal antibodies. Accordingly, there is a need to develop an antibody or antigen-binding fragment thereof that specifically binds to a BAG2 polypeptide or fragment thereof.

SUMMARY OF THE INVENTION

These and other objects of the invention will be more fully understood from the following description of the invention, the referenced drawings attached hereto and the claims appended hereto.

An aspect provides an antibody or antigen-binding fragment thereof that specifically binds to a BAG2 polypeptide or fragment thereof.

Another aspect provides a polynucleotide encoding the antibody or antigen-binding fragment thereof.

Another aspect provides a host cell including the polynucleotide.

Another aspect provides a method of producing the antibody or antigen-binding fragment thereof.

Additional aspects will be set forth in part in the description which follows and, in part, will be apparent from the description, or may be learned by practice of the presented embodiments of the disclosure.

An aspect provides an antibody or antigen-binding fragment thereof that specifically binds to a BAG2 polypeptide or fragment thereof.

BAG2 polypeptides may be derived from a mammal. The mammal may be a human (*Homo sapiens*), a mouse (*Mus musculus*), a monkey, cow, or a horse. BAG2 may include the amino acid sequence of SEQ ID NO: 69. The amino acid sequence of SEQ ID NO: 69 is a sequence corresponding to NCBI Reference SEQ ID NO: NM_004282.4. The BAG2 protein includes variants which have biologically equivalent activity to the amino acid sequence of SEQ ID NO: 69 although their amino acid sequences may not match the amino acid sequence of SEQ ID NO: 69. The BAG2 polypeptide may include an amino acid sequence having at least 60%, for example, at least 70%, at least 80%, at least 90%, at least 95%, at least 99%, or 100% sequence identity with the sequence of SEQ ID NO: 69. The BAG2 protein may be a polypeptide having the same sequence of SEQ ID NO: 69 except for at least one amino acid residue, at least two amino acid residues, at least three amino acid residues, at least four amino acid residues, at least five amino acid residues, at least six amino acid residues, or at least seven amino acid residue residues. In the present specification, the 'polypeptide' may be used interchangeably with the 'protein'.

The antibody refers to a specific immunoglobulin directed against an antigenic site. The antibody refers to a polypeptide or a combination of polypeptides that specifically binds to a BAG2 polypeptide or fragment thereof. The antibody may include polyclonal antibodies, monoclonal antibodies, or recombinant antibodies, such as ScFv fragments, diabodies, single chain antibodies, and the like, and include all immunoglobulin antibodies. The antibody may include a full form of antibody having two full-length light chains and two full-length heavy chains and may also include functional fragments of antibody molecules thereof that retain antigen-binding function due to the inclusion of having specific antigen-binding sites, that is, binding domains despite the absence of the structure of a full form intact antibody with two light chains and two heavy chains.

The antigen-binding fragment is a fragment of the entire structure of the immunoglobulin, and refers to a portion of the polypeptide including a portion to which an antigen is able to bind. For example, the antigen-binding fragment thereof may be scFv, (scFv)2, Fv, Fab, Fab', Fv F(ab')2, or a combination thereof.

There are five kinds of heavy chains γ, δ, α, μ and ε and a heavy chain may determine the type of antibody. α and γ each include 450 amino acids and μ and ε each include 550 amino acids. The heavy chain has two regions, that is, a variable region and a constant region.

There are two kinds of light chains kappa and lambda and may include about 211 amino acids to about 217 amino acids. A light chain may have a constant region and a variable region.

The antibody or antigen-binding fragment thereof may include a heavy chain variable region including a complementarity determining region (VH-CDR)1 consisting of the amino acid sequence of SEQ ID NO: 33, a VH-CDR2 consisting of the amino acid sequence of SEQ ID NO: 39, and a VH-CDR3 consisting of the amino acid sequence of SEQ ID NO: 45, and a light chain variable region including a complementarity determining region (VL-CDR)1 consisting of the amino acid sequence of SEQ ID NO: 51, a VL-CDR2 consisting of the amino acid sequence of SEQ ID NO: 57, and a VL-CDR3 consisting of the amino acid sequence of SEQ ID NO: 63; a heavy chain variable region including a VH-CDR1 consisting of the amino acid sequence of SEQ ID NO: 34, a VH-CDR2 consisting of the amino acid sequence of SEQ ID NO: 40, and a VH-CDR3 consisting of amino acid sequence of SEQ ID NO: 46, and a light chain variable region including a VL-CDR1 consisting of the amino acid sequence of SEQ ID NO: 52, a VL-CDR2 consisting of the amino acid sequence of SEQ ID NO: 58, and a VL-CDR3 consisting of the amino acid sequence of SEQ ID NO: 64; a heavy chain variable region including a VH-CDR1 consisting of the amino acid sequence of SEQ ID NO: 35, a VH-CDR2 consisting of the amino acid sequence of SEQ ID NO: 41, and a VH-CDR3 consisting of the amino acid sequence of SEQ ID NO: 47, and a light chain variable region including a VL-CDR1 consisting of the amino acid sequence of SEQ ID NO: 53, a VL-CDR2 consisting of the amino acid sequence of SEQ ID NO: 59, and a VL-CDR3 consisting of the amino acid sequence of SEQ ID NO: 65; a heavy chain variable region including a VH-CDR1 consisting of the amino acid sequence of SEQ ID NO: 36, a VH-CDR2 consisting of the amino acid sequence of SEQ ID NO: 42, and a VH-CDR3 consisting of the amino acid sequence of SEQ ID NO: 48, and a light chain variable region including a VL-CDR1 consisting of the amino acid sequence of SEQ ID NO: 54, a VL-CDR2 consisting of the amino acid sequence of SEQ ID NO: 60, and a VL-CDR3 consisting of amino acid sequence of SEQ ID NO: 66; a heavy chain variable region including a VH-CDR1 consisting of the amino acid sequence of SEQ ID NO: 37, a VH-CDR2 consisting of the amino acid sequence of SEQ ID NO: 43, and a VH-CDR3 consisting of the amino acid sequence of SEQ ID NO: 49, and a light chain variable region including a VL-CDR1 consisting of the amino acid sequence of SEQ ID NO: 55, a VL-CDR2 consisting of the amino acid sequence of SEQ ID NO: 61, and a VL-CDR3 consisting of the amino acid sequence of SEQ ID NO: 67; a heavy chain variable region including a VH-CDR1 consisting of the amino acid sequence of SEQ ID NO: 38, a VH-CDR2 consisting of the amino acid sequence of SEQ ID NO: 44, and a VH-CDR3 consisting of the amino acid sequence of SEQ ID NO: 50, and a light chain variable region including a VL-CDR1 consisting of the amino acid sequence of SEQ ID NO: 56, a VL-CDR2 consisting of the amino acid sequence of SEQ ID NO: 62, and a VL-CDR3 consisting of the amino acid sequence of SEQ ID NO: 68; or a combination thereof.

The 6th and 7th Xaa in SEQ ID NO: 39 may be glycine (Gly) or alanine (Ala). The 2nd Xaa in SEQ ID NO: 35 may be tyrosine (Tyr) or histidine (His). The 8th Xaa in SEQ ID NO: 41 may be serine (Ser) or threonine (Thr). The 12th Xaa in SEQ ID NO: 47 may be tyrosine (Tyr) or histidine (His). The 3rd Xaa in SEQ ID NO: 53 may be methionine (Met) or isoleucine (lie). The 2nd Xaa in SEQ ID NO: 59 may be Ala or Ser.

The antibody or antigen-binding fragment thereof may include a heavy chain variable region including an amino acid sequence of any one selected from SEQ ID NOS: 21 to 26; a light chain variable region including an amino acid sequence of any one selected from SEQ ID NOS: 27 to 32; or the heavy chain variable region and the light chain variable region.

The antibody or antigen-binding fragment thereof may include a heavy chain variable region of SEQ ID NO: 21 and a light chain variable region of SEQ ID NO: 27; a heavy chain variable region of SEQ ID NO: 22 and a light chain variable region of SEQ ID NO: 28; a heavy chain variable region of SEQ ID NO: 23 and a light chain variable region of SEQ ID NO: 29; a heavy chain variable region of SEQ ID NO: 24 and a light chain variable region of SEQ ID NO: 30; a heavy chain variable region of SEQ ID NO: 25 and a light chain variable region of SEQ ID NO: 31; or a heavy chain variable region of SEQ ID NO: 26 and a light chain variable region of SEQ ID NO: 32, or a combination thereof.

The 56th Xaa and 57th Xaa in SEQ ID NO: 21 may each be Gly or Ala. In SEQ ID NO: 23, the 1st Xaa may be glutamine (Gin Gln) or glutamate (Glu), the 7th Xaa may be Ser or proline (Pro), the 12th Xaa may be valine (Val) or alanine(Ala), the 27th Xaa may be Tyr or His, the 58th Xaa may be Ser or Thr, the 61st Xaa may be asparagine (Asn) or Ser, the 74th Xaa may be arginine (Arg) or lysine (Lys), the 83rd Xaa may be phenylalanine (Phe) or leucine (Leu), the 92nd Xaa may be Gly or Ala, and the 108th Xaa may be His or Tyr. The 53rd Xaa in SEQ ID NO: 27 may be Ile or Phe. In SEQ ID NO: 29, the 29th Xaa may be Met or Ile, the 51st Xaa may be Ala or Ser, and the 79th Xaa may be Glu or aspartic acid (Asp), and the 106th Xaa may be Met or Ile.

The antibody or antigen-binding fragments thereof include a plurality of antibodies or antigen-binding fragments thereof, and may be a combination of antibodies selected from one of No. 1 sets and one of No. 2 sets; one of No. 1 sets and one of No. 3 sets; and one of No. 2 sets and one of No. 3 sets. The No. 1 set may be an antibody or antigen-binding fragment thereof, binding to a middle region of a BAG2 protein, including VH of SEQ ID NO: 21 and VL of SEQ ID NO: 27, and VH of SEQ ID NO: 22 and VL of SEQ ID NO: 28. The No. 2 set may be an antibody or antigen-binding fragment thereof, binding to an N-terminus of a BAG2 protein, including VH of SEQ ID NO: 23 and VL of SEQ ID NO: 29, and VH of SEQ ID NO: 24 and VL of SEQ ID NO: 30. The No. 3 set may be an antibody or antigen-binding fragment thereof, binding to a C-terminus of a BAG2 protein, including VH of SEQ ID NO: 25 and VL of SEQ ID NO: 31, and VH of SEQ ID NO: 26 and VL of SEQ ID NO: 32.

The antibody or antigen-binding fragments thereof may be a monoclonal antibody.

The antibody or antigen-binding fragments thereof may be marked with a detectable label or a label capable of emitting a detectable signal. The label refers to a detectable compound or composition conjugated directly or indirectly to an antibody to produce a labeled antibody or antigen-binding fragment thereof. The label may be detectable by itself and catalyze the chemical modification of the detectable substrate compound or composition.

The label may be an immunofluorescent label, a chemiluminescent label, a phosphorescent label, a radiolabel, an epitope tag, avidin/biotin, colloidal gold particles, colored particles, magnetic particles, chromophore labels, an ECL label, an enzyme, or the like.

The antibody or antigen-binding fragment thereof may be produced by a hybridoma cell selected from hybridoma cells deposited with accession numbers KCTC 137378P, KCTC 137388P, KCTC 137398P, KCTC 137408P, KCTC 137418P, KCTC 137428P, KCTC 137438P, KCTC 137448P, KCTC 137458P and KCTC 137468P.

The hybridoma cell refers to a hybrid cell having a tumorigenicity by artificial fusion of two kinds of cells, and in general, may be used to continuously produce antibodies by fusing B cells and plasmacytoma cells isolated from an immunized subject. The hybridoma cell may also be referred to as a hybrid cell or a fusion cell herein.

The inventors identified an anti-BAG2 antibody including VH of SEQ ID NO: 21 and VL (2A11, 4C2, 8C4) of SEQ ID NO: 27; VH of SEQ ID NO: 22 and VL (3B5) of SEQ ID NO: 28; VH of SEQ ID NO: 23 and VL (9B3, 9B12, 3B10) of SEQ ID NO: 29; VH of SEQ ID NO: 24 and VL (10H7) of SEQ ID NO: 30; VH of SEQ ID NO: 25 and VL (3G8) of SEQ ID NO: 31; and VH of SEQ ID NO: 26 and VL (3F12) of SEQ ID NO: 32, and a hybridoma cell producing the same. It was confirmed that the identified anti-BAG2 antibody showed an antigen-antibody reaction in breast cancer cells.

Another aspect provides a polynucleotide including a polynucleotide encoding the antibody or antigen-binding fragment thereof.

The polynucleotide may be any one nucleotide sequence selected from the group consisting of SEQ ID NOS: 1 to 10 encoding a heavy chain variable region and any one nucleotide sequence selected from the group consisting of SEQ ID NOs: 11 to 20 encoding a light chain variable region.

The polynucleotide may be a vector. The vector may be obtained by replicating and/or expressing the polynucleotide in a cell. The cell may be an eukaryotic cell or a prokaryotic cell. The eukaryotic cells may be mammalian cells, plant cells, yeast cells, or insect cells. The mammal may be human, monkey, rabbit, rat, hamster or mouse. The prokaryotic cell may be a bacterial cell. The bacterium may be *E. coli*. The vector may be an expression vector. In the expression vector, the polynucleotide is operably linked to an appropriate regulatory region so that the polynucleotide is expressed in a host cell. The regulatory region may be a promoter, an enhancer, or a terminator. The vector may also include a selection marker. The vector may be a phage, plasmid, cosmid, mini-chromosome, virus, or retroviral vector. The vector may include a polynucleotide encoding a heavy chain variable region or a light chain variable region of the antibody, or may include both the polynucleotide encoding a heavy chain variable region and the polynucleotide encoding a light chain variable region.

The polynucleotide may be conjugated with a detectable label or a label capable of emitting a detectable signal. The label may be a fluorescent dye, a phosphorescent dye, a radioisotope, a chromophore, a quantum dot, a quencher, magnetic bead nanoparticles, gold nanoparticles, nanophosphors, silicon nanoparticles, semiconductor fine particles having light-emitting properties, and the like. For example, the fluorescent dye may be cyanine (cyanine 2), amidomethyl coumarin, fluorosane, indo carbocyanine (cyanine 3), cyanine 3.5, tetramethyl rhodamine, rhodamine red, texas red, indian carbocyanine (cyanine 5), cyanine 5.5, cyanine 7, oyster and the like. For example, the semiconductor fine particles may be cadmium selenium (CdSe), cadmium tellurium (CdTe), indium gallium phosphorus (InGaP), silver indium zinc sulfide (AgInZnS), or the like. The conjugation method with the label may be a method of binding a labeling substance to polynucleotide 3' terminus, a method of binding a labeling substance to 5' terminus, or a method of including a nucleotide, to which the labeling substance is bound, in the polynucleotide. The conjugating of a label to 3' terminus or 5' terminus may be performed by an enzyme reaction, and the enzyme may be T4 RNA ligase, terminus transferase, polyA polymerase, or the like. The label may be detected by fluorescence microscope, scanning electron microscope, transmission electron microscope, computed tomography, magnetic resonance imaging, or the like.

Another aspect provides a host cell including the polynucleotide.

The polynucleotide is the same as described above.

The host cell may be a bacterial cell, a yeast cell, a fungal cell, an insect cell, an animal cell or a plant cell, each containing the polynucleotide. The bacterial cells may be *Escherichia coli* (*E. coli*), *Streptomyces*, or *Salmonella typhimurium*. The yeast cells may be *Pichia pastoris*. The insect cells may be *Drosophila*, or *Spodofterra* Sf9 cells. The animal cells may be chinese hamster ovary cells (CHO), mouse myeloma (SP2/0), human lymphoblastoid, COS, mouse myeloma (NSO), 293T, bow melanoma cells, HT-1080, baby hamster kidney cells (BHK), human embryonic kidney cells (HEK), or PERC.6 (human retinal cells).

The polynucleotide may be introduced into the host cell. The introduction refers to a method of delivering a vector containing a polynucleotide encoding the antibody to a host cell. Such introductions may be carried out by various methods known in the art, including calcium phosphate-DNA coprecipitation, DEAE-dextran-mediated transfection, polybrene-mediated transfection, electroshock, microinjection, liposome fusion, lipofectamine and protoplast fusion. In addition, transduction refers to the delivery of a target product into cells using viral particles by infection. In addition, the vector may be introduced into the host cell by gene bombardment or the like. The introduction may also be referred to as transformation.

Another aspect provides a method of producing the antibody or antigen-binding fragment thereof.

The method may include culturing a host cell; and separating an antibody or antigen-binding fragment thereof from the obtained culture.

The host cell is the same as described above.

The culturing may be performed according to suitable media and culturing conditions known in the art. Those skilled in the art may easily control the medium and culture conditions according to the microorganism selected. The culture method may include, for example, batch, continuous and fed-batch culture.

The medium may include various carbon sources, nitrogen sources, and trace element components.

The carbon source may be, for example, carbohydrates such as glucose, sucrose, lactose, fructose, maltose, starch, or cellulose; fats such as soybean oil, sunflower oil, castor oil, or coconut oil; fatty acid glycerol such as palmitic acid, stearic acid, and linoleic acid; alcohols such as ethanol; organic acids such as acetic acid; or a combination thereof. The nitrogen source may include, for example, inorganic nitrogen sources, such as peptone, yeast extract, meat extract, malt extract, corn steep liquor (CSL), and soybean wheat, organic nitrogen sources, such as urea, ammonium sulfate, ammonium chloride, ammonium phosphate, ammonium carbonate and ammonium nitrate, or combinations thereof. The medium, as a source of phosphorus, may include, for example, potassium dihydrogen phosphate, dipotassium hydrogen phosphate, and the corresponding sodium-containing salts, or metal salts such as magnesium antioxidant or iron antioxidant. In addition, amino acids, vitamins, appropriate precursors, and the like may be included in the medium. The medium or individual components may be added batchwise or continuously to the culture.

In addition, during the time period in which the host cells are cultured, compounds such as ammonium hydroxide, potassium hydroxide, ammonia, phosphoric acid and sulfuric acid may be added to the microbial culture in a suitable manner to adjust the pH of the culture. In addition, during culturing of host cells, antifoaming agents such as fatty acid polyglycol esters may be used to suppress the formation of bubbles.

The cells may be cultured in aerobic, micro-aerophilic, or anaerobic conditions. The micro-aerophilic condition refers to culture conditions in which oxygen at a level lower than the level of oxygen in the atmosphere is dissolved into the medium. The low level of oxygen may be, for example, about 0.1% to about 10%, about 1% to about 9%, about 2% to about 8%, about 3% to about 7%, or about 4% to about 6%. In addition, the micro-aerophilic conditions may include a condition in which the concentration of dissolved oxygen in the medium is in a range of about 0.9 ppm to about 3.6 ppm. The culture temperature may be, for example, about 20° C. to about 45° C. or about 25° C. to about 40° C. The incubation may be continued until the desired amount of antibody or antigen-binding fragments thereof reaches a target level.

The separating may be performed by a method known in the art for the separation of an antibody. The separating may include performing one or more process selected from centrifugation, filtration, extraction, spraying, drying, evaporation, precipitation, crystallization, electrophoresis, fractional dissolution, and chromatography.

The method may further include labeling the separated antibody or antigen-binding fragment thereof. The label may be an immunofluorescent label, a chemiluminescent label, a phosphorescent label, a radiolabel, an epitope tag, avidin/biotin, colloidal gold particles, colored particles, magnetic particles, chromophore labels, an ECL label, an enzyme, or the like.

In one aspect, the present invention is directed to a method for treating cancer that is either primary or metastasized cancer in an individual comprising administering to the individual in need thereof an anti-BAG2 or antigen-binding fragment thereof as discussed above. The method may comprise co-administering or sequentially administering an existing therapeutic agent. The existing therapy may be cancer immunotherapeutic agent, which may include an inhibitor to immune checkpoint molecule, such as PD-1, PD-L1, or CTLA4. The immunotherapeutic agent may be granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), 4-1BB ligand, GITRL, OX-40L, anti-CD3 antibody, anti-CD27 antibody, anti-CTLA4 antibody, anti-PD-1 antibody, anti-PD-L1 antibody, anti-GITR antibody, anti-OX-40 antibody, anti-4-1BB antibody, anti-LAG-3 antibody, and anti-TIM-3 antibody. The cancer may be breast cancer, colorectal cancer, head and neck cancer, colon cancer, skin cancer, pancreatic cancer, lung cancer, gastric cancer, prostate cancer, bladder cancer, urethral cancer, liver cancer, kidney cancer, clear cell sarcoma, melanoma, cerebrospinal tumor, brain cancer, thymus, mesothelioma, esophageal cancer, bile duct cancer, testicular cancer, germ cell tumor, thyroid cancer, parathyroid cancer, cervical cancer, ovarian cancer, endometrial cancer, lymphoma, myelodysplastic syndromes (MOS), myelofibrosis, acute leukemia, chronic leukemia, multiple myeloma, Hodgkin's disease, endocrine cancer, and sarcoma.

BRIEF DESCRIPTION OF THE DRAWINGS

The patent or application file contains at least one drawing executed in color. Copies of this patent or patent application publication with color drawings will be provided by the Office upon request and payment of the necessary fee.

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Definitions

Figure 1:
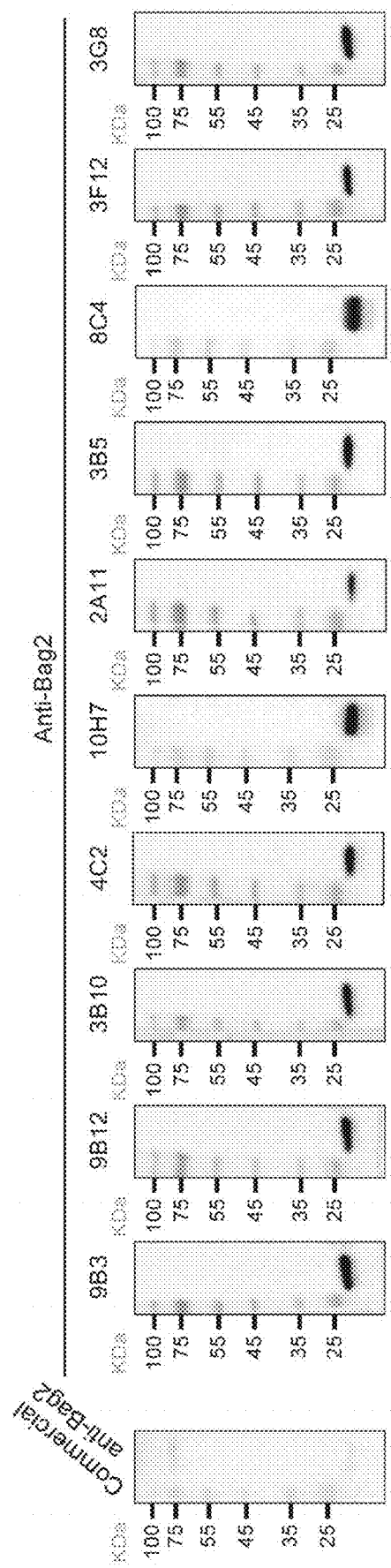
FIG. 1 shows the results of Western blotting of anti-BAG2 antibodies produced from 10 mouse hybridoma cells.

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents include simultaneous (concurrent) and consecutive administration in any order.

As used herein, "hotspot" as it relates to sequences within the complementarity determining regions means the presence of amino residues that would cause instability for the antigen binding region, and thus such motif should be replaced for better efficiency of binding. While there is not a list of typically replaced amino acids, one way to consider replacing an amino acid residue on CDR is to consider the germline conservatism and antibody sequence structure, and choose and replace amino acid with similar structure. For example, NG may be mutated to NA as the structures of both amino acids are similar. Such modification allows for greater binding efficiency of the CDR to BAG2.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

As used herein, "fragments" or "functional derivatives" refers to biologically active amino acid sequence variants and fragments of the polypeptide of the present invention, as well as covalent modifications, including derivatives obtained by reaction with organic derivatizing agents, post-translational modifications, derivatives with nonproteinaceous polymers, and immunoadhesins.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-structures, such as polyamides.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change.

As used herein, "subject" is a vertebrate, preferably a mammal, more preferably a human.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase" or "enhance" or "activate" are all used herein to generally mean an increase of a property, level, or other parameter by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer such as glioblastoma, and prostate cancer, including but not limited to androgen-dependent prostate cancer and androgen-independent prostate cancer.

The term "effective amount" or "therapeutically effective amount" as used herein refers to the amount of one or more anti-BAG2 antibody or fragment thereof, or amount of pharmaceutical compositions comprising one or more anti-BAG2 antibody or fragment thereof as disclosed herein, to decrease at least one or more symptom of the disease or disorder, and relates to a sufficient amount of the pharmacological composition to provide the desired effect. The phrase "therapeutically effective amount" as used herein means a sufficient amount of the composition to treat a disorder, at a reasonable benefit/risk ratio applicable to any medical treatment.

As used herein, the term "administering," refers to the placement of an agent or a composition as disclosed herein into a subject by a method or route which results in at least partial localization of the agents or composition at a desired site. "Route of administration" may refer to any administration pathway known in the art, including but not limited to oral, topical, aerosol, nasal, via inhalation, anal, intra-anal, peri-anal, transmucosal, transdermal, parenteral, enteral, or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intravascular, intravenous, intraarterial, subarachnoid, subcapsular, subcutaneous, transmucosal, or transtracheal. Via the parenteral route, the agent or composition may be in the form of solutions or suspensions for infusion or for injection, or as lyophilized powders. Via the enteral route, the agent or composition can be in the form of capsules, gel capsules, tablets, sugar-coated tablets, syrups, suspensions, solutions, powders, granules, emulsions, microspheres or nanospheres or lipid vesicles or polymer vesicles allowing controlled release. Via the topical route, the agent or composition can be in the form of aerosol, lotion, cream, gel, ointment, suspensions, solutions or emulsions. In an embodiment, agent or composition may be provided in a powder form and mixed with a liquid, such as water, to form a beverage. In accordance with the present invention, "administering" can be self-administering. For example, it is considered as "administering" that a subject consumes a composition as disclosed herein.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In one embodiment, the subject is a human.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age. Thus, adult and newborn subjects, as well as fetuses, are intended to be included within the scope of this term.

A subject can be one who has been previously diagnosed with or identified as suffering from or having a condition in need of treatment (e.g., cancer or autoimmune diseases) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition.

By "at risk of" is intended to mean at increased risk of, compared to a normal subject, or compared to a control group, e.g. a patient population. Thus, a subject carrying a particular marker may have an increased risk for a specific disease or disorder, and be identified as needing further testing. "Increased risk" or "elevated risk" mean any statistically significant increase in the probability, e.g., that the subject has the disorder. The risk is preferably increased by at least 10%, more preferably at least 20%, and even more preferably at least 50% over the control group with which the comparison is being made.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, the term "co-administer" refers to administration of two or more therapies or two or more therapeutic agents (e.g., anti-BAG2 antibody and additional anti-cancer therapies) within a 24-hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. For example, when the anti-BAG2 antibody and the additional anti-cancer therapy are administered in different pharmaceutical compositions or at different times, routes of administration can be same or different.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397.

"Humanized" forms of non-human (e.g., murine) antibodies are chimeric immunoglobulins that contain minimal sequences derived from non-human immunoglobulin. In general, a humanized antibody will comprise substantially all of or at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332.

"Human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as LakePharma, Inc. (Belmont, Calif.) or Creative BioLabs (Shirley, N.Y.) can be engaged to provide human antibodies directed against a selected antigen using technology similar to that described above. Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., 1988, Biotechnology 12:899-903).

As used herein, the term "antibody-like" means a molecule that may be engineered such that it contains portions of antibodies but is not an antibody that would naturally occur in nature. Examples include but are not limited to CAR (chimeric antigen receptor) T cell technology and the Ylanthia® technology. The CAR technology uses an antibody epitope fused to a portion of a T cell so that the body's immune system is directed to attack a specific target protein or cell. The Ylanthia® technology consists of an "antibody-like" library that is a collection of synthetic human fabs that are then screened for binding to peptide epitopes from target proteins. The selected Fab regions can then be engineered into a scaffold or framework so that they resemble antibodies.

As used herein, "immunotherapeutic agent" or "immunomodulator" is an agent designed to elicit or amplify an immune response or reduce or suppress the response.

As used herein, "high homology" is considered to be at least 30%, 35%, 40%, 45%, 50%, 55%, 60%, 65%, 70%, 75%, 80%, 85%, 90%, 95%, or 97% identity in a designated overlapping region between any two polypeptides.

Hot Spot Removal

During manufacturing, storage and in vivo, therapeutic antibodies are at risk for degradation via a number of pathways. Amongst the most frequently occurring degradation reactions in proteins are the chemical degradation of Asn and Asp residues. While these reactions may be kept under control by appropriate storage and formulation conditions of the final drug substance and drug product, degradation during fermentation, downstream-processing, and in vivo can often not be controlled sufficiently. If Asn and Asp residues are involved in antigen recognition, their chemical alteration can lead to severe loss of potency. In several cases, these degradation events were reported to hamper long-term mAb functionality. In vivo, protein degradation events are described in connection with protein ageing, with cancer by triggering apoptosis or with severe effects on other biological functions, e. g. stability decrease of human lens betaA3-crystallin, abnormal MAPK signaling, the alteration of potential beta-secretase efficacy and specificity in the course of Abeta generation, or increase of lysozyme lytic activity against bacterial cells. The identification of degradation-prone drug candidates is ideally done early in the drug development process to either adjust the manufacturing and formulation process accordingly or to re-engineer a problematic candidate to remove such hotspots.

Asn and Asp residues share a degradation pathway that proceeds via the formation of a cyclic succinimide intermediate. Succinimide results from deamidation of Asn or dehydration of Asp by nucleophilic attack of the backbone nitrogen of the succeeding amino acid on the Asn/Asp side chain γ-carbonyl group. The metastable cyclic imide can hydrolyze at either one of its two carbonyl groups to form aspartyl or iso-aspartyl linkages in different ratios, depending on hydrolysis conditions and conformational restraints. In addition, alternative degradation mechanisms for Asn were proposed such as nucleophilic attack by the backbone carbonyl oxygen to form a cyclic isoimide or direct hydrolysis of Asn to Asp. Several analytical methods, mostly charge-sensitive methods such as ion exchange chromatography or isoelectric focusing, were described to detect either of the degradation products, i.e. succinimide, Asp or isoAsp. Most suitable for the quantification and the localization of degradation sites in proteins is the analysis via liquid chromatography tandem mass spectrometry (LC-MS/MS). The reference Sydow et al., "Structure-Based Prediction of Asparagine and Aspartate Degradation Sites in Antibody Variable Regions", PLoS One. 2014; 9(6): e100736. Published online 2014 Jun. 24. doi: 10.1371/journal.pone.0100736 is hereby incorporated by reference herein in its entirety for its disclosure of well-established knowledge of the existence of hotspots on antigen biding region of antibodies and desirability to replace such hotspot motifs to provide more stability to the protein.

One such example of the detection of and replacement of hotspot can be seen in antibody 3B5. VH CDR 2 is: YIDPYNGGNTYNRKFKG, however, hot spot was detected by the presence of "NG", which hot spot is removed and replaced with "NA" so that the hot spot removed sequence is YIDPYNAGNTYNRKFKG. Applicant notes that the presence of Y at the beginning of CDR2 should be considered part of CDR2. It is generally acknowledged in the art that a CDR sequence maintains its binding activity even if some of the sequences at the N-terminus or C-terminus is shortened or shorted by a few amino acids. It is believed that the length of the CDRs to retain its activity is well within reasonable experimentation to determine.

Humanization of Antibodies

The process of humanizing an antibody is well-known, and thus conventional techniques may be used to make humanized antibodies. One exemplified protocol may be as follows:

The mouse monoclonal antibodies are humanized by CDR grafting, and the critical residues of parental mouse antibody framework are identified and introduced to humanized sequences. Then the humanized VH/VLs are converted to full length hIgG1 format. Variants are expressed by transient transfection and purified by Affinity Chromatography. The purified antibodies are characterized by SEC-HPLC, SDS-PAGE, ELISA, and Biacore (affinity characterization). The best candidates with no more than 3-fold loss of affinity and potency are selected.

Five phases may be included in the antibody humanization process. First, humanization design of the antibody (hot spot removal feasibility and antibody humanization design) is completed.

The VH/VL CDR residues are determined and annotated with Kabat numbering system. Sequence analysis is applied to identify the major risky hot spots including unpaired cysteine residues, N-glycosylation sites, and deamination sites within the CDRs. Engineering work may be applied to remove the detrimental hot spot motifs. Hot spot removal feasibility are checked and carried out if there are hot spot in the CDRs.

Hot spot removal is designed, and the relative mouse-VH and mouse-VL are combined into several chimeric antibodies. Each chimeric antibody is transiently expressed in 100 mL 293 cells, and the supernatant is captured and purified by Mabselect PrismA (GE, 17549801), with the affinity purification yield recorded. The purified chimeric antibodies are tested by SDS-PAGE and HPLC-SEC, followed by affinity confirmation by ELISA or Biacore. Affinity ranking of the chimeric antibodies are performed to confirm the hot spot removal feasibility.

Such a humanized sequence may be as follows for the following antibodies;

3B5 subclone 1: VH region; underlined is CDR region after hot spot is checked for.

(SEQ ID NO: 75)
QVQLVQSGAEVKKPGASVKVSCKASGYSFTDYTFYWVRQAPGQRLEWIG
YIDPYNAGNTYNRKFKGRVTITVDKSASTAYMELSSLRSEDTAVYYCAR
GYYRYGGGGDFDYWGQGTLVTVSS

3B5 subclone 1: VL region; underlined is CDR region after hot spot is checked for.

(SEQ ID NO: 76)
DVVMTQSPLSLPVTLGQPASISCRSSQSLVHSNGNTYLHWFQQRPGQSP
RLLIHKVSNRFSGVPDRFSGSGSGTDFTLKISRVEAEDVGVYYCSQNTH
IPPTFGGGTKVEIK

3B5 subclone 2: VH region; underlined is CDR region after hot spot is checked for.

(SEQ ID NO: 77)
QVQLVQSGAEVKKPGASVKVSCKASGYSFTDYTFYWVRQAPGQRLEWIG
YIDPYNAGNTYNRKFKGKVTITVDKSASTAYMELNSLRSEDTAVYYCAR
GYYRYGGGGDFDYWGQGTLVTVSS

3B5 subclone 2: VL region; underlined is CDR region after hot spot is checked for.

(SEQ ID NO: 78)
DVVMTQSPLSLPVTLGQPASISCRSSQSLVHSNGNTYLHWFQQRPGQSP
RLLIHKVSNRFSGVPDRFSGSGSGTDFTLKISRVEAEDVGVYYCSQNTH
IPPTFGGGTKVEIK

3B10 subclone 1: VH region; underlined is CDR region after hot spot is checked for.

(SEQ ID NO: 79)
QVQLVQSGAEVKKPGASVKVSCKASGHAFTNYMIEWVRQAPGQGLEWM
GVINPGSGGTYNSEKVKGRVTLTADRSISTAYMELSRLRSDDTAVYYCR
IYGNYKGYFDHWGQGTLVTVSS

3B10 subclone 1: VL region; underlined is CDR region after hot spot is checked for.

(SEQ ID NO: 80)
DIQMTQSPSSLSASVGDRVTITCKASQDMNSYLSWFQQKPGKAPKSLIY
RSNRLVDGVPSRFSGSGSGTDFTLTISSLQPEDFATYYCLQNDEFPFTF
GQGTKLEIK

3B10 subclone 2: VH region; underlined is CDR region after hot spot is checked for.

(SEQ ID NO: 81)
QVQLVQSGSELKKPGASVKVSCKASGYSFTKYGMNWVKQAPGQGLEWM
GWINTNTGEATYGEEVKGRFVFSLDTSVSTAYLQISSLKAEDTAVYYCA
RLGLRYLDYWGQGTLVTVSS

3B10 subclone 2: VL region; underlined is CDR region after hot spot is checked for.

(SEQ ID NO: 82)
DIQMTQSPSSLSASVGDRVTITCRASKSVSTSDYSYMHWYQQKPGKAPK
LLIYLASNLESGVPSRFSGSGSGTDFTLTISSLQPEDFATYYCQHNREL
PPTFGQGTKLEIK

3G8 subclone 1: VH region; underlined is CDR region after hot spot is checked for.

(SEQ ID NO: 83)
QVQLVQSGSELKKPGASVKVSCKASGYSFTKYGMNWVRQAPGQGLEWM
GWINTNTGEATYGEEVKGRFVFSLDTSVSTAYLQISSLKAEDTAVYYCA
RLGLRYLDYWGQGTLVTVSS

3G8 subclone 1: VL region; underlined is CDR region after hot spot is checked for.

(SEQ ID NO: 84)
DIQMTQSPSSLSASVGDRVTITCRASKSVSTSDYSYMHWYQQKPGKAPK
LLIYLASNLESGVPSRFSGSGSGTDFTLTISSLQPEDFATYYCQHNREL
PPTFGQGTKLEIK

3G8 subclone 2: VH region; underlined is CDR region after hot spot is checked for.

(SEQ ID NO: 85)
QVQLVQSGSELKKPGASVKVSCKASGYSFTKYGMNWVKQAPGQGLEWM
GWINTNTGEATYGEEVKGRFVFSLDTSVSTAYLQISSLKAEDTAVYYCA
RLGLRYLDYWGQGTLVTVSS

3G8 subclone 2: VL region; underlined is CDR region after hot spot is checked for.

(SEQ ID NO: 86)
DIQMTQSPSSLSASVGDRVTITCRASKSVSTSDYSYMHWYQQKPGKAPK
LLIYLASNLESGVPSRFSGSGSGTDFTLTISSLQPEDFATYYCQHNREL
PPTFGQGTKLEIK

Use of Anti-Bag2 Antibody for Treatment of Cancer

Those antibodies that inhibit cancer growth or transition to a more metastatic state are selected for use as anti-cancer therapeutics and may be administered to a patient for the treatment or prevention of cancers. Selected antibodies may be further optimized for example by engineering or making human chimera antibodies or fully human antibodies. To demonstrate the efficacy of this approach, The detection of elevated levels of Bag2 in a patient sample is diagnostic of the presence of cancer or its progression to a more aggressive or metastatic state. Detection of elevated levels of BAG2 species in a patient sample will be indicators that the patient has a cancer or is at risk of developing a cancer. Levels of BAG2 species levels can be measured or assessed by PCR, hybridization schemes, cycling probe technologies, FISH, immunocytochemistry, IHC, Western blot, immunoprecipitation, sandwich assays, ELISA assays and the like. The patient sample may be a fluid sample, a blood sample, milk, urine, cells, liquid biopsy, biopsy and the like. In a patient diagnosed with cancer, elevated levels of BAG2 are indicators of increased metastatic potential. Elevated levels of BAG2 are indicators of prostate cancer. Antibodies of the invention are used to detect BAG2 and are used as a diagnostic tool.

Because cells and tissues do not normally secrete BAG2, an effective way to diagnose cancer or to diagnose a more aggressive or metastatic form, or a shift to a more aggressive form, is to measure levels of BAG2 in a sample from a patient, from a collection of cells or tissues or from cultured cells, compared to BAG2 levels in a healthy sample or compared to levels of BAG2 known to exist in healthy adult cells or tissues. Increased levels of BAG2 indicate the presence of cancer, the presence of a metastatic cancer or the onset of metastasis. The sample assayed for the presence of BAG2 may be a collection of cells that may be cultured cell lines or cells from a patient, a bodily fluid, a blood sample, a tissue specimen, or a biopsy specimen. Therefore, a diagnostic assay that will detect the presence of cancer or the progression of cancer, comprises the steps of: 1) obtaining a sample from a patient having cancer or at risk of developing a cancer; 2) subjecting that sample to an assay capable of detecting or measuring levels of BAG2; 3) comparing levels of the measured BAG2 protein in the test sample to levels in control patients or control cells; 4) determining that the levels of BAG2 are elevated compared to the controls; and 5) concluding that the donor of the test sample has cancer or has had a progression of cancer if the control to which the test was compared came from a donor previously diagnosed with a cancer.

In this assay, the control sample to which the test sample is compared can be non-cancerous cells, cultured cells, a sample from a healthy donor, a non-cancerous sample from the donor, or a sample from the donor of the test sample wherein the control sample was taken from the donor at a previous point in time. The source of such samples may be any specimen taken from the patient being tested for the presence or progression of cancer, including bodily fluids, cerebrospinal fluid, bone marrow samples, blood, tissues, cells, biopsy tissues or cells, cultured cells derived from a patient's cells and the like. The source of the sample to which the test sample is compared can be bodily fluids, cerebrospinal fluid, bone marrow samples, blood, tissues, cells, biopsy tissues or cells, or cultured cells that may be derived from a healthy donor or the test patient wherein the samples were taken at a previous point in time. The measured levels to which the test sample is compared may be from previously recorded data and compiled into lists for comparison to test samples.

Combination Therapy

A first agent is administered in conjunction with another agent. "In conjunction with" refers to administration of one treatment modality in addition to another treatment modality, such as administration of an immunomodulator described herein in addition to administration of the anti-BAG2 antibody or fragment thereof to the same individual. As such, "in conjunction with" refers to administration of one treatment modality before, during, or after delivery of the other treatment modality to the individual. Such combinations are considered to be part of a single treatment regiment or regime.

Immunomodulating Agent

Immunomodulating or immunotherapeutic agent can be roughly divided into four categories: checkpoint inhibitors, cytokines, agonists, and adjuvants. Checkpoint inhibitors work by blocking immune checkpoints—the "brakes" of the immune system—that tumors frequently manipulate in order to shut down immune responses and protect themselves. As a result, checkpoint inhibitors are able to unleash new immune responses against cancer as well as enhance existing responses to promote elimination of cancer cells. As of 2020, checkpoint inhibitors are perhaps the most well-known, and most widely successful, immunomodulators developed so far.

For example, PD-1/PD-L1 immune checkpoint pathway can shut down cancer-targeting T cells. However, when checkpoint inhibitors block the PD-1/PD-L1 pathway, they can enable T cells to eliminate cancer cells.

Cytokines are messenger molecules that regulate immune cell maturation, growth, and responsiveness. Currently, there are four FDA-approved cytokine immunotherapies—for the treatment of subsets of patients with kidney cancer, leukemia, lymphoma, melanoma, and sarcoma.

Agonists activate pathways that promote adaptive immune responses, either by helping to activate "killer" T cells, which directly attack cancer cells, or stimulating the activity of innate immune cells like dendritic cells, which coordinate overall immune responses against cancer by displaying cancer markers and enhancing T cell activity.

Adjuvants activate pathways involved in the innate immune system that can stimulate general immune responses and ultimately promote adaptive immune responses. One FDA-approved adjuvant immunotherapy is currently available for the treatment of subsets of patients with squamous cell carcinoma, a type of skin cancer.

Examples of such immunomodulators are granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), 4-1BB ligand, GITRL, OX-40L, anti-CD3 antibody, anti-CD27 antibody, anti-CTLA4 antibody, anti-PD-1 antibody, anti-PD-L1 antibody, anti-GITR antibody, anti-OX-40 antibody, anti-4-1BB antibody, anti-LAG-3 antibody, and anti-TIM-3 antibody.

Adjunctive Therapies

The anti-BAG2 antibodies may be used adjunctive to, or with, other agents or treatments having anti-cancer properties. When used adjunctively, the anti-BAG2 antibody and other agent(s) may be formulated together in a single, combination pharmaceutical formulation, or may be formulated and administered separately, either on a single coordinated dosing regimen or on different dosing regimens. Agents administered adjunctive to or with the anti-BAG2 antibodies will typically have complementary activities to the anti-BAG2 antibodies such that the antibodies and other agents do not adversely affect each other.

Agents that may be administered adjunctive to or with an anti-CD40 antibody include, but are not limited to, alkylating agents, angiogenesis inhibitors, antibodies, antimetabolites, antimitotics, antiproliferatives, antivirals, aurora kinase inhibitors, activators of death receptor pathway, Bcr-Abl kinase inhibitors, BiTE (Bi-Specific T cell Engager)

antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin (mTor) inhibitors, microRNAs, mitogen-activated extracellular signal-regulated kinase inhibitors, nonsteroidal anti-inflammatory drugs (NSAIDs), poly ADP (adenosine diphosphate)-ribose polymerase (PARP) inhibitors, platinum chemotherapeutics, Bruton's tyrosine kinase (BTK) inhibitors (e.g., ibrutinib, acalabrutinib), polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, as well as combinations of one or more of these agents.

Examples of immunologicals include, but are not limited to, interferons, immune checkpoint inhibitors, and other immune-enhancing agents. Interferons include interferon alpha, interferon alpha-2a, interferon alpha-2b, interferon beta, interferon gamma-1a, interferon gamma-1b or interferon gamma-n1, combinations thereof and the like. Immune check point inhibitors include antibodies that target PD-1 (e.g., pembrolizumab and nivolumab), PD-L1 (e.g., durvalumab, atezolizumab, avelumab, MEDI4736, MSB0010718C and MPDL3280A), and CTLA4 (cytotoxic lymphocyte antigen 4; e.g., ipilimumab, tremelimumab). Immune-enhancing agents include anti-OX40 agonist antibodies that activate T cells.

An anti-BAG2 antibody may also be used to enhance the efficacy of radiation therapy. Examples of radiation therapy include external beam radiation therapy, internal radiation therapy (i.e., brachytherapy) and systemic radiation therapy.
Theranostics Patients diagnosed with elevated levels of secreted BAG2 protein are then treated with therapeutic agents that specifically bind to BAG2. Therefore, patients diagnosed with elevated secreted levels of BAG2 will benefit from treatment with therapeutic agents that inhibit BAG2. Thus assessing suitability of cancer treatments and administration of an effective amount of a therapeutic for the treatment or prevention of cancers would consists of the steps of: 1) obtaining a sample from a patient suspected of having a cancer or at risk of developing a cancer or at risk of developing a metastatic cancer; 2) measuring an amount of secreted BAG2 wherein the measured levels are significantly above those measured in a control sample; 3) determining that the patient has a cancer or has developed a more aggressive or a metastatic cancer; 4) administering to the patient an effective amount of a therapeutic agent that suppresses expression of BAG2. In a preferred embodiment, the therapeutic agent that inhibits
Chemically Modified Peptides Polypeptide or antibody therapeutics may suffer from short circulating half-life, and proteolytic degradation and low solubility. To improve the pharmacokinetics and pharmacodynamics properties of the inventive biopharmaceuticals, methods such as manipulation of the amino acid sequence may be made to decrease or increase immunogenicity and decrease proteolytic cleavage; fusion or conjugation of the peptides to immunoglobulins and serum proteins, such as albumin may be made; incorporation into drug delivery vehicles for the biopharmaceuticals such as the inventive peptides and antibodies for protection and slow release may also be made; and conjugating to natural or synthetic polymers are also contemplated. In particular, for synthetic polymer conjugation, pegylation or acylation, such as N-acylation, S-acylation and so forth are also contemplated.
Nucleic Acid Constructs Also provided is an expression vector comprising a nucleic acid molecule of the invention as described herein, wherein the nucleic acid molecule is operatively linked to an expression control sequence. Also provided is a host-vector system for the production of a polypeptide which comprises the expression vector of the invention which has been introduced into a host cell suitable for expression of the polypeptide. The suitable host cell may be a bacterial cell such as *E. coli*, a yeast cell, such as *Pichia pastoris*, an insect cell, such as *Spodoptera frugiperda*, or a mammalian cell, such as a COS, HEK or CHO cell.

The present invention also provides for methods of producing the polypeptides of the invention by growing cells of the host-vector system described herein, under conditions permitting production of the polypeptide and recovering the polypeptide so produced. The polypeptides useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pZErO.

The polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography or gel filtration.

Any of the methods known to one skilled in the art for the insertion of DNA fragments into a vector may be used to construct expression vectors encoding the polypeptides of the invention using appropriate transcriptional/translational control signals and protein coding sequences. These methods may include in vitro recombinant DNA and synthetic techniques and in vivo recombinations (genetic recombination). Expression of nucleic acid sequence encoding the polypeptides of the invention may be regulated by a second nucleic acid sequence so that the polypeptide is expressed in a host transformed with the recombinant DNA molecule. For example, expression of the polypeptides described herein may be controlled by any promoter/enhancer element known in the art. Promoters which may be used to control expression of the polypeptide include, but are not limited to, the long terminal repeat as described in Squinto et al., (1991, Cell 65:1-20); the SV40 early promoter region (Bernoist and Chambon, 1981, Nature 290:304-310), the CMV promoter, the M-MuLV 5' terminal repeat the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionein gene (Brinster et al., 1982, Nature 296:39-42);

prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25), see also "Useful proteins from recombinant bacteria" in Scientific American, 1980, 242:74-94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), Sendai virus, lenti virus, albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987, Cell 48:703-712); myosin light chain-2 gene control region which is active in skeletal muscle (Shani, 1985, Nature 314:283-286), and gonadotropic releasing hormone gene control region which is active in the hypothalamus (Mason et al., 1986, Science 234:1372-1378).

Thus, according to the invention, expression vectors capable of being replicated in a bacterial or eukaryotic host comprising nucleic acids encoding a polypeptide as described herein, are used to transfect the host and thereby direct expression of such nucleic acid to produce polypeptides which may then be recovered in biologically active form. As used herein, a biologically active form includes a form capable of binding to the relevant receptor and causing a differentiated function and/or influencing the phenotype of the cell expressing the receptor.

Expression vectors containing the nucleic acid inserts can be identified by without limitation, at least three general approaches: (a) DNA-DNA hybridization, (b) presence or absence of "marker" gene functions, and (c) expression of inserted sequences. In the first approach, the presence of foreign nucleic acids inserted in an expression vector can be detected by DNA-DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an ef1 nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant constructs. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

The polypeptide, in particular modified of the present invention, may be expressed in the host cells transiently, constitutively or permanently.

Effective doses useful for treating the diseases or disorders indicated in the present application may be determined using methods known to one skilled in the art (see, for example, Fingl, et al., The Pharmacological Basis of Therapeutics, Goodman and Gilman, eds. Macmillan Publishing Co, New York, pp. 1-46 (1975). Pharmaceutical compositions for use according to the invention include the polypeptides described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation prior to administration in vivo. For example, the pharmaceutical composition may comprise a polypeptide in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, intrauterinely, by injection into involved tissue, intraarterially, intranasally, orally, or via an implanted device.

Administration may result in the distribution of the active agent of the invention throughout the body or in a localized area. For example, in some conditions, which involve distant regions of the nervous system, intravenous or intrathecal administration of agent may be desirable. In some situations, an implant containing active agent may be placed in or near the lesioned area. Suitable implants include, but are not limited to, gelfoam, wax, spray, or microparticle-based implants.

The present invention also provides for pharmaceutical compositions comprising the polypeptides described herein, in a pharmacologically acceptable vehicle. The compositions may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

Gene Therapy

Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Lentiviral vectors, such as retroviral vectors, and other vectors such as adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patient.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

The formulation of therapeutic compounds is generally known in the art and reference can conveniently be made to Remington's Pharmaceutical Sciences, 17th ed., Mack Publishing Co., Easton, Pa., USA. For example, from about 0.05 ng to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intra ocular, intradermal or suppository routes or implanting (eg using slow release molecules by the intraperitoneal route or by using cells e.g. monocytes or dendrite cells sensitized in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, intra ocular, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, thus requiring only a fraction of the systemic dose.

The following examples are offered by way of illustration of the present invention, and not by way of limitation.

EXAMPLES

Example 1: Selection, Sequencing and Antigen-Antibody Reaction of Anti-BAG2 Antibody 1. Selection of Monoclonal Antibodies Targeting BAG2 and Analysis of Amino Acid Sequences Thereof The inventors selected antibodies targeting BAG2, analyzed their amino acid sequences, and determined the complementarity determining region (CDR) of each of the antibodies.

In detail, a gene consisting of the nucleotide sequence of SEQ ID NO: 70 encoding the human BAG2 protein consisting of the amino acid sequence of SEQ ID NO: 69 was cloned into a pCAGGS plasmid and linearized, and then the linearized construct was inoculated into the muscles of five 6-week-old female BALB/c mice by the appliance of electroshock. The construct was inoculated intramuscularly three times at three-week intervals, and consisted of 100 ug of DNA in 100 ul of PBS. At this time, the plasmid of the control group was also subjected to the same manner. To produce therapeutic and diagnostic antibodies, a more efficient DNA vaccine-based immunization strategy than protein-based antigen injection was performed. Blood was collected from the fundus vena cava or the caudal vein of the mouse, and examined by enzyme immunoassay showing the serum antibody titer, and spleens were extracted 3 days after the last immunization from the mouse showing sufficient antibody titer. B lymphocytes were isolated from the spleen, followed by fusion with the myeloma cells cultured with the isolated B lymphocytes, that is, the SP2/0-Ag14 cell line of ATCC, thereby obtaining fused cells. After fused cells were cultured in HAT medium containing hypoxanthin, aminopterine, and thymidine, hybridoma cells fused only with myeloma and B lymphocytes were obtained by selecting approximately 130 clones. Of the hybridoma cells obtained through the selection process by immunoblotting, 10 hybridoma cells producing antibodies specifically binding to human BAG2 protein were obtained.

Total RNA of anti-BAG2 antibodies was produced from the $5 \times 10^6$ hybridoma cells, and 5'-RACE-cDNA was produced from 100 ng total RNA by using SMART RACE cDNA Amplification kit (Clontech) according to the instructions of the manufacturer. A heavy chain variable region (VH) and a light chain variable region (VL) coding regions were amplified by PCR, and the amplified genes were inserted into the pGEM-T vector (Promega, USA), cloned, and nucleotide sequences thereof were analyzed by using an automated genetic analyzer (ABI Prism 310, Applied Biosystem Co.). The nucleotide sequences of the analyzed genes were identified by comparison with the previously reported nucleotide sequence, and the identified nucleotide sequences were artificially translated for use in determining sequences of complementarity determining regions VH-CDR1, -CDR2, and -CDR3 and VL-CDR1, -CDR2, and -CDR3. The determining the sequences of complementarity determining regions was performed using Kabat's database (http://www.bioinf.org.uk/abs/).

As a result, 10 anti-BAG2 antibodies specifically binding to BAG2 were obtained from the hybridoma cells. 10 anti-BAG2 antibodies were 2A11, 4C2, 8C4, 3B5, 9B3, 9B12, 3B10, 10H7, 3 GB, and 3F12 antibodies. In addition, the amino acid sequences of a heavy chain variable region, a light chain variable region and complementarity determining regions thereof as shown in Tables 1 to 3 and the nucleotide sequences of the genes encoding the antibodies were determined.

2A11, 4C2, and 8C4 antibodies include a heavy chain variable region consisting of an amino acid sequence of SEQ ID NO: 21 and a light chain variable region consisting of an amino acid sequence of SEQ ID NO: 27. In the 2A11 antibody, the 56th and 57th Xaa of SEQ ID NO: 21 are each Gly and the 53rd Xaa of SEQ ID NO: 27 is Ile. In the 4C2 antibody, 56th Xaa and 57th Xaa of SEQ ID NO: 21 are Gly and Ala, respectively, and 53rd Xaa of SEQ ID NO: 27 is Phe. In the 8C4 antibody, 56th Xaa and 57th Xaa of SEQ ID NO: 21 are Ala and Gly, respectively, and 53rd Xaa of SEQ ID NO: 27 is Phe.

VH-CDR1, -CDR2 and -CDR3 of 2A11, 4C2, and 8C4 antibodies consist of amino acid sequences of SEQ ID NOS: 33, 39 and 45, respectively, and VL-CDR1, -CDR2 and -CDR3 consist of amino acid sequences of SEQ ID NOS: 51, 57, and 63, respectively. In 2A11 antibody, 56th and 57th Xaa of SEQ ID NO: 21 each are Gly. Regarding 4C2 antibody, in SEQ ID NO: 21, 56th Xaa is Gly and 57th Xaa is Ala. Regarding 8C4 antibody, in SEQ ID NO: 21, 56th Xaa is Ala and 57th Xaa is Gly.

9B3, 9B12 and 3B10 antibodies include a heavy chain variable region consisting of an amino acid sequence of SEQ ID NO: 23 and a light chain variable region consisting of an amino acid sequence of SEQ ID NO: 29. Regarding 9B3 antibody, in SEQ ID NO: 23, 1st Xaa is Glu, 7th Xaa is Ser, 12th Xaa is Val, 27th Xaa is Tyr, 58th Xaa is Ser, 61st Xaa is Asn, 74th Xaa is Lys, 83rd Xaa is Phe, 92nd Xaa is Ala, and 108th Xaa is Tyr. Regarding 9B3 antibody, in SEQ ID NO: 29th Xaa is Ile, 51st Xaa is Ala, 79th Xaa is Glu, and 106th Xaa is Ile. Regarding 9B12 antibody, in SEQ ID NO:23 1st Xaa is Gin, 7th Xaa is Ser, 12th Xaa is Val, 27th Xaa is Tyr, 58th Xaa is Ser, 61st Xaa is Asn, 74th Xaa is Arg, 83rd Xaa is Phe, 92nd Xaa is Gly, and 108th Xaa is His. Regarding 9B12 antibody, in SEQ ID NO: 29, 29th Xaa is Met, 51th Xaa is Ala, 79th Xaa is Glu, and 106th Xaa is Met. Regarding 3B10 antibody, in SEQ ID NO: 23, 1st Xaa is Gln, 7th Xaa is Pro, 12th Xaa is Ala, 27th Xaa is His, 58th Xaa is Thr, 61st Xaa is Ser, 74th Xaa is Arg, 83rd Xaa is Leu, 92th 92nd Xaa is Gly, and 108th Xaa is His. Regarding 3B10 antibody, in SEQ ID NO: 29, 29th Xaa is Met, 51st Xaa is Ser, 79th Xaa is Asp, and 106th Xaa is Ile.

Regarding 9B3, 9B12, and 3B10 antibodies, VH-CDR1, -CDR2, and -CDR3 consist of the amino acid sequences of SEQ ID NOS: 35, 41, and 47, respectively, and VL-CDR1, -CDR2, and -CDR3 consist of the amino acid sequences of SEQ ID NOS: 53, 59, and 65, respectively. Regarding 9B3 antibody, 2nd Xaa of SEQ ID NO: 35 is Tyr, 8th Xaa of SEQ ID NO: 41 is Ser, 12th Xaa of SEQ ID NO: 47 is Tyr, 3rd Xaa of SEQ ID NO: 53 is Ile, and 2nd Xaa of SEQ ID NO: 59 is Ala. Regarding 9B12 antibody, 2nd Xaa of SEQ ID NO: 35 is Tyr, 8th Xaa of SEQ ID NO: 41 is Ser, 12th Xaa of SEQ ID NO: 47 is His, 3rd Xaa of SEQ ID NO: 53 is Met, and 2nd Xaa of SEQ ID NO: 59 is Ala. Regarding 3B10 antibody, 2nd Xaa of SEQ ID NO: 35 is His, 8th Xaa of SEQ ID NO: 41 is Thr, 12th Xaa of SEQ ID NO: 47 is His, 3rd Xaa of SEQ ID NO: 53 is Met, and 2nd Xaa of SEQ ID NO: 59 is Ser.

TABLE 1

| Antibody Name | Nucleotide sequence of the VH gene | Nucleotide Sequence of the VL gene |
|---|---|---|
| 2A11 | SEQ ID NO: 1 | SEQ ID NO: 11 |
| 4C2 | SEQ ID NO: 2 | SEQ ID NO: 12 |
| 8C4 | SEQ ID NO: 3 | SEQ ID NO: 13 |
| 3B5 | SEQ ID NO: 4 | SEQ ID NO: 14 |
| 9B3 | SEQ ID NO: 5 | SEQ ID NO: 15 |
| 9B12 | SEQ ID NO: 6 | SEQ ID NO: 16 |
| 3B10 | SEQ ID NO: 7 | SEQ ID NO: 17 |
| 10H7 | SEQ ID NO: 8 | SEQ ID NO: 18 |
| 3G8 | SEQ ID NO: 9 | SEQ ID NO: 19 |
| 3F12 | SEQ ID NO: 10 | SEQ ID NO: 20 |

TABLE 2

| Antibody Name | Amino acid sequence of the VH region | Amino acid sequence of the VL region |
|---|---|---|
| 2A11 | SEQ ID NO: 21 | SEQ ID NO: 27 |
| 4C2 | SEQ ID NO: 21 | SEQ ID NO: 27 |
| 8C4 | SEQ ID NO: 21 | SEQ ID NO: 27 |
| 3B5 | SEQ ID NO: 22 | SEQ ID NO: 28 |
| 9B3 | SEQ ID NO: 23 | SEQ ID NO: 29 |
| 9B12 | SEQ ID NO: 23 | SEQ ID NO: 29 |
| 3B10 | SEQ ID NO: 23 | SEQ ID NO: 29 |
| 10H7 | SEQ ID NO: 24 | SEQ ID NO: 30 |
| 3G8 | SEQ ID NO: 25 | SEQ ID NO: 31 |
| 3F12 | SEQ ID NO: 26 | SEQ ID NO: 32 |

TABLE 3

| Antibody Name | Amino acid sequence of VH-CDR1 | Amino acid sequence of VH-CDR2 | Amino acid sequence of VH-CDR3 | Amino acid sequence of VL-CDR1 | Amino acid sequence of VL-CDR2 | Amino acid sequence of VL-CDR3 |
|---|---|---|---|---|---|---|
| 2A11 | SEQ ID NO: 33 | SEQ ID NO: 39 | SEQ ID NO: 45 | SEQ ID NO: 51 | SEQ ID NO: 57 | SEQ ID NO: 63 |
| 4C2 | SEQ ID NO: 33 | SEQ ID NO: 39 | SEQ ID NO: 45 | SEQ ID NO: 51 | SEQ ID NO: 57 | SEQ ID NO: 63 |
| 8C4 | SEQ ID NO: 33 | SEQ ID NO: 39 | SEQ ID NO: 45 | SEQ ID NO: 51 | SEQ ID NO: 57 | SEQ ID NO: 63 |
| 3B5 | SEQ ID NO: 34 | SEQ ID NO: 40 | SEQ ID NO: 46 | SEQ ID NO: 52 | SEQ ID NO: 58 | SEQ ID NO: 64 |
| 9B3 | SEQ ID NO: 35 | SEQ ID NO: 41 | SEQ ID NO: 47 | SEQ ID NO: 53 | SEQ ID NO: 59 | SEQ ID NO: 65 |
| 9B12 | SEQ ID NO: 35 | SEQ ID NO: 41 | SEQ ID NO: 47 | SEQ ID NO: 53 | SEQ ID NO: 59 | SEQ ID NO: 65 |
| 3B10 | SEQ ID NO: 35 | SEQ ID NO: 41 | SEQ ID NO: 47 | SEQ ID NO: 53 | SEQ ID NO: 59 | SEQ ID NO: 65 |
| 10H7 | SEQ ID NO: 36 | SEQ ID NO: 42 | SEQ ID NO: 48 | SEQ ID NO: 54 | SEQ ID NO: 60 | SEQ ID NO: 66 |
| 3G8 | SEQ ID NO: 37 | SEQ ID NO: 43 | SEQ ID NO: 49 | SEQ ID NO: 55 | SEQ ID NO: 61 | SEQ ID NO: 67 |
| 3F12 | SEQ ID NO: 38 | SEQ ID NO: 44 | SEQ ID NO: 50 | SEQ ID NO: 56 | SEQ ID NO: 62 | SEQ ID NO: 68 |

2. Identification of Antigen-Antibody Responses of Anti-BAG2 Antibodies in Breast Cancer Cells FIG. 1 shows the results of immunoblotting of anti-BAG2 antibodies produced from 10 mouse hybridoma cells. Specifically, MDA-MB-231 cells, which are human breast cancer cells, were cultured in DMEM (Welgene) medium containing 10% FBS, 100 U/ml penicillin and 100 μg/ml streptomycin at a temperature of 37° C. The cells were harvested from wells and washed with PBS, and dissolved in a lysis buffer solution containing 1% Brij 97, 5 mM EDTA, 0.02M HEPES pH 7.3, 0.15M NaCl, 1 mM PMSF, 0.5 mM NaF, 10 μg/rni aprotinin, and 0.2 mM sodium orthovanadate. After 15 minutes of incubation on ice, the nuclei were removed from the cells by centrifugation and the supernatants were collected. 2× sample buffer consisting of 20% glycerol, 4.6% SOS, 0.125M tris, pH 6.8, 0.1% bromophenol blue was added to an appropriate amount of the supernatants. 10 ug protein samples were subjected to SOS-PAGE analysis on a 12% gel under standard conditions by using a mini-Protean II system (Bio-Rad Hercules, CA). For immune blotting, the protein was transferred to Millipore, a PVDF membrane. A blocking solution consisting of 0.1% Tween 20 and 5% bovine serum albumin (BSA) in TBS was allowed to react for 1 hour. Subsequently, the primary antibody was a 1/2000 dilution of anti-BAG2 antibody extracted from hybridoma cell culture, and the goat anti-mouse HRP conjugate (Dako) used as the secondary antibody was diluted to 1/5000. Film-photosensing was carried out in the dark using EGL reagent (Amersham Pharmacia Biotech) as a substrate. The photosensitized bands were compared to standard molecular markers to identify the bands corresponding to the size of BAG2.

As a result, as shown in FIG. 1, compared with the ab58682 (Abeam), a commercial polyclonal anti-BAG2 antibody used as a positive control, the antibodies 2A11, 3B5, 3B10, 3F12, 3 GB, 4C2, 8C4, 9B3, 9B12 and 10H7 showed antigen-antibody reactions, targeting BAG2.

Next, for domain mapping of the BAG2 antigen to which the ten antibodies identified in Section 1 above, cells, to which the GST-Empty vector (pcDNA3.1+/GST vector, NovoPro Bioscience Inc. China) having a molecular weight of about 26 kDa was introduced, was used as a negative control. GST-Bag Full vector, GST-Bag F1 vector, GST-Bag F2 vector, GST-Bag F3 vector, and GST-Bag F4 vector, each including polynucleotides encoding human BAG2 protein and polynucleotides encoding fragments of the BAG2 protein, were introduced into cells, and the cells with the vectors introduced thereinto were cultured to express the genes, and then, cell lysates were obtained. For cell lysates, immunoblotting was performed using each of the 10 antibodies. The polynucleotide encoding the human BAG2 protein has the nucleotide sequence of SEQ ID NO: 70. The GST-Bag F1, -Bag F2, -Bag F3, and -Bag F4 vectors consist of the nucleotide sequences of SEQ ID NOS: 71 to 74, respectively.

Figure 2A:
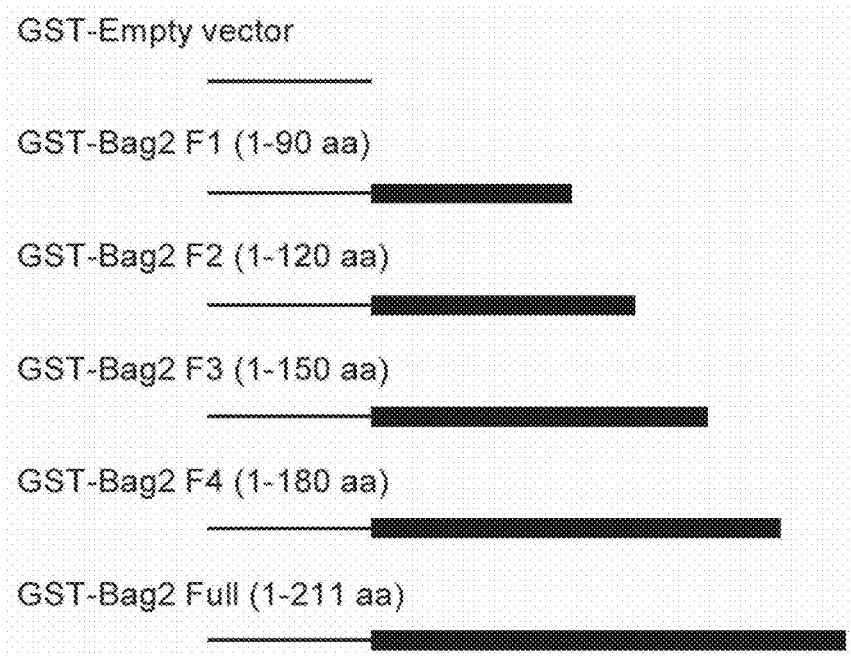
FIGS. 2A and 2B show the results of Western blotting for the full-length BAG2 polypeptide of anti-BAG2 antibody or a fragment thereof.
Figure 2B:
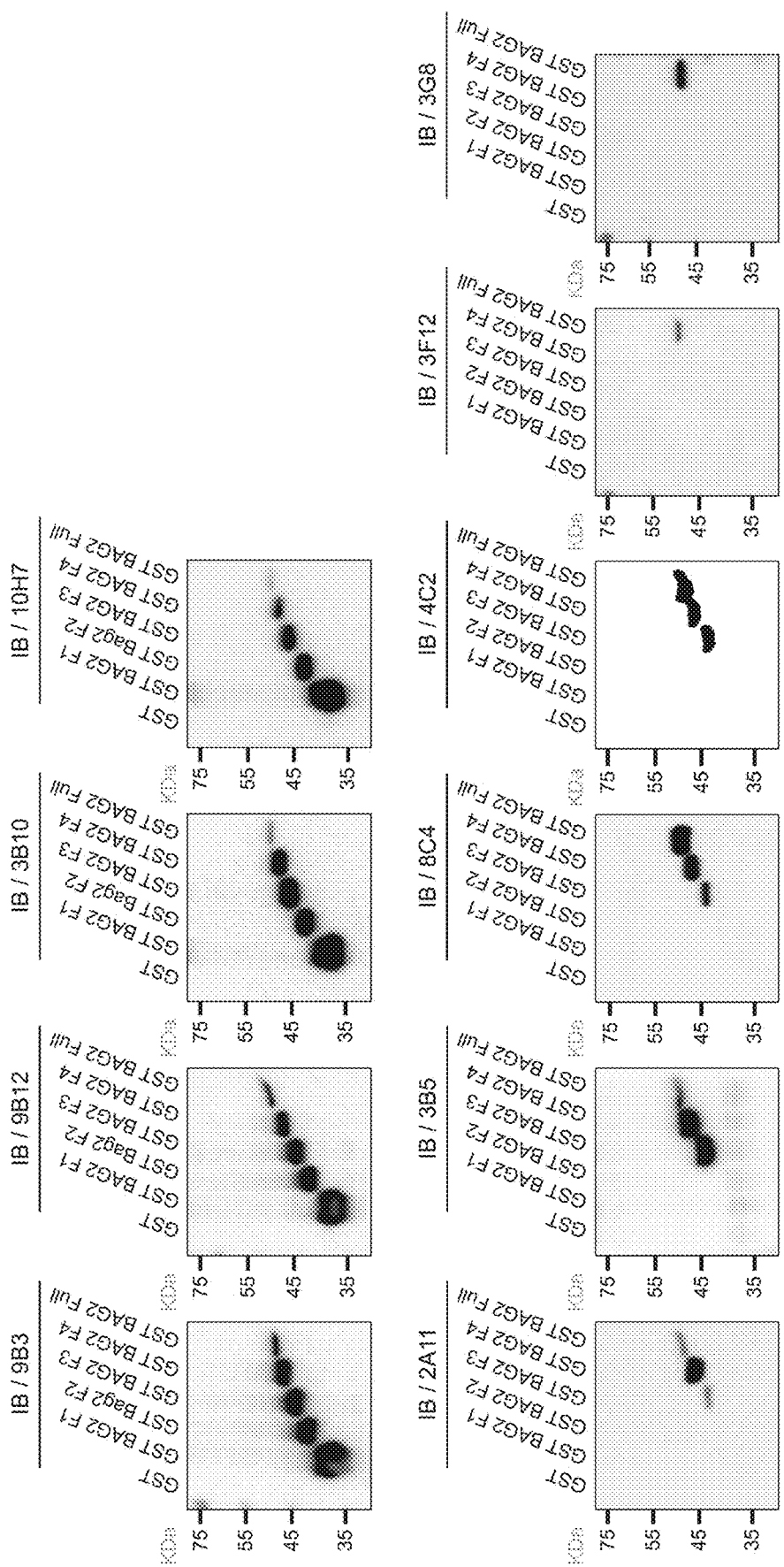

FIGS. 2A and 2B show the results of immunoblotting for the full-length BAG2 polypeptide of anti-BAG2 antibody or a fragment thereof. In FIG. 2, A shows diagrams of the vectors and BAG2 proteins and fragments thereof, and B shows the results of immunoblotting. In detail, the immunoblotting was performed as follows: each of the vectors was introduced into HEK293T cells by lipofectamine transfection (Thermo Fisher Scientific, Inc., Waltham, MA, USA) method, and the obtained transformed cells were cultured at a temperature of 37° C. in DMEM (Welgene) medium containing 10% FBS, 100 U/ml penicillin and 100 µg/ml streptomycin for 30 hours, and then cells were isolated. The isolated cells were disrupted using the same method as described in connection with FIG. 1 and subjected to SOS-PAGE analysis on a 12% gel. For immunoblotting, after reacting for 1 hour with the same blocking solution as described in connection with FIG. 1, each of the 10 purified anti-BAG2 antibodies having a concentration of 2 mg/ml was used as a primary antibody at a dilution of 1/10000 dilution and bound to the cells. The goat anti-mouse HRP conjugate used as the secondary antibody was used at a 1/5000 dilution concentration, and Film-photosensing was carried out in the dark using EGL reagent (Amersham Pharmacia Biotech) as a substrate. Standard molecular marker sizes were expressed to confirm the size of BAG2.

As a result, as shown in FIG. 2, each anti-BAG2 antibody was differentially bound to the full-length BAG2 polypeptide or fragments thereof. In particular, for each of the 10 anti-BAG2 antibodies, signals were commonly detected at the position of about 50 KDa in GST-Bag Full vector-introduced cell lysates. This result shows that all of these antibodies can bind to full-length BAG2 polypeptides. Finally, the domain region of BAG2 to which each anti-BAG2 antibody reacts was identified.

Figure 3:
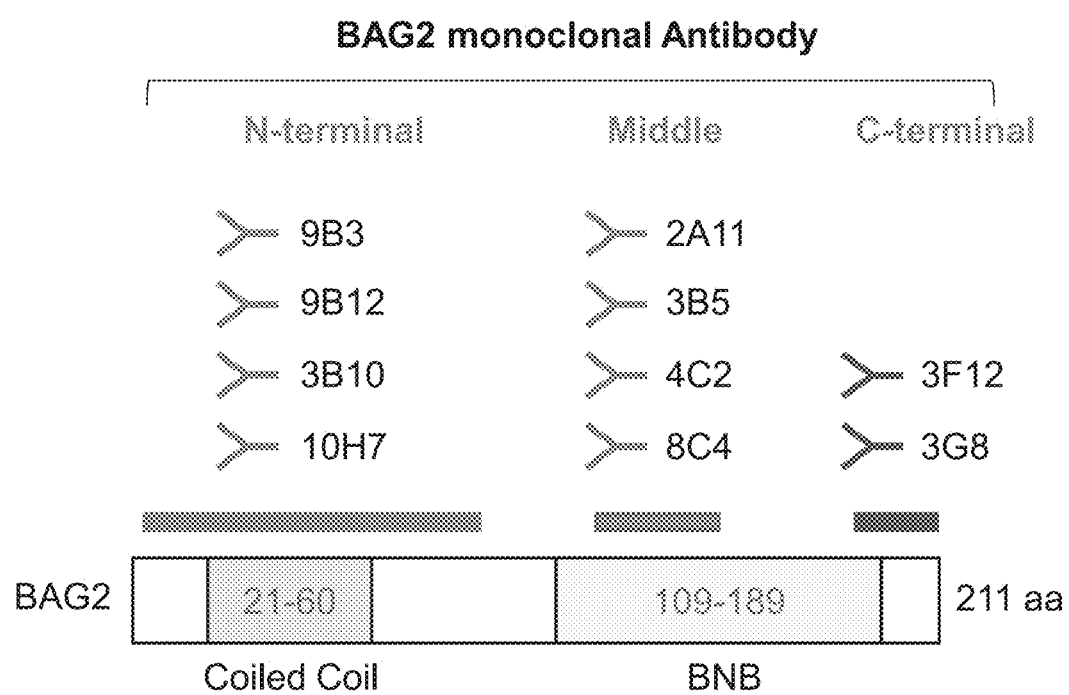
FIG. 3 shows a BAG2 domain which reacts with respective anti-BAG2 antibodies.

FIG. 3 shows a BAG2 domain which reacts with respective anti-BAG2 antibodies. As shown in FIG. 3, 9B3, 9B12, 3B10, and 10H7 antibodies were bound to the N-terminus of BAG2 protein, 2A11, 3B5, 4C2, and 8C4 antibodies were bound to a middle region of BAG2 protein, and 3F12 and 3 GB antibodies were bound to the C-terminus of BAG2 protein. The N-terminus commonly includes a coiled coil region of 21-60 amino acids, and the middle region is bound to a portion of the BNB region of 109-189 amino acids. Therefore, by using a set of antibodies that bind to different sites, the BAG2 protein or its fragments present in the sample may be detected with high sensitivity and specificity.

Antibodies or antigen-binding fragments thereof that specifically bind to BAG2 polypeptide or fragments thereof according to one aspect may cause an antigen-antibody reaction with various lengths of BAG2 polypeptide or a fragment thereof.

Polynucleotides encoding antibody or antigen-binding fragments thereof and host cells including the same according to another aspect may be used to produce antibodies or antigen-binding fragments thereof.

According to the method of producing an antibody or antigen binding thereof according to another aspect, antibodies or antigen-binding fragments thereof may be efficiently produced.

Example 2. Drug and Preparation of Mouse Model for Method of Treatment of Cancer Ten hybridoma cell lines of anti-BAG2 were purified from respective culture supernatant by affinity chromatography in Sepharose protein A/G columns according to manufacturer's instructions (GE Healthcare Biosciences AB). Control-Mu-IgG2a (ATCC, CCL-167™) was used as isotype control antibody and obtained from American Type Culture Collection. The anti-BAG2 mouse antibody and isotype control antibody used in in vitro and in vivo studies were produced in endotoxin-free conditions (<0.01EU/ug) by Nanotools.

Anti-PD-L1 monoclonal antibody (BioXCell, cat, No. BE0101), anti-PD-1 monoclonal antibody (BioXCell, Cat. No. BE0033-2), and anti-CTLA4 monoclonal antibody (BioXCell, Cat. No. BE0131) were prepared according to manufacturer's instructions.

In order to validate in vivo anti-tumor effects, male 5 week-old SPF C57BL/6 and BALB/c mice were purchased from Koatech Co. (South Korea). These mice were maintained in room controlled at a temperature of about 22° C., while freely supplying food and water to them. 1 week after, $2 \times 10^5$ cells of mouse EMT6 mammary carcinoma cell line (ATCC, CRL-2755™), $5 \times 10^5$ cells of mouse Lewis lung carcinoma (LLC) cell line (ATCC, CRL1642™), $5 \times 10^5$ cells of mouse MC38 colon carcinoma cell line (Kerafast, ENH204-FP), and $3 \times 10^5$ cells of mouse CT26 colorectal cancer cell line (ATCC, CRL2638™) were injected to these 6 week-old mice by subcutaneous injection. 7-8-week-old mice, 8 to 12 days after the injection of EMT6, LLC, MC38, and CT26 cell lines were used in the experiment. 1 week after, $2 \times 10^5$ cells of mouse B16-F10-Luc2 skin melanoma cell line (ATCC, CRL-6475-Luc2™) were injected to these 7-week-old mice by intravenous tail injection. 9-week-old mice, 15 days after the injection of B16-F10-Luc2 were used in the experiment. 1 week after, $2 \times 10^6$ cells of mouse PANC02-Luc pancreatic adenocarcinoma cell line (Professor Kyu Lim, Chungnam National University, Republic of Korea) were orthotopically implanted in the tail of the pancreas of 7-week-old mice. 10-week-old mice, 16 days after the injection of PANC02-Luc cell lines, were used in the experiment.

Mechanism of Action

Tumor secreted BAG2 protein can bind to surface of lymphoid-, myeloid-, and stromal-cells for anti-immunity (adaptive or innate immunity) in tumor microenviroment. We hypothesized that BAG2 neutralization would target lymphoid-, myeloid-, or stroma-mediated immunosuppression, while an immune checkpoint inhibitor would restore the function of anergized antitumor T-cells and proinflammatory property of myeloid-cells.

2.1 Results of Treating Breast Cancer in Mouse Model

The results show the following:

Anti-BAG2 antibody alone has an antitumor activity in mouse breast cancer model

Combined therapies of anti-BAG2 antibody and anti-PD-L1 antibody have a synergistic antitumor activity in mouse breast cancer model.

Figure 4A:
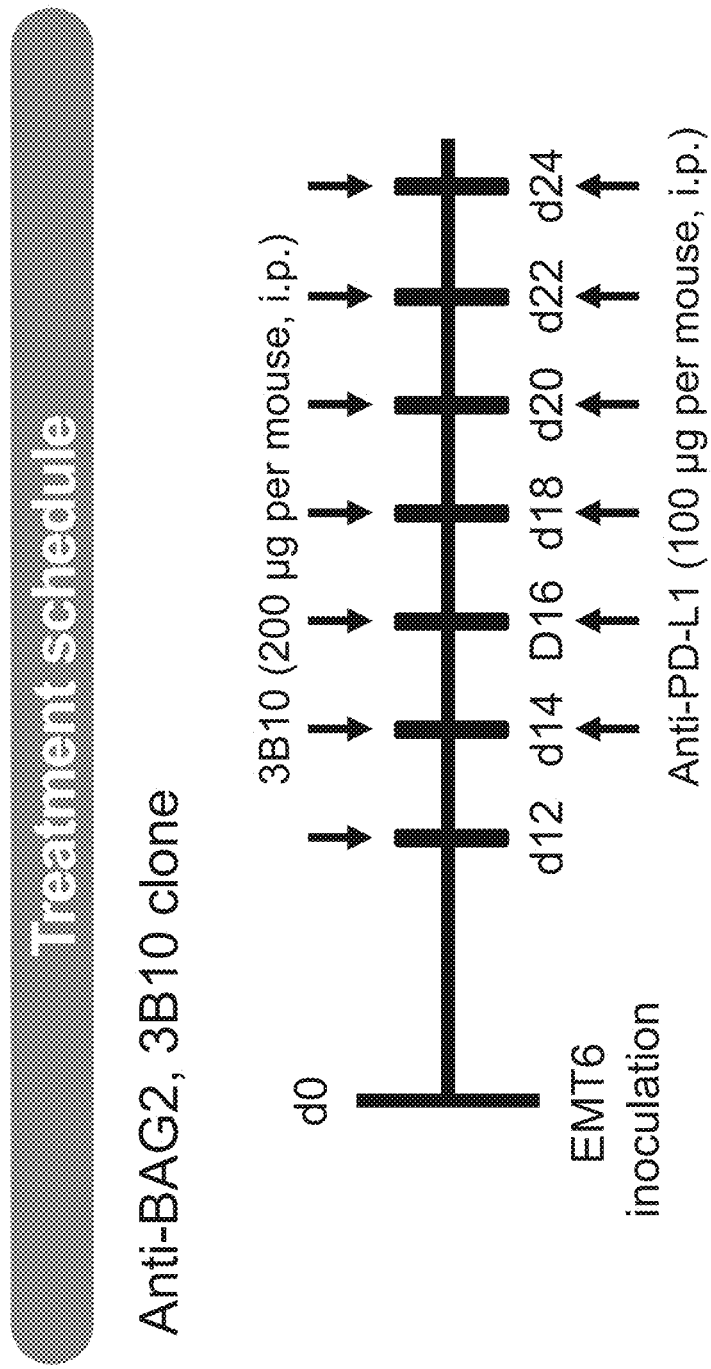
FIGS. 4A to 4D show therapeutic efficacy of anti-BAG2 antibody in combination with anti-PD-L1 antibody in a breast cancer model. (a) BALB/c mice were injected with $2 \times 10^5$ EMT6 cells. On days 12 after tumor cell injection, some of the mice were injected intraperitoneally (i.p.) with anti-BAG2 antibody 3B10 (200 μg per mouse) or isotype control antibody once every two days. On day 14, some mice received a single injection of anti-PD-L1 (100 μg per mouse, i.p.) or isotype control antibody once every two days. Experimental schema is presented. (b and c) Tumor volume of control (black line, n=5) mice, mice treated with only anti-BAG2 antibody 3B10 (green line, n=5), mice treated with only anti-PD-L1 antibody (blue line, n=5), and mice treated with both 3B10 and anti-PD-L1 antibody (red line, n=5). Tumor growth was monitored and tumor volumes were measured with electronic calipers at Days 12, 14, 16, 18, 20, 22, and 24. On day 25, mice were sacrificed. (b) The tumor volumes of individual mice within groups. (c) Average tumor growth of the four treatment groups. (d) Profiles of CD3+/CD8+ T cells in the EMT6 tumor microenvironment (TME) of all groups. Flow cytometry data are the average from two independent experiments. t-TEST: all data are presented as the mean±SEM (standard error of mean). * $p<0.05$, *** $p<0.001$ (vs. control mouse IgG2a administered group)

As shown in FIG. 4a, 12 days after tumor inoculation, EMT6 tumor-bearing BALB/c mice were randomized by tumor size before drug administration was carried out. Mice were treated with anti-BAG2 antibody 3B10 on days 12 after tumor cell injection. Subsequently, on day 14, mice received a single injection of anti-PD-L1 antibody.

Figure 4B:
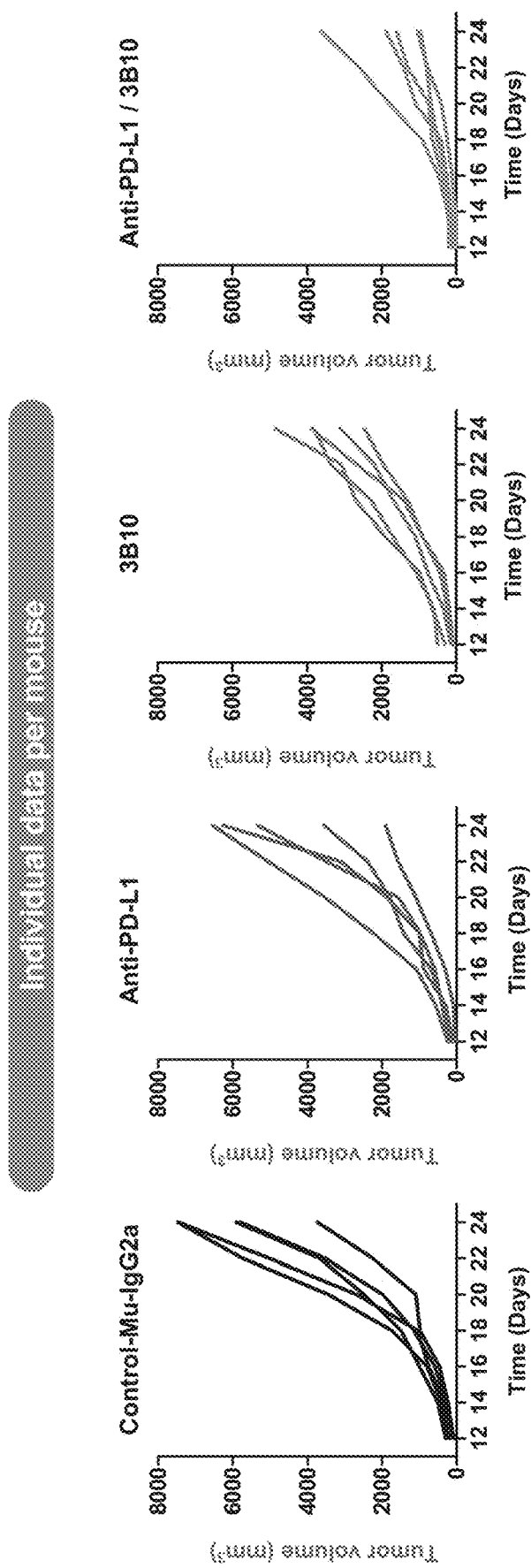
Figure 4C:
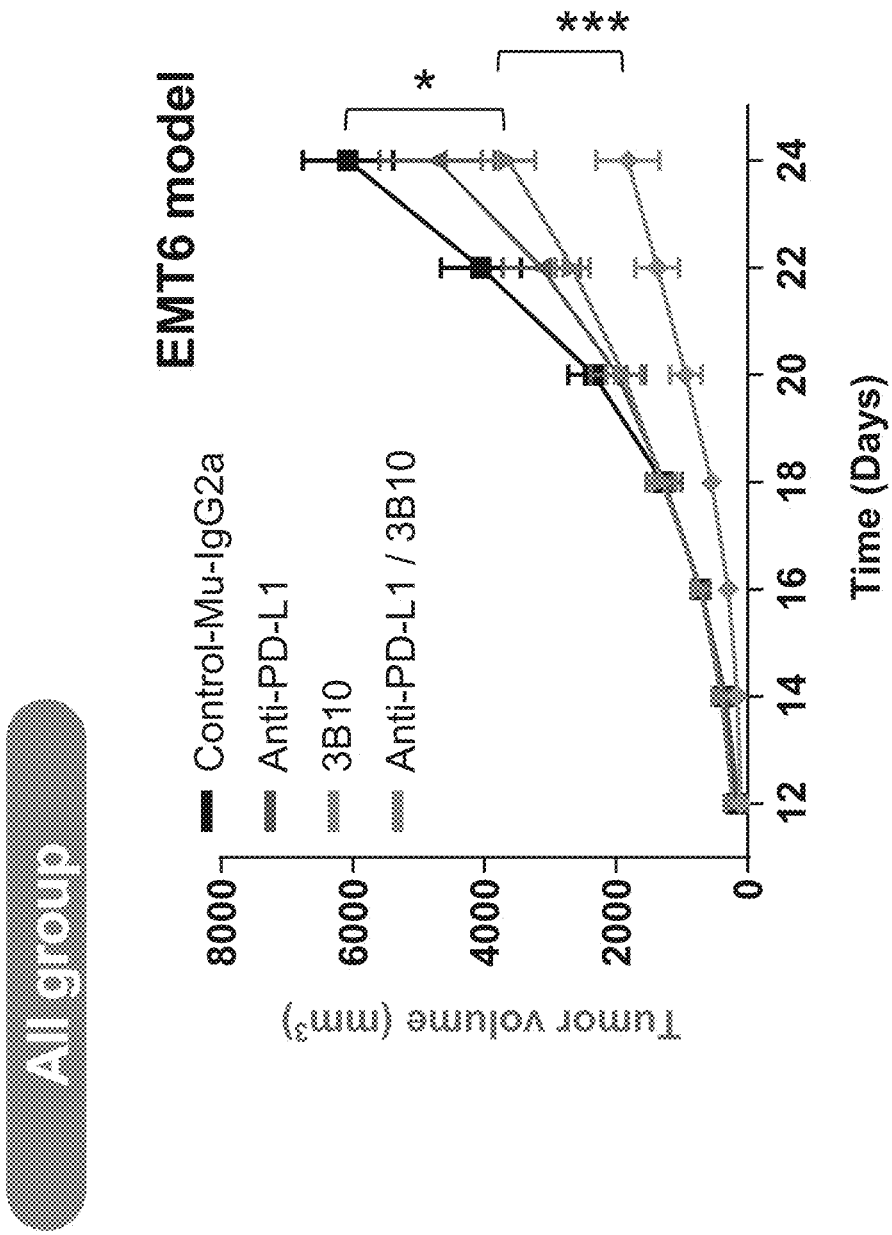

As shown in FIGS. 4b and 4c, at the 24th day, the tumor volume of the anti-PD-L1 antibody administered group, the anti-BAG2 antibody 3B10 administered group, and the combination of anti-PD-L1 antibody and 3B10 administered group was decreased by about 20.2%, about 39.8%, and about 70.1%, as compared with the tumor volume of the isotype control group, respectively. Treatment with anti- PD-1 antibody had a marginal effect on tumor growth, but treatment together with 3B10 significantly inhibited tumor growth. Treatment with the combination of anti-PD-L1 antibody and 3B10 inhibited tumor growth to a greater extent than either agent alone.

Figure 4D:
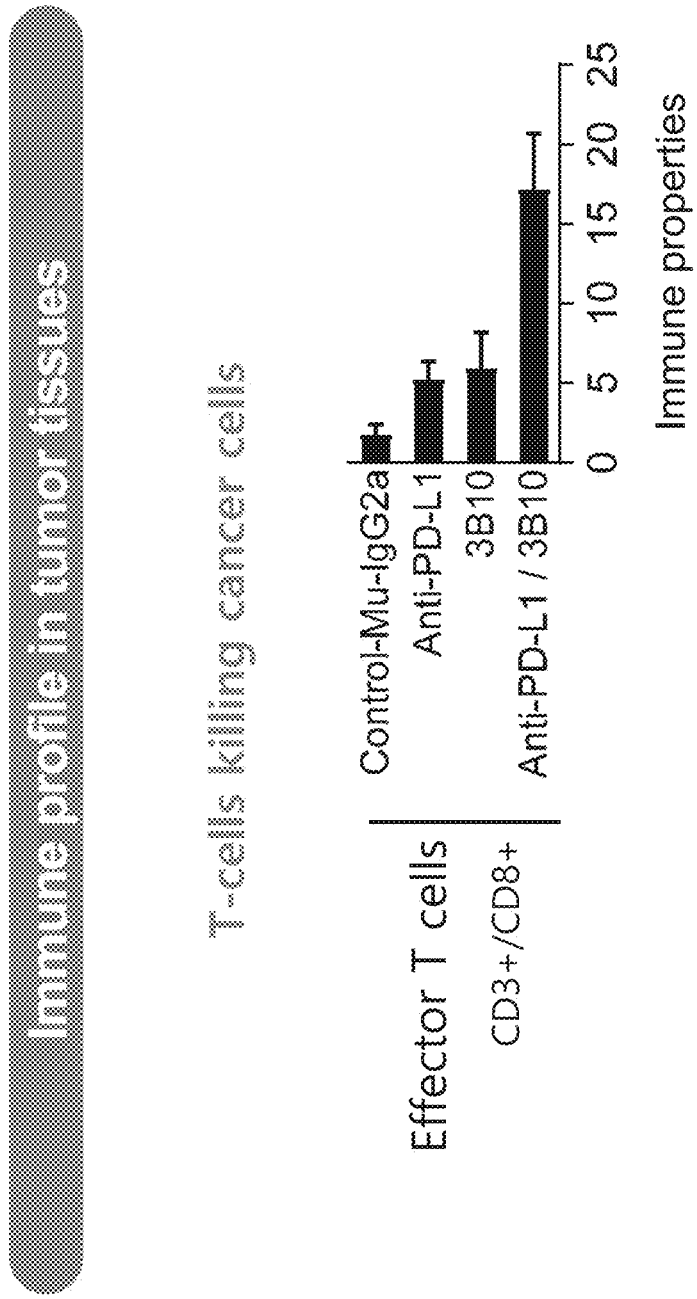

As shown in FIG. 4d, tumor-specific CD3+/CD8+ T-cells (Effector memory cells in killing cancer cells) of the anti-PD-L1 antibody administered group, the anti-BAG2 antibody 3B10 administered group, and the combination of anti-PD-L1 antibody and 3B10 administered group was increased by about 2.4 times, 2.8 times, and 8.2 times, as compared with the amount of CD3+/CD8+ T-cells of the isotype control group, respectively. Treatment with the combination of anti-PD-L1 antibody and 3B10 activated tumor-specific CD3+/CD8+ T-cells to a greater extent than either agent alone. The activation may be direct or indirect, i.e., an inhibition of suppressor cells.

2.2. Results of Treating Lung Cancer in Mouse Model

The results show the following:

Combined therapies of anti-BAG2 antibody and immune checkpoint inhibitors have a synergistic antitumor activity in mouse lung cancer model.

Figure 5A:
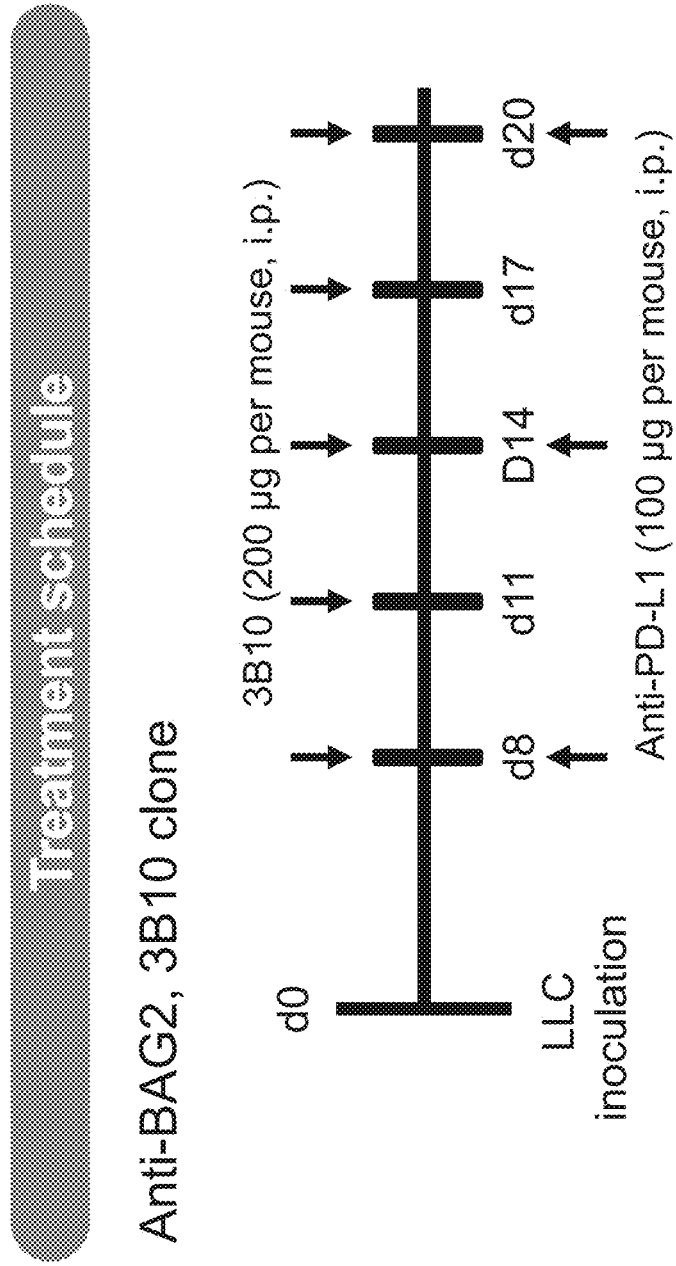
FIGS. 5A-5D show therapeutic efficacy of anti-BAG2 antibody in combination with anti-PD-L1 antibody in a lung cancer model. (a) C57BL/6 mice were injected with $5 \times 10^5$ LLC cells. About eight days later, when average tumor size reached about 60-80 mm³, mice were sorted into groups (n=5) so that the average tumor sizes of all groups were similar, and treatment by i.p. injections was initiated. On days 8 after tumor cell injection, some of the mice were injected i.p. with anti-BAG2 antibody 3B10 (200 μg per mouse), an anti-PD-L1 antibody (100 μg per mouse), a combination of anti-PD-L1 antibody and 3B10, or isotype control antibody once every three days until study completion. Experimental schema is presented. (b and c) Tumor volume of control (black line, n=5) mice, mice treated with only anti-BAG2 antibody 3B10 (green line, n=5), mice treated with only anti-PD-L1 antibody (blue line, n=5), and mice treated with both anti-BAG2 and anti-PD-L1 antibody (red line, n=5). Tumor growth was monitored and tumor volumes were measured with electronic calipers at Days 8, 11, 14, 17, and 20. On day 20, mice were sacrificed. (b) The tumor volumes of individual mice within groups. (c) Average tumor growth of the four treatment groups. (d) Profiles of CD3+/CD8+ T cells in the LLC tumor microenvironment (TME) of all group. Flow cytometry data are the average from two independent experiments. t-TEST: all data are presented as the mean±SEM (standard error of mean). * $p<0.05$, ** $p<0.01$ (vs. control mouse IgG2a administered group).

As shown in FIG. 5a, LLC tumor-bearing C57BL/6 mice were initially treated with anti-BAG2 antibody 3B10 on days 8 after tumor cell injection. Subsequently, on day 14, mice received a single injection of anti-PD-L1 antibody.

Figure 5B:
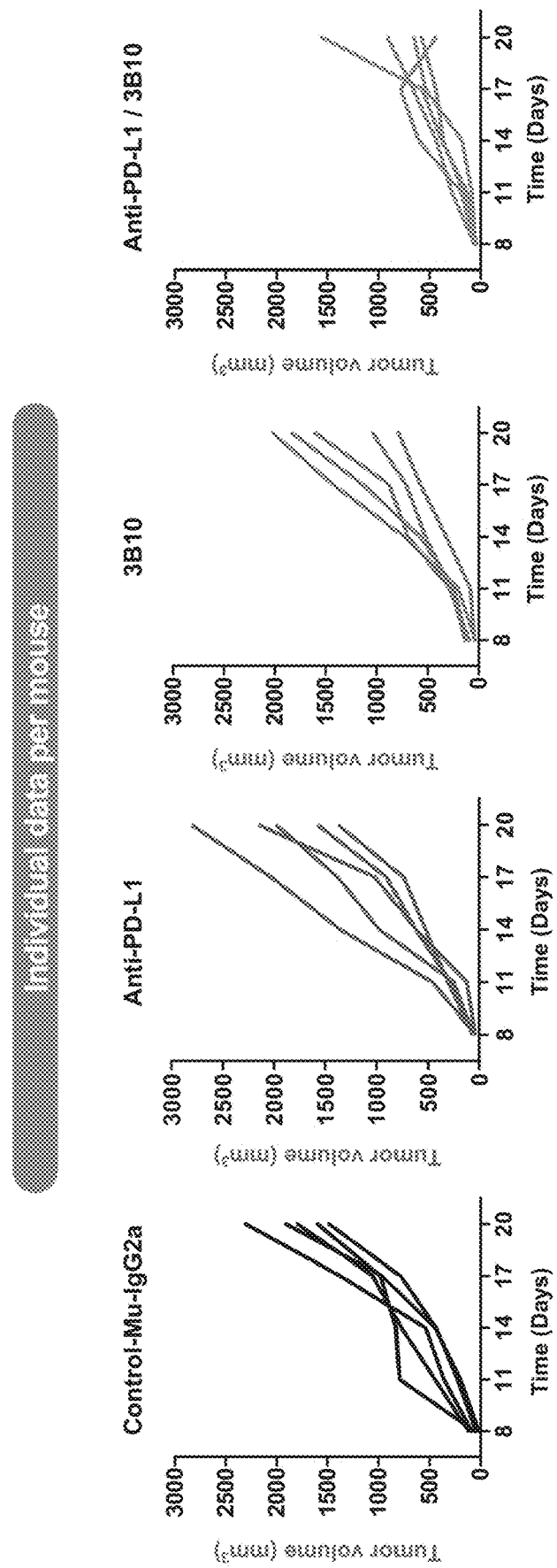
Figure 5C:
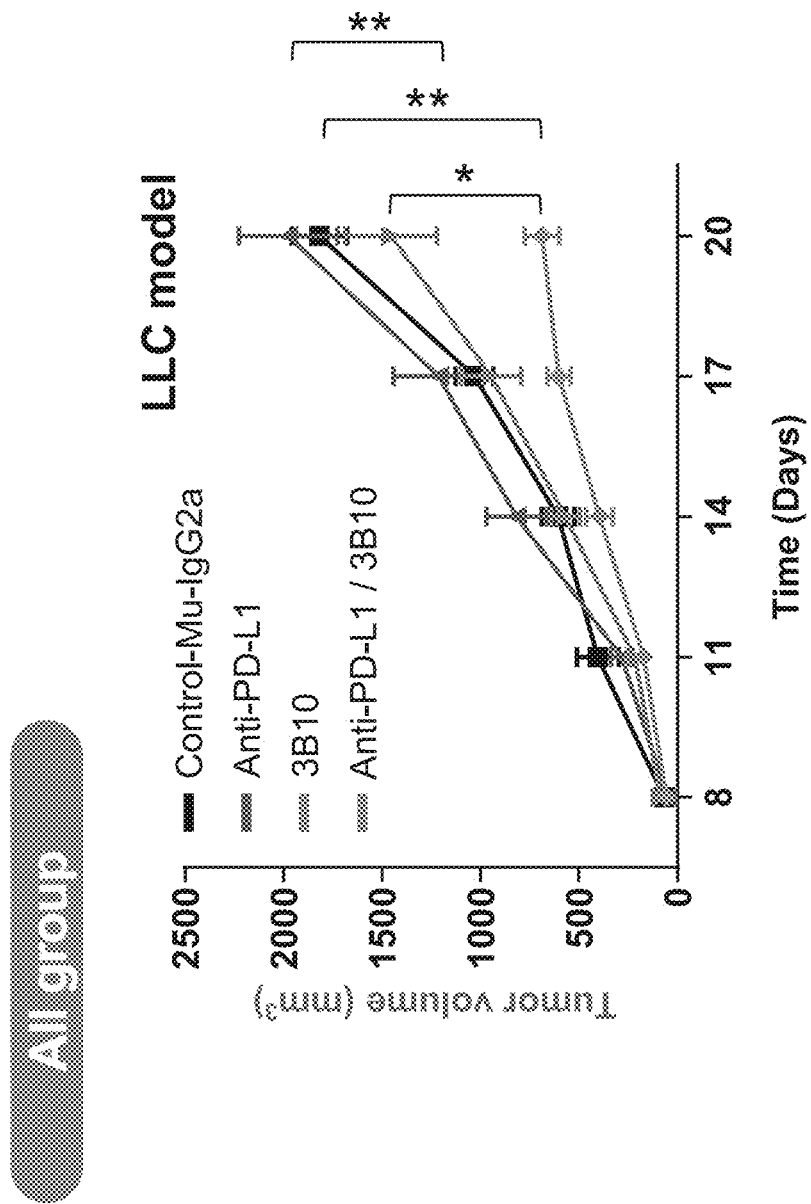

As shown in FIGS. 5b and 5c, at the 20th day, the tumor volume of the anti-PD-L1 antibody administered group, the anti-BAG2 antibody 3B10 administered group, and the combination of anti-PD-L1 antibody and 3B10 administered group was decreased by about 8.7%, about 17.8%, and about 62.2%, as compared with the tumor volume of the isotype control group, respectively. Treatment with the combination of anti-PD-L1 antibody and 3B10 inhibited tumor growth to a greater extent than either agent alone.

Figure 5D:
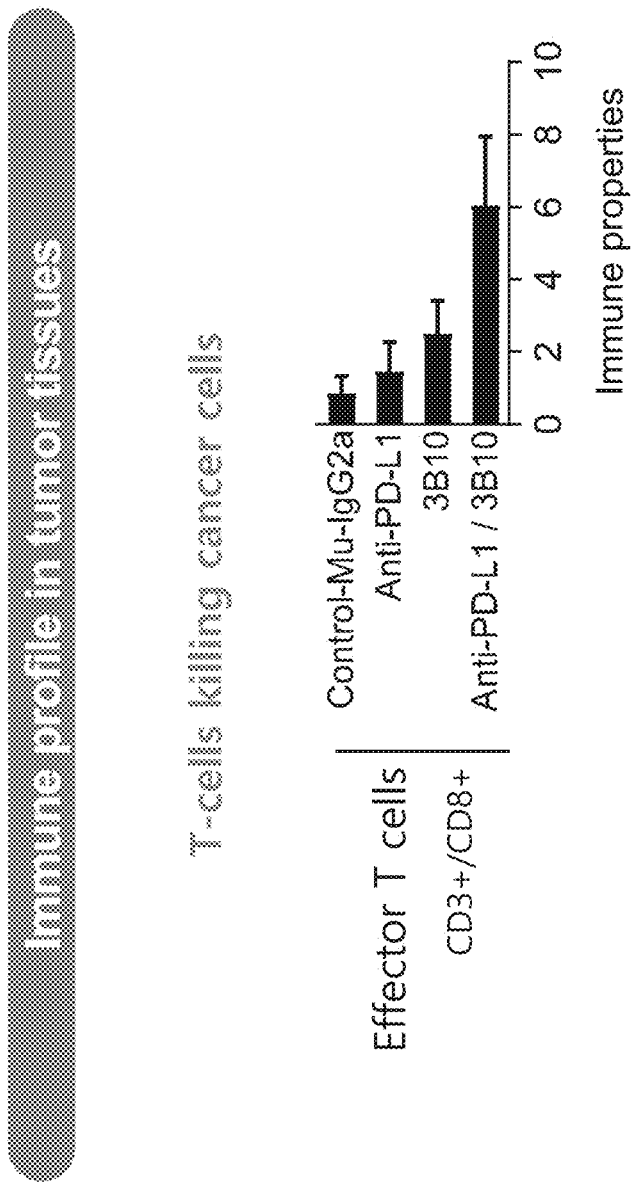

As shown in FIG. 5d, tumor-specific CD3+/CD8+ T-cells (Effector memory cells in killing cancer cells) of the anti-PD-L1 antibody administered group, the anti-BAG2 antibody 3B10 administered group, and the combination of anti-PD-L1 antibody and 3B10 administered group was increased by about 1.3 times, 2.8 times, and 6.6 times, as compared with the CD3+/CD8+ T-cell levels of the isotype control group, respectively. Treatment with the combination of anti-PD-L1 antibody and 3B10 activated tumor-specific CD3+/CD8+ T-cells to a greater extent than either agent alone. The activation may be direct or indirect, i.e., an inhibition of suppressor cells.

2.3. Results of Treating Melanoma in Mouse Model

The results show the following:

Anti-BAG2 antibody has an antitumor activity in mouse melanoma metastasis to lung model.

Combined therapies of anti-BAG2 antibody and anti-PD-L1 antibody have a synergistic antitumor activity in mouse melanoma metastasis to lung model.

Figure 6A:
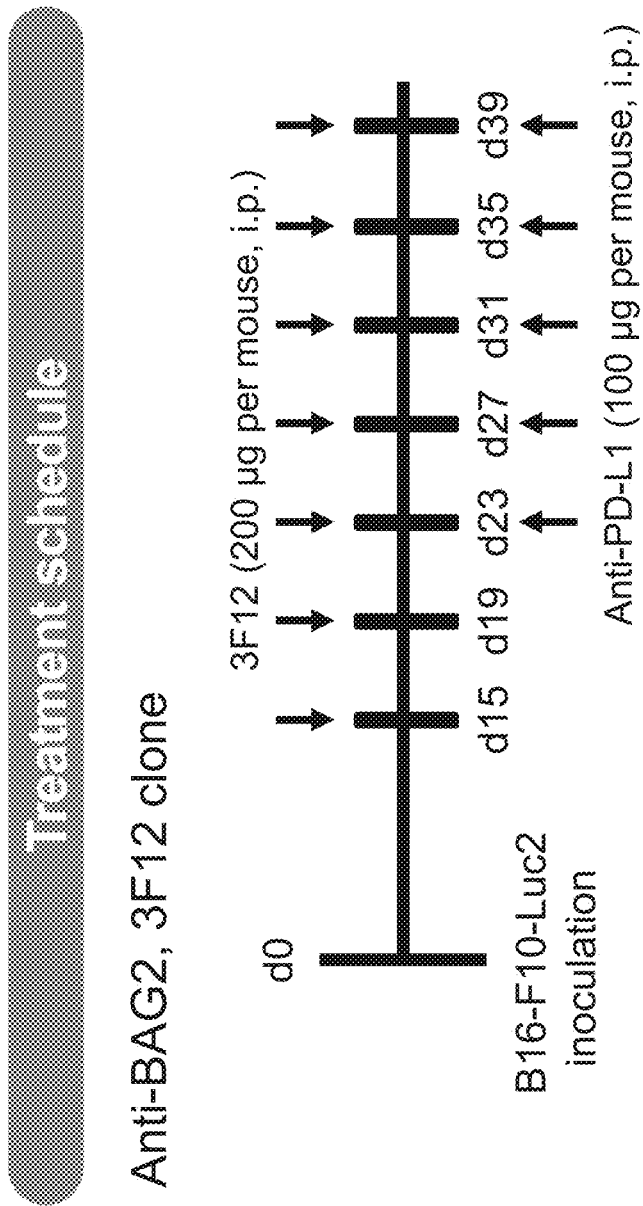
FIGS. 6A-6C show therapeutic efficacy of anti-BAG2 antibody in combination with anti-PD-L1 antibody in a melanoma metastasis to lung model. (a) C57BL/6 mice were intravenously injected with $2\times10^5$ B16-F10-Luc2 cells. When performing BLI, mice received intraperitoneal (i.p.) injections of D-luciferin and their BLI signals served as background. The growth of melanoma metastasis to lung tumor was monitored by BLI signals on days 14, 20, 26, 32, and 38, and mice were sorted into groups (n=4) so that the average BLI signals of four groups were similar. On days 15 after tumor cell injection, some of the mice were injected intraperitoneally (i.p.) with anti-BAG2 antibody 3F12 (200 μg per mouse) or isotype control antibody once every four days. On day 23, some mice received a single injection of anti-PD-L1 (100 μg per mouse, i.p.) or isotype control antibody once every four days until study completion. On day 39, mice were sacrificed. Experimental schema is presented. (b) On days 38, representative BLI signals of control mice (n=4), mice treated with only anti-PD-L1 antibody (n=4), mice treated with only anti-BAG2 antibody 3F12 (n=4), and mice treated with both anti-BAG2 antibody 3F12 and anti-PD-L1 antibody (n=4). (c) Quantification of the BLI signal of tumors in the four treatment groups. t-TEST: all data are presented as the mean±SEM (standard error of mean). * $p<0.05$,  $p<0.01$, * $p<0.001$ (vs. control mouse IgG2a administered group).

As shown in FIG. 6a, B16-F10-Luc2 tumor-bearing C57BL/6 mice were initially treated with anti-BAG2 antibody 3F12 on days 15 after tumor cell intravenous injection. Subsequently, on day 23, mice received a single injection of anti-PD-L1 antibody.

Figure 6C:
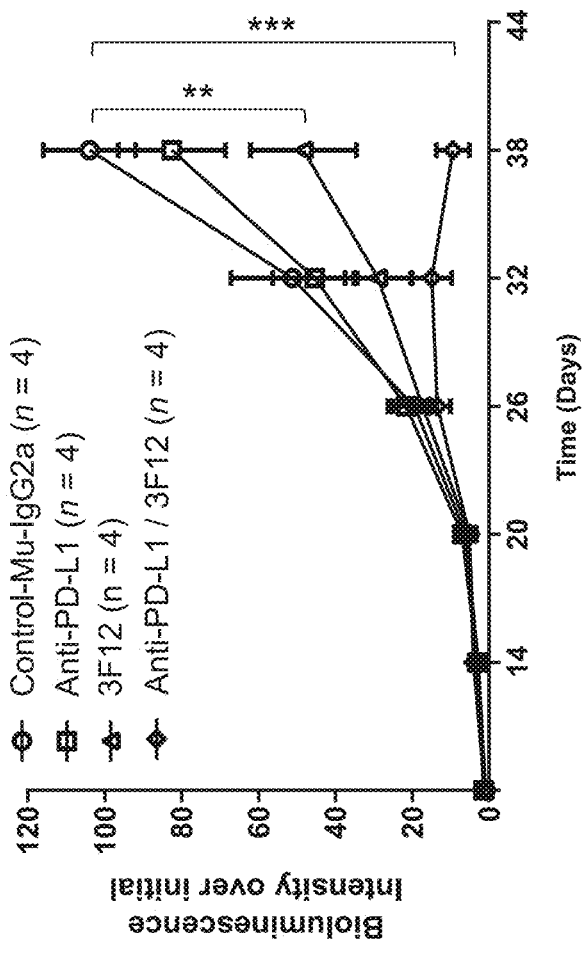
Figure 6B:
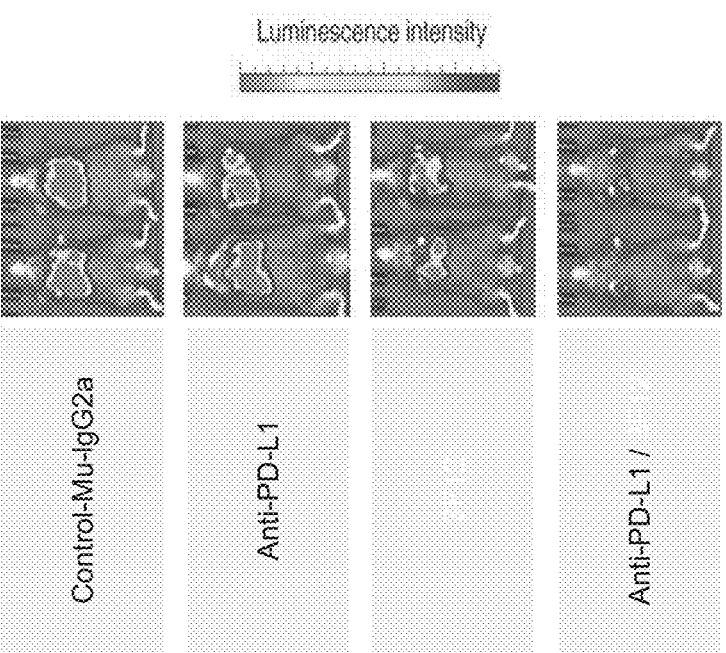

As shown in FIGS. 6b and 6c, at the 38th day, the tumor volume of the anti-PD-L1 antibody administered group, the anti-BAG2 antibody 3F12 administered group, and the combination of anti-PD-L1 antibody and 3F12 administered group was decreased by about 19%, about 54%, and about 92%, as compared with the BLI signals of the isotype control group, respectively. Single treatment with anti-PD-1 antibody had a marginal effect on melanoma tumor growth in lung, but anti-BAG2 antibody 3F12 significantly inhibited melanoma tumor growth in lung. Treatment with the combination of anti-PD-L1 antibody and 3F12 inhibited tumor growth to a greater extent than either agent alone.

2.4. Treating Colorectal Cancer

Background

Microsatellite instability (MSI) in high colorectal cancers (CRCs) have a deficiency in mismatch repair (MMR) and increased levels of PD-L1, LAG-3, and IDO, and respond positively to anti-programmed death (PD) therapy. MSI low or microsatellite stable (MSS) CRCs that make up majority of tumors in clinical practice have not seen any benefit with PD-1 inhibition. MSS CRC have higher proportion of KRAS oncogenic mutations as compared to MSI CRC. Combinatorial effect of anti-BAG2 antibody with anti-PD-1 agent was studied in syngeneic models of C57BL/6 (MC38; KRASwt, MSI) and BALB/c (CT26; KRASmut, MSS) mice.

2.4.1. Results of Treating Colorectal Cancer MSI-High Type in Mouse Model

The results show the following:

Anti-BAG2 antibody alone has an antitumor activity in mouse colorectal cancer model with MSI-high type.

Combined therapies of anti-BAG2 antibody and anti-PD-1 antibody have a synergistic antitumor activity in mouse CRC model.

Figure 7A:
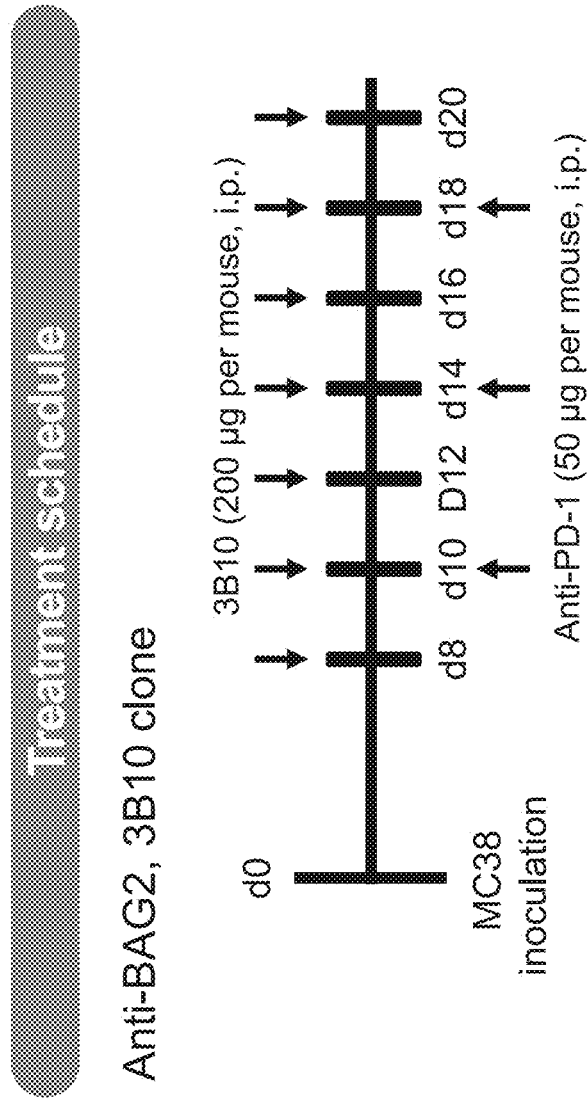
FIGS. 7A-7D show therapeutic efficacy of anti-BAG2 antibody in combination with anti-PD-1 antibody in a colorectal cancer model. (a) C57BL/6 mice were injected with $5\times10^5$ MC38 cells. About eight days later, when average tumor size reached about 30 mm³, mice were sorted into groups (n=6) so that the average tumor sizes of all groups were similar, and treatment by i.p. injections was initiated. On days 8 after tumor cell injection, some of the mice were treated with anti-BAG2 antibody 3B10 (200 μg per mouse), an anti-PD-1 antibody (50 μg per mouse), a combination of anti-PD-1 antibody and 3B10, or isotype control antibody once every four days until study completion. Experimental schema is presented. (b and c) Tumor volume of control (black line, n=6) mice, mice treated with only anti-BAG2 antibody 3B10 (green line, n=6), mice treated with only anti-PD-1 antibody (blue line, n=6), and mice treated with both anti-BAG2 and anti-PD-1 antibody (red line, n=6). Tumor growth was monitored and tumor volumes were measured with electronic calipers at Days 8, 10, 12, 14, 16, 18, and 20. On day 20, mice were sacrificed. (b) The tumor volumes of individual mice within groups. (c) Average tumor growth of the four treatment groups. (d) Profiles of CD3+/CD8+ T cells in the MC38 tumor microenvironment (TME) of all group. Flow cytometry data are the average from two independent experiments. t-TEST: all data are presented as the mean±SEM (standard error of mean). * $p<0.05$,  $p<0.01$, * $p<0.001$ (vs. control mouse IgG2a administered group).

As shown in FIG. 7a, MC38 tumor-bearing C57BL/6 mice were initially treated with anti-BAG2 antibody 3B10 on days 8 after tumor cell injection. Subsequently, on day 10, mice received a single injection of anti-PD-1 antibody.

Figure 7B:
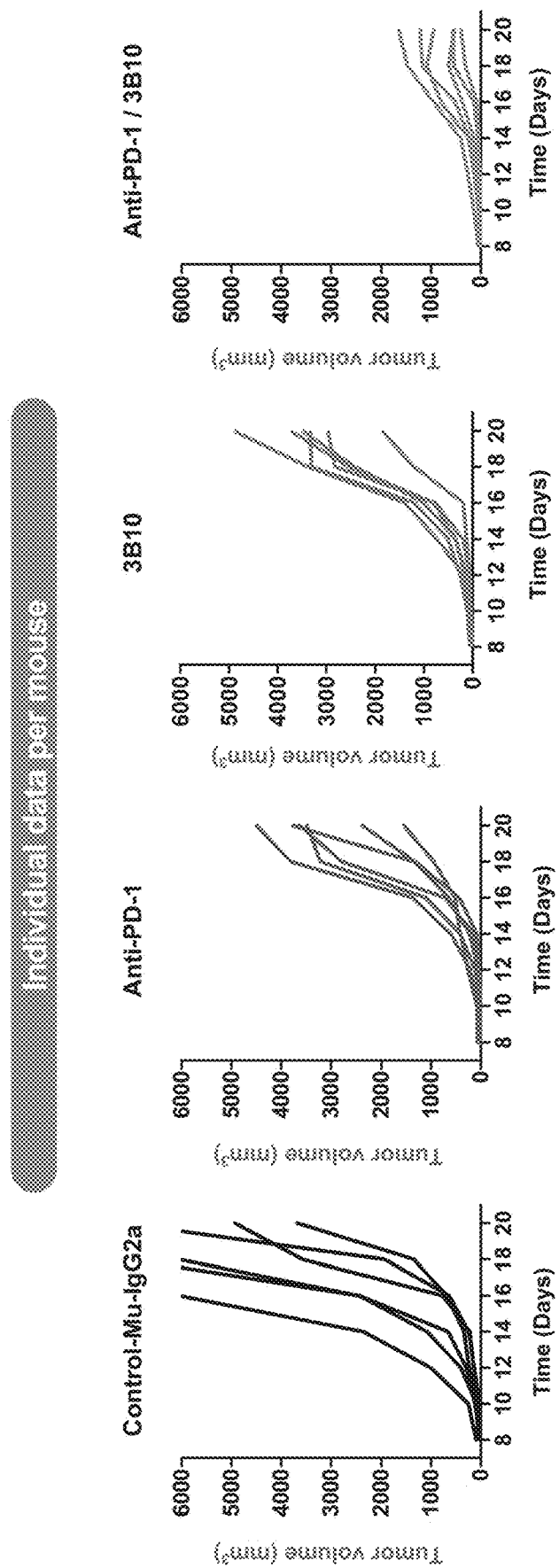
Figure 7C:
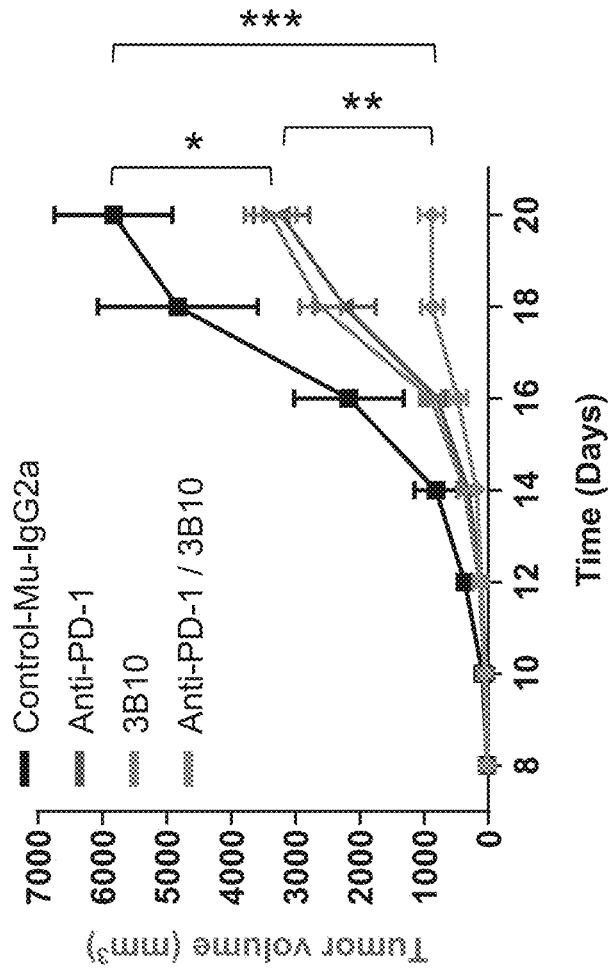

As shown in FIGS. 7b and 7c, at the 20th day, the tumor volume of the anti-PD-1 antibody administered group, the anti-BAG2 antibody 3B10 administered group, and the combination of anti-PD-1 antibody and 3B10 administered group was decreased by about 43%, about 40.8%, and about 86.8%, as compared with the tumor volume of the isotype control group, respectively. Single treatment with anti-PD-1 antibody or anti-BAG2 antibody 3B10 significantly inhibited tumor growth. Treatment with the combination of anti-PD-1 antibody and 3B10 inhibited tumor growth to a greater extent than either agent alone.

Figure 7D:
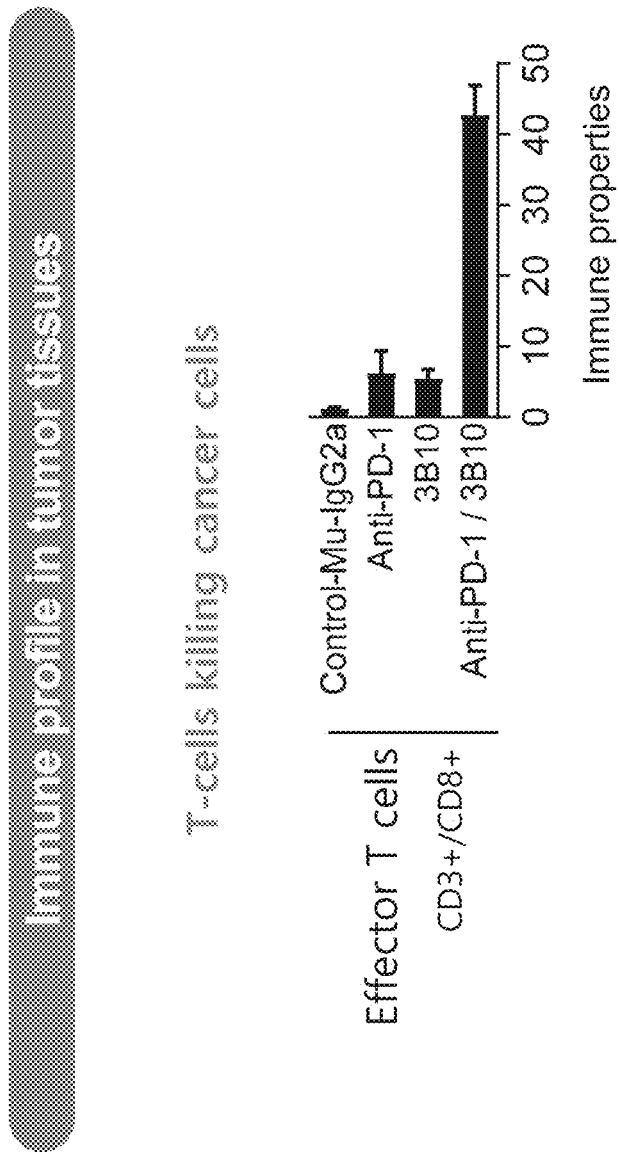

As shown in FIG. 7d, tumor-specific CD3+/CD8+ T-cells (Effector memory cells in killing cancer cells) of the anti-PD-1 antibody administered group, the anti-BAG2 antibody 3B10 administered group, and the combination of anti-PD-1 antibody and 3B10 administered group was increased by about 4.4 times, 3.9 times, and 36.2 times, as compared with the CD3+/CD8+ T-cells levels of the isotype control group, respectively. Treatment with the combination of anti-PD-1 antibody and 3B10 activated tumor-specific CD3+/CD8+ T-cells to a greater extent than either agent alone. The activation may be direct or indirect, i.e., an inhibition of suppressor cells.

2.4.2. Results of Treating Colorectal Cancer MSS Type in Mouse Model

The results show the following:

Anti-BAG2 antibody alone has an antitumor activity in mouse MSS type colorectal cancer model.

Combined therapies of anti-BAG2 antibody and anti-PD-L1 antibody have a synergistic antitumor activity in mouse MSS type CRC model.

Figure 8A:
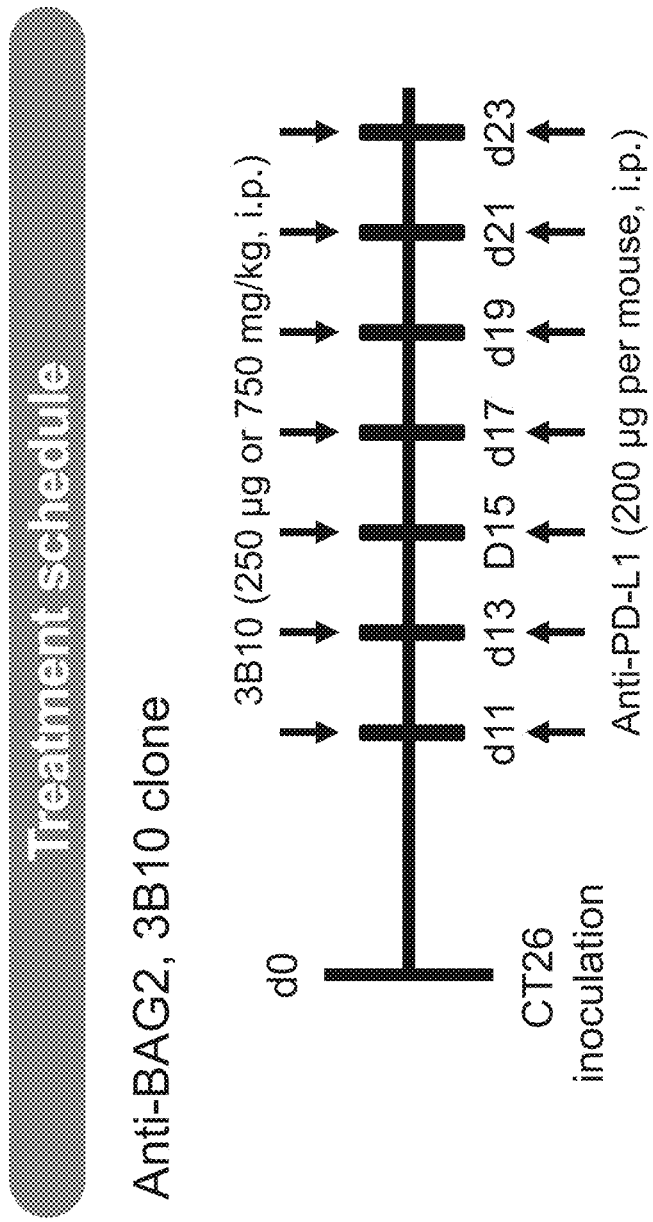
FIGS. 8A-8D show therapeutic efficacy of anti-BAG2 antibody in combination with anti-PD-L1 antibody in a lung cancer model. (a) BALB/c mice were injected with $3\times10^5$ CT26 cells. About 11 days later, when average tumor size reached about 70 mm³, mice were sorted into groups (n=7) so that the average tumor sizes of all groups were similar, and treatment by i.p. injections was initiated. On days 11 after tumor cell injection, some of the mice were treated with anti-BAG2 antibody 3B10 (250 μg or 750 μg per mouse), an anti-PD-L1 antibody (200 μg per mouse), a combination of anti-PD-L1 antibody and 3B10 (250 μg or 750 μg per mouse), or isotype control antibody once every two days until study completion. Experimental schema is presented. (b and c) Tumor volume of control (black line, n=7) mice, mice treated with only 3B10 (250 μg, green line, n=7), mice treated with only 3B10 (750 μg, brown line, n=7), mice treated with only anti-PD-L1 antibody (blue line, n=7), mice treated with both 3B10 (250 μg) and anti-PD-L1 antibody (red line, n=7), and mice treated with both 3B10 (750 μg) and anti-PD-L1 antibody (purple line, n=7). Tumor growth was monitored and tumor volumes were measured with electronic calipers at Days 11, 13, 15, 17, 19, 21, and 23. On day 20, mice were sacrificed. (b) The tumor volumes of individual mice within groups. (c) Average tumor growth of the four treatment groups. (d) Profiles of CD3+/CD8+ T cells in the MC38 tumor microenvironment (TME) of all group. Flow cytometry data are the average from two independent experiments. t-TEST: all data are presented as the mean±SEM (standard error of mean). * $p<0.05$, *** $p<0.001$ (vs. control mouse IgG2a administered group).

As shown in FIG. 8a, CT26 tumor-bearing BALB/c mice were treated with 250 µg (low dose) or 750 µg (high dose)/mouse of anti-BAG2 antibody 3B10, an anti-PD-L1 antibody, a combination of 3B10 and anti-PD-L1 antibody, or a control antibody at days 11 after tumor cell injection. Mice were dosed by i.p. injection once every two days until study completion. Tumor growth was monitored and tumor volumes were measured with electronic calipers at the indicated time points.

Figure 8B:
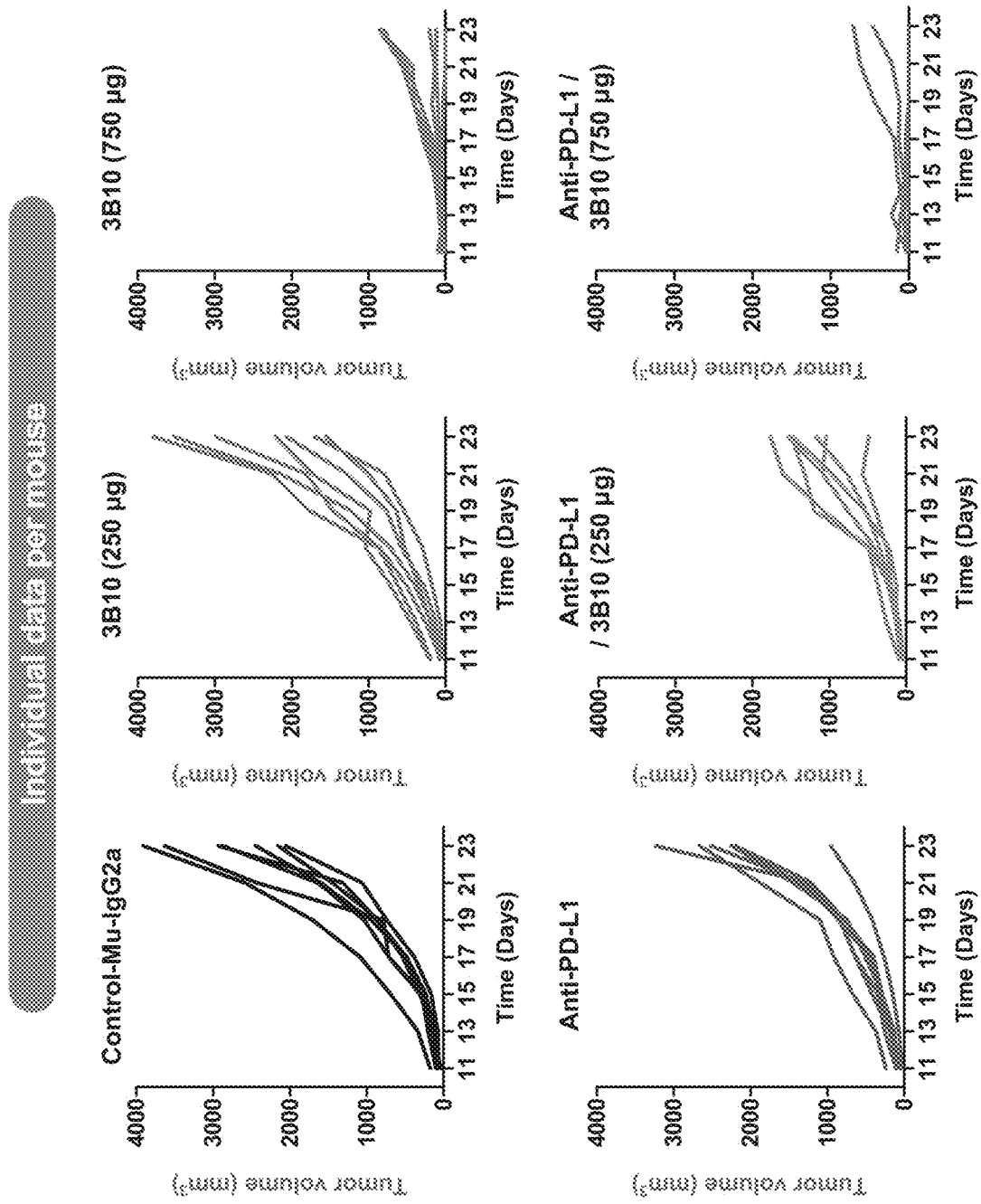
Figure 8C:
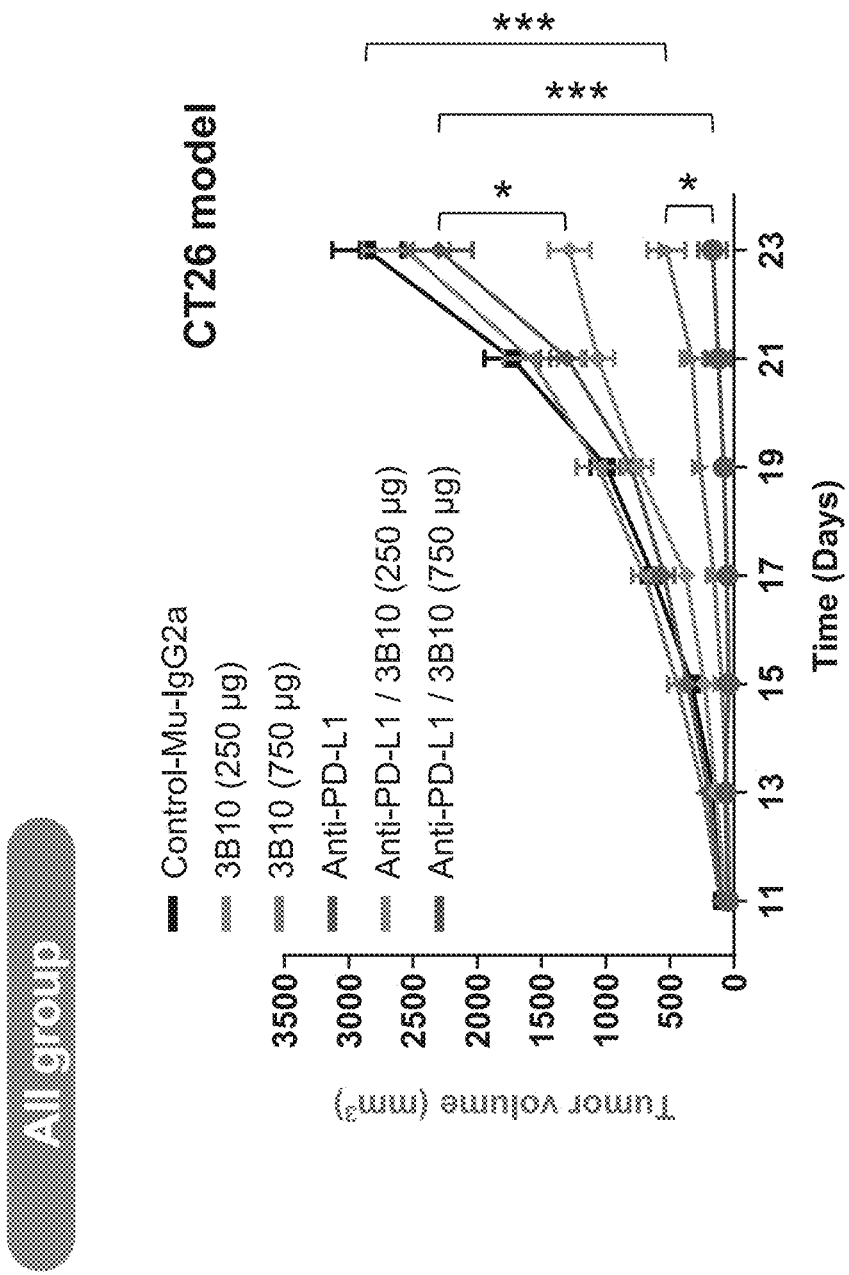

As shown in FIGS. 8b and 8c, at the 23th day, the tumor volume of the low dose of 3B10 administered group, the high dose of 3B10 administered group, the anti-PD-L1 antibody administered group, the combination of anti-PD-L1 antibody and low dose of 3B10 administered group, and the combination of anti-PD-L1 antibody and high dose of 3B10 administered group was decreased by about 9.1%, about 78.8%, about 17.4%, about 52.2%, and about 95.1%, as compared with the tumor volume of the isotype control group, respectively. Single treatment with high dose of 3B10 strongly inhibited growth of CT26 tumors. Treatment with the anti-PD-L1 antibody was much less successful at inhibiting tumor growth as a single agent. Treatment with the combination of anti-PD-L1 antibody and low dose of 3B10 inhibited tumor growth to a greater extent than either agent alone. Moreover, combined treatment with anti-PD-L1 antibody and high dose of 3B10 showed the regression of individual tumors, to undetectable levels in a majority of the treated mice.

Figure 8D:
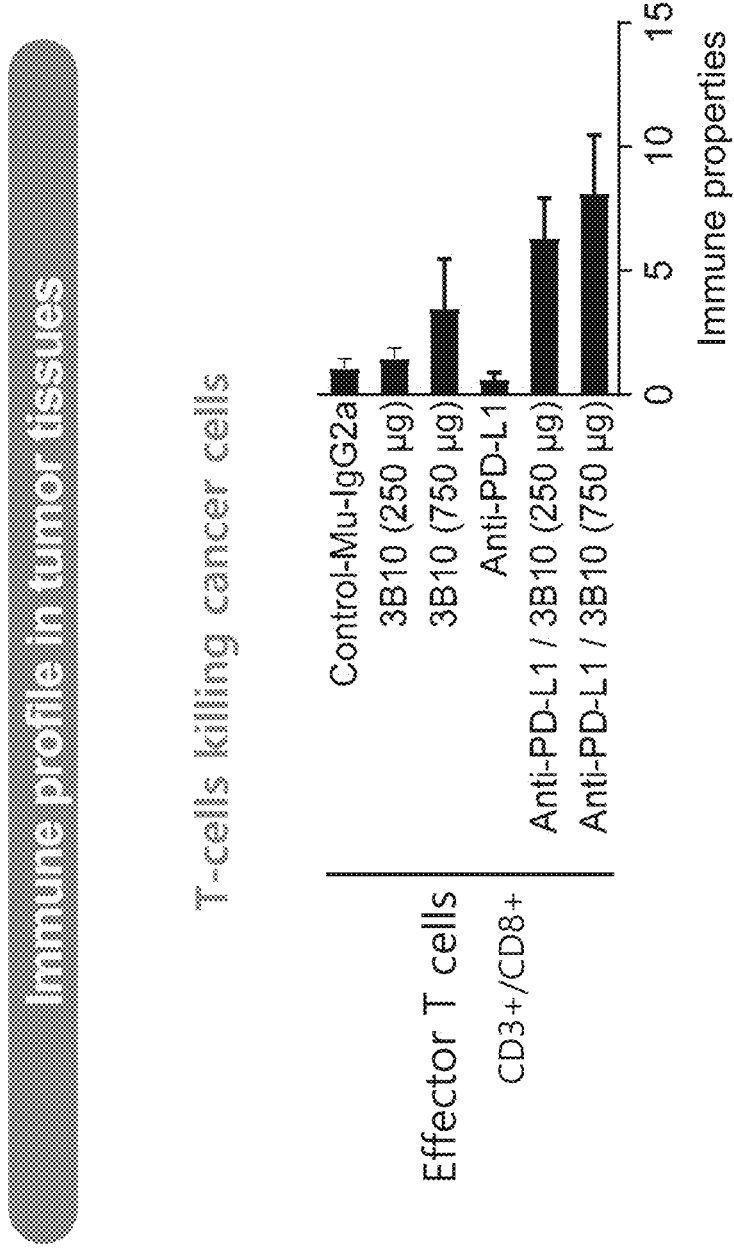

As shown in FIG. 8d, tumor-specific CD3+/CD8+ T-cells (Effector memory cells in killing cancer cells) of the low dose of 3B10 administered group, the high dose of 3B10 administered group, the anti-PD-L1 antibody administered group, the combination of anti-PD-L1 antibody and low dose of 3B10 administered group, and the combination of anti-PD-L1 antibody and high dose of 3B10 administered group was increased by about 1.4 times, 3.8 times, −1.5 times, 6.6 times, and 8.7 times, as compared with the CD3+/CD8+ T-cell level of the isotype control group, respectively. Treatment with the combination of anti-PD-L1 antibody and 3B10 activated tumor-specific CD3+/CD8+ T-cells to a greater extent than either agent alone. The activation may be direct or indirect, i.e., an inhibition of suppressor cells.

2.5. Results of Treating Pancreatic Cancer in Mouse Model

The results show the following:

Anti-BAG2 antibody alone has an antitumor activity in mouse pancreatic cancer model.

Combined therapies of anti-BAG2 antibody and immune checkpoint inhibitors (anti-PD-1 antibody and anti-CTLA4 antibody) have a synergistic antitumor activity in mouse pancreatic cancer model.

Figure 9A:
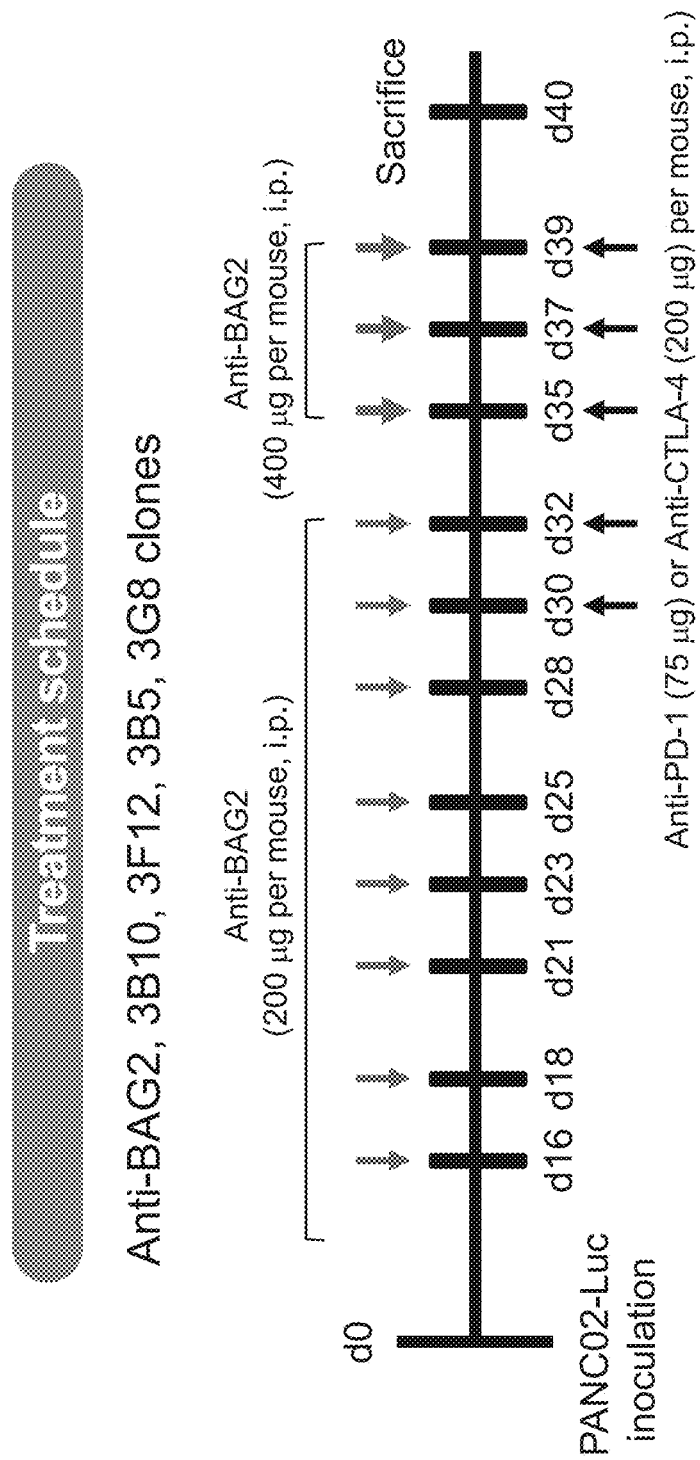
FIGS. 9A-9E show therapeutic efficacy of anti-BAG2 antibody in combination with anti-PD-1 antibody or anti-CTLA4 antibody in a pancreatic cancer model. (a) C57BL/6 mice were orthotopically injected with $2\times10^6$ PANC02-Luc cells. About 15 days later, when performing BLI, mice received intraperitoneal (i.p.) injections of D-luciferin and their BLI signals served as background. The growth of primary pancreatic tumor was monitored by BLI signals, mice were sorted into groups (n=6-7) so that the average BLI signals of fifteen groups were similar. Mice were treated with 200 μg (low dose)/mouse (from day 16 to day 32 in eight times) and 400 μg (high dose)/mouse (from day 35 to day 39 in three times) four anti-BAG2 antibodies (3B10, 3F12, 3B5, and 3G8) or an isotype control antibody, three times a week until study completion. On day 28 after implantation, mice were treated with an anti-PD-1 antibody (75 μg per mouse) or anti-CTLA4 antibody (200 μg per mouse), or an isotype control antibody, three times a week until study completion. On day 40, mice were sacrificed. Experimental schema is presented. (b) Tumor growth was monitored by IVIS imaging of the BLI signal on days 15, 27, and 39 after implantation. BLI signals of mice treated with only four anti-BAG2 antibodies (3B10, 3F12, 3B5, and 3G8) or an isotype control antibody (white bar, n=7 per group), mice additively treated with anti-PD-1 antibody (black bar, n=6 per group), and mice additively treated with an anti-CTLA4 antibody (gray bar, n=4 per group). (c) On day 40, the primary tumor weight (mg) of individual mice within groups. (d) Average metastasis to liver (left), pleural (middle) and diaphragm (right) in the fifteen treatment groups. (e) Profiles of lymphocyte-, NK-, myeloid-, stroma-cell population in the PANC02-Luc tumor microenvironment (TME) of all groups. Tumor-specific CD45+/CD11b+/Gr1−/F4/80+ macrophage, CD45+/CD11b+/Gr1+MDSC, and CD45−/CD90.2+ stroma cells Flow cytometry data are the average from two independent experiments. t-TEST: all data are presented as the mean±SEM (standard error of mean). * $p<0.05$,  $p<0.01$, * $p<0.001$ (vs. control mouse IgG2a administered group). n.s. (non-significant). Tumor-specific lymphocytes (CD3+/CD8+ T-cells and CD45+/CD3−/CD19+ B-cells); Tumor-specific NK-cells (CD45+/CD3−/CD49b+); Tumor-specific myeloid-cells (CD45+/CD11b+/Gr1−/F4/80+ macrophage, CD45+/CD11b+/Gr1+MDSC); Tumor-specific stroma cells (CD45−/CD90.2+).

As shown in FIG. 9a, PANC02-Luc tumor-bearing C57BL/6 mice were treated with 200 μg (low dose)/mouse (from day 16 to day 32) and 400 μg (high dose)/mouse (from day 35 to day 39 in three times) four anti-BAG2 antibodies (3B10, 3F12, 3B5, and 3G8) or a control antibody after tumor cell injection. Mice were dosed by i.p. injection three times a week until study completion. From day 30 to day 39, the mice received injection of anti-PD-1 antibody or anti-CTLA4 antibody. Tumor growth was monitored by IVIS imaging of the bioluminescence (BLI) signal on days 15, 27, and 39 after implantation.

Figure 9B:
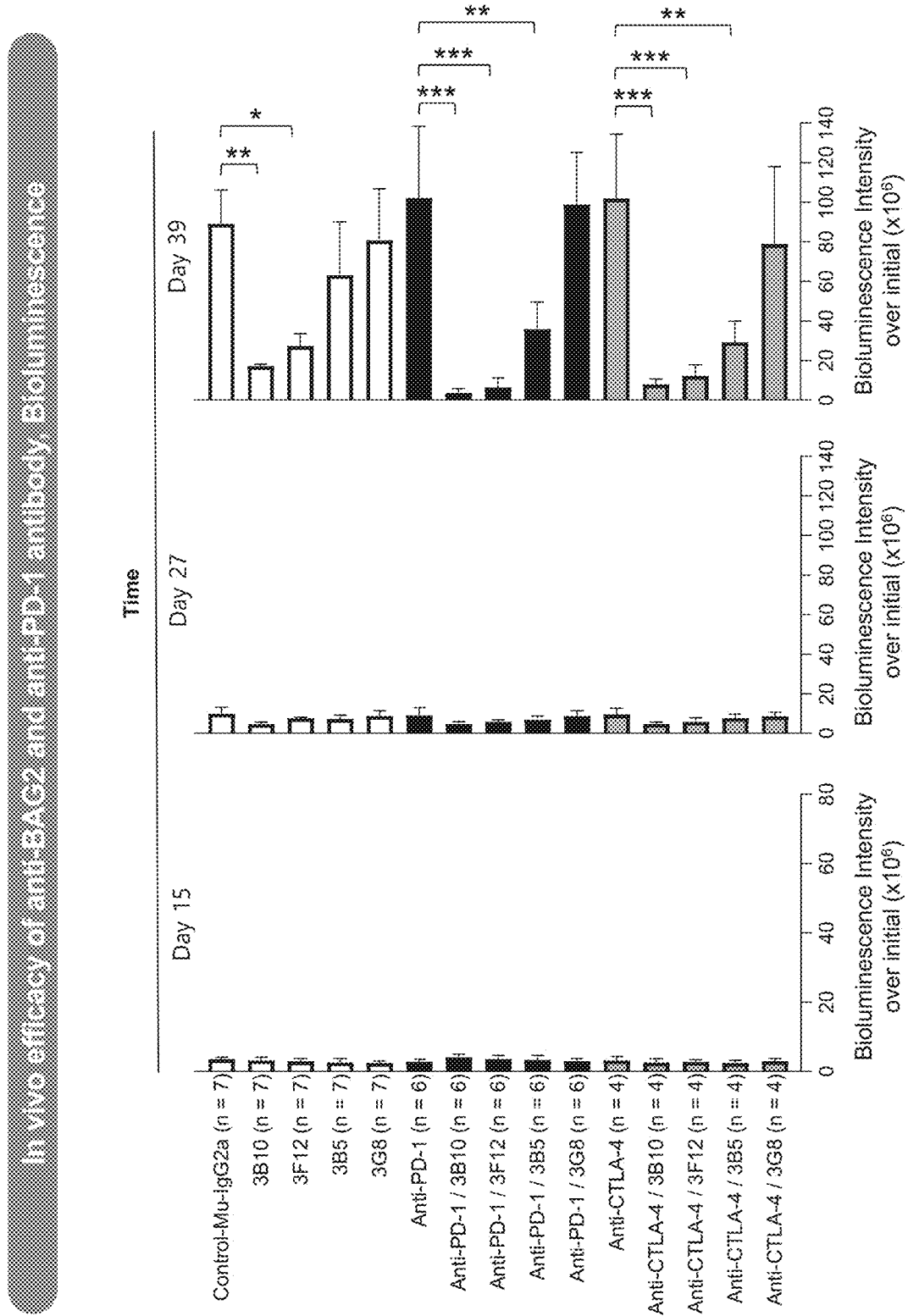

As shown in FIG. 9b, on the 40th day, the BLI signal intensity of the groups administered anti-BAG2 antibodies individually, 3B10 administered group, 3F12 administered group, 3B5 administered group, and 3G8 administered group was decreased by about 79.3%, about 68.4%, about 24.8%, and about 8.3%, as compared with the isotype control group, respectively. The BLI signal intensity of the anti-PD-1 antibody administered group, the combination of anti-PD-1 antibody and 3B10 administered group, the combination of anti-PD-1 antibody and 3F12 administered group, the combination of anti-PD-1 antibody and 3B5 administered group, and the combination of anti-PD-1 antibody and 3G8 administered group was decreased by about −14.7%, about 95.9%, about 92.8%, about 62.3%, and about −10.9%, as compared with the isotype control group, respectively. The BLI signal intensity of the only anti-CTLA4 antibody administered group, the combination of anti-CTLA4 antibody and 3B10 administered group, the combination of anti-CTLA4 antibody and 3F12 administered group, the combination of anti-CTLA4 antibody and 3B5 administered group, and the combination of anti-CTLA4 antibody and 3G8 administered group was decreased by about −14.5%, about 91.1%, about 85.3%, about 66.3%, and about 10.9%, as compared with the isotype control group, respectively.

Figure 9C:
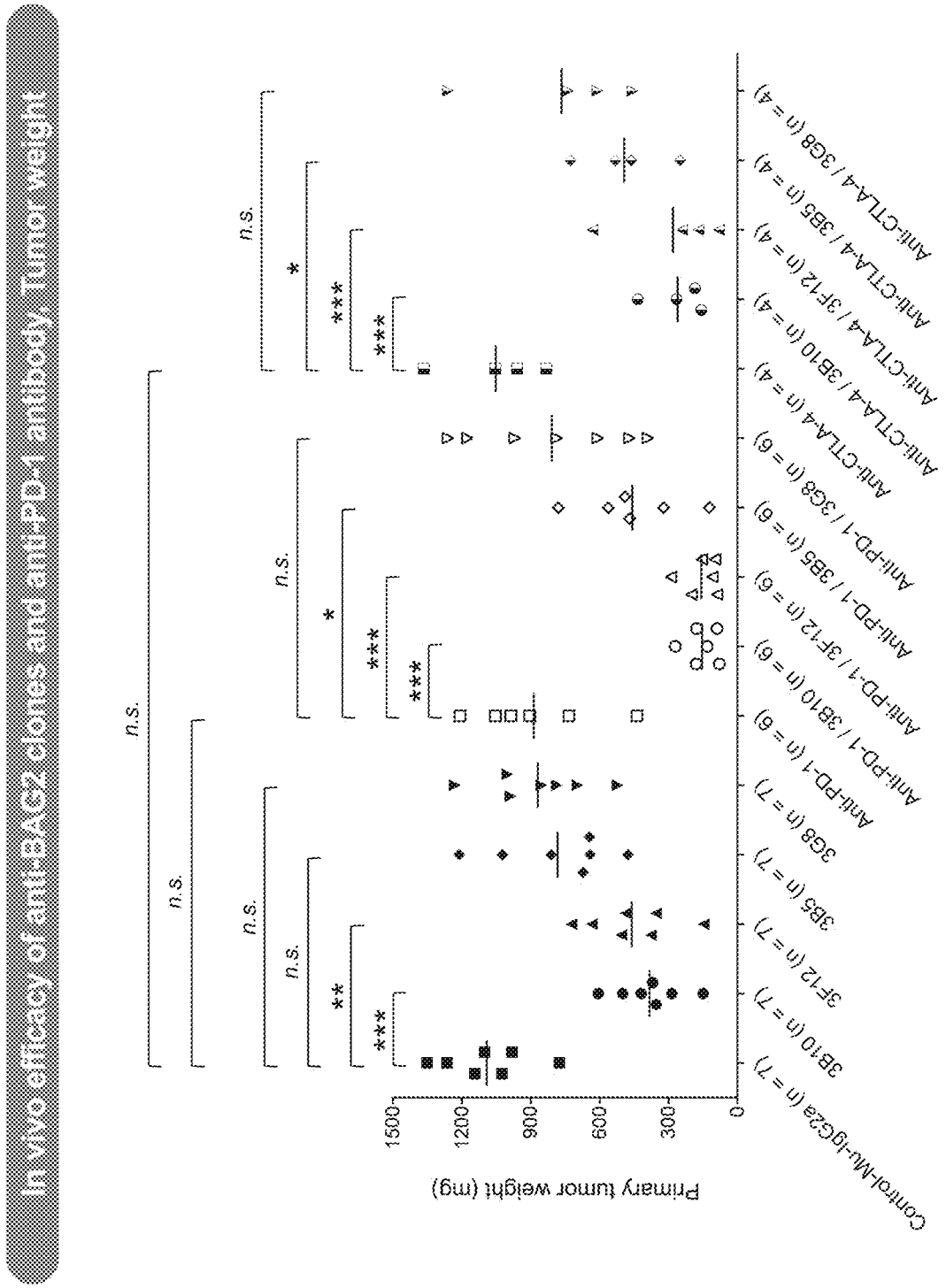

As shown in FIG. 9c, at the 40th day, the primary tumor weight of the only anti-BAG2 antibody 3B10 administered group, 3F12 administered group, 3B5 administered group, and 3G8 administered group was decreased by about 63.8%, about 56.7%, about 27.8%, and about 18.9%, as compared with the isotype control group, respectively. The BLI signal intensity of the only anti-PD-1 antibody administered group, the combination of anti-PD-1 antibody and 3B10 administered group, the combination of anti-PD-1 antibody and 3F12 administered group, the combination of anti-PD-1 antibody and 3B5 administered group, and the combination of anti-PD-1 antibody and 3G8 administered group was decreased by about 17.8%, about 85.7%, about 87.4%, about 58.1%, and about −24.8%, as compared with the isotype control group, respectively. The BLI signal intensity of the only anti-CTLA4 antibody administered group, the combination of anti-CTLA4 antibody and 3B10 administered group, the combination of anti-CTLA4 antibody and 3F12 administered group, the combination of anti-CTLA4 antibody and 3B5 administered group, and the combination of anti-CTLA4 antibody and 3G8 administered group was decreased by about 3.4%, about 76.1%, about 74.2%, about 54.8%, and about 29.7%, as compared with the isotype control group, respectively.

As shown in FIGS. 9b and 9c, single treatment with 3B10 and 3F12 strongly inhibited the BLI signal intensity and decreased the primary tumor weight of PANC02-Luc tumor-bearing mice, but 3B5 and 3G8 did not significantly inhibit the BLI signal intensity and decreased the primary tumor weight of mice. The different phenomenon in four clones may be caused by the affinity for cross-reactivity with the mouse and human.

Figure 9D:
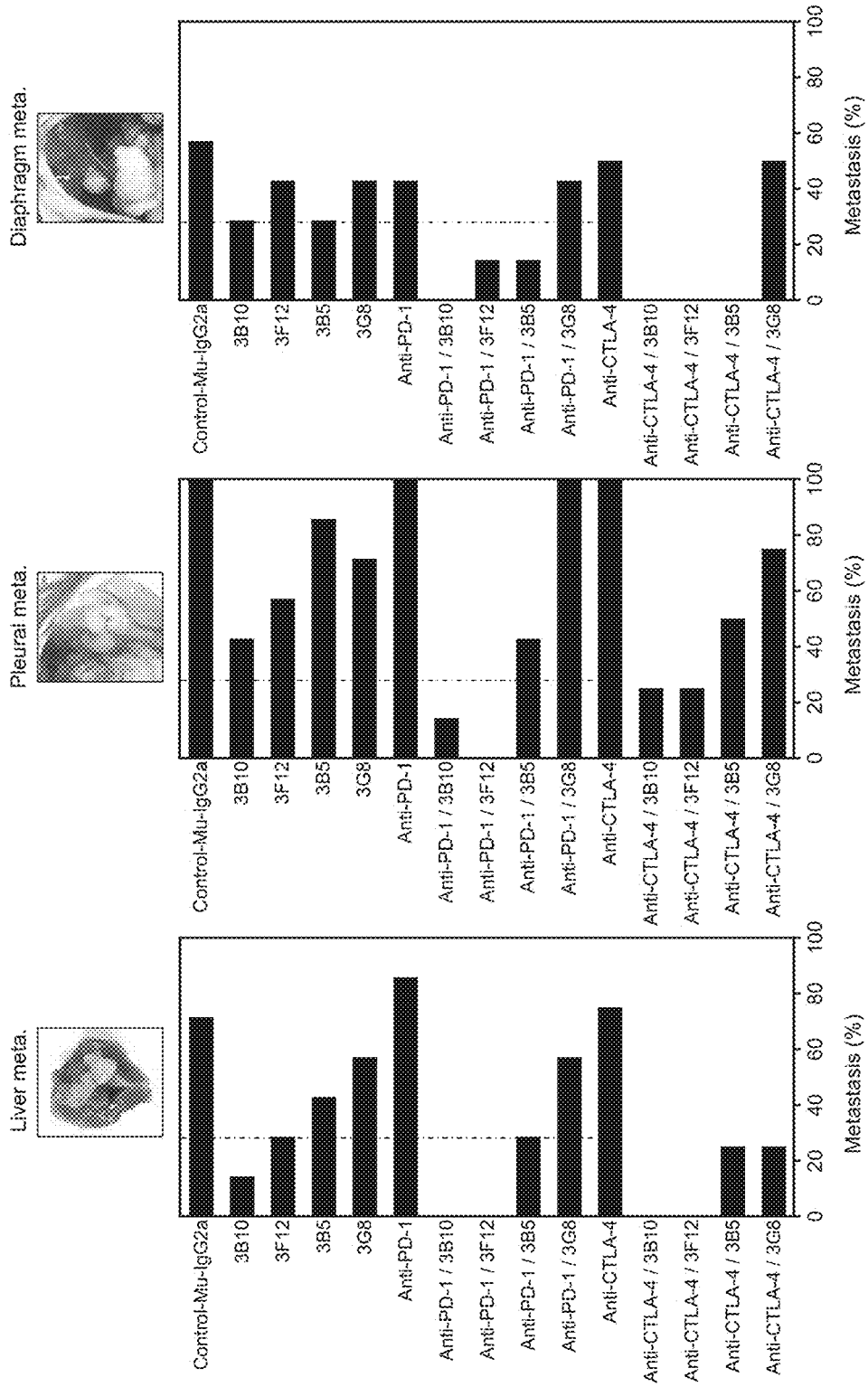

Treatment with the anti-PD-1 antibody was much less successful at inhibiting tumor growth as a single agent. Treatment with the combination of anti-BAG2 antibody (3B10, 3F12 or 3B5) and anti-PD-1 antibody or anti-CTLA4 antibody inhibited tumor growth to a greater extent than either agent alone. Moreover, combined treatment with anti-BAG2 antibody (3B10, 3F12 or 3B5) and anti-PD-L1 antibody or anti-CTLA4 antibody decreased the incidence of metastasis to liver, pleural and diaphragm as compared with either agent alone (FIG. 9d).

Figure 9E:
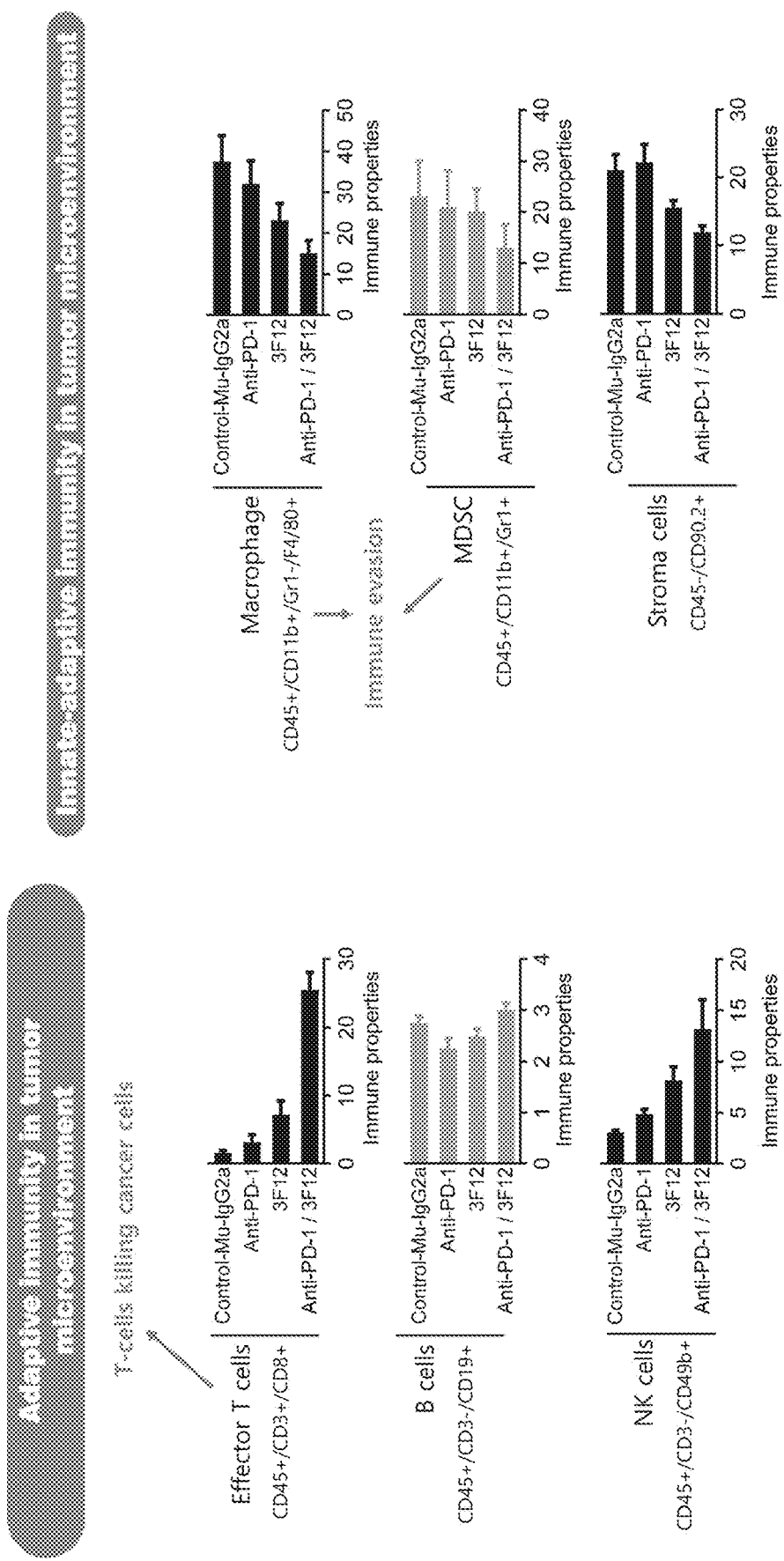

As shown in FIG. 9e, tumor-specific CD3+/CD8+ T-cells (Effector memory cells in killing cancer cells) of the anti-PD-1 antibody administered group, the 3F12 administered group, the combination of anti-PD-1 antibody and 3BF12 administered group was increased by about 1.8 times, 3.5 times, and 14.2 times, as compared with the isotype control group, respectively.

As shown in FIG. 9e, tumor-specific CD45+/CD3−/CD19+ B-cells of the anti-PD-1 antibody administered group, the 3F12 administered group, the combination of anti-PD-1 antibody and 3BF12 administered group was increased by about −1.1 times, −1.05 times, and 1.04 times, as compared with the isotype control group, respectively.

As shown in FIG. 9e, tumor-specific CD45+/CD3−/CD49b+NK (NK-cells)-cells of the anti-PD-1 antibody administered group, the 3F12 administered group, the combination of anti-PD-1 antibody and 3F12 administered group was increased by about 1.3 times, 2.1 times, and 3.6 times, as compared with the isotype control group, respectively.

As shown in FIG. 9e, tumor-specific CD45+/CD11b+/Gr1−/F4/80+ macrophage of the anti-PD-1 antibody administered group, the 3F12 administered group, the combination of anti-PD-1 antibody and 3F12 administered group was decreased by about 1.1 times, 1.7 times, and 2.7 times, as compared with the isotype control group, respectively.

As shown in FIG. 9e, tumor-specific CD45+/CD11b+/Gr1+MDSC (myeloid-derived suppressor cells) of the anti-PD-1 antibody administered group, the 3F12 administered group, the combination of anti-PD-1 antibody and 3F12 administered group was decreased by about 1.07 times, 1.15 times, and 1.9 times, as compared with the isotype control group, respectively.

As shown in FIG. 9e, tumor-specific CD45−/CD90.2+ stroma cells of the anti-PD-1 antibody administered group, the 3F12 administered group, the combination of anti-PD-1 antibody and 3F12 administered group was decreased by about −1.06 times, 1.35 times, and 1.86 times, as compared with the isotype control group, respectively.

Treatment with the combination of anti-PD-L1 antibody and 3F12 activated tumor-specific CD3+/CD8+ T-cells and CD45+/CD3−/CD49b+NK (NK-cells)-cells to a greater extent than either agent alone. But, CD45+/CD3−/CD19+ B-cell population was not increased. Treatment with the combination of anti-PD-L1 antibody and 3F12 decreased tumor-specific CD45+/CD11b+/Gr1−/F4/80+ macrophage, CD45+/CD11b+/Gr1+MDSC, and CD45−/CD90.2+ stroma cells to better extent than either agent alone.

The activation may be direct or indirect, i.e., an inhibition of suppressor cells.

Accordingly, 1) anti-BAG2 antibody was found to have significant tumor growth- and metastasis-inhibitory effect, as compared with the isotype control group. 2) The combination of anti-PD-L1 antibody, anti-PD-1 antibody, and anti-CTLA4 antibody as immune checkpoint inhibitors and anti-BAG2 antibodies was found to have significant tumor inhibitory effect, as compared with each of the anti-PD-L1 antibody, anti-PD-1 antibody, anti-CTLA4 antibody, and anti-BAG2 antibody alone in mouse Breast, Lung, Melanoma, Colorectal, and pancreatic cancer Models.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

[Accession Number]

Depositary: Korea Research Institute of Bioscience and Biotechnology
Accession number: KCTC13737BP
Deposit date: Nov. 28, 2018
Depositary: Korea Research Institute of Bioscience and Biotechnology
Accession number: KCTC13738BP
Deposit date: Nov. 28, 2018
Depositary: Korea Research Institute of Bioscience and Biotechnology
Accession number: KCTC13739BP
Deposit date: Nov. 28, 2018
Depositary: Korea Research Institute of Bioscience and Biotechnology
Accession number: KCTC13740BP
Deposit date: Nov. 28, 2018
Depositary: Korea Research Institute of Bioscience and Biotechnology
Accession number: KCTC13741BP
Deposit date: Nov. 28, 2018
Depositary: Korea Research Institute of Bioscience and Biotechnology
Accession number: KCTC13742BP
Deposit date: Nov. 28, 2018
Depositary: Korea Research Institute of Bioscience and Biotechnology
Accession number: KCTC13743BP
Deposit date: Nov. 28, 2018
Depositary: Korea Research Institute of Bioscience and Biotechnology
Accession number: KCTC13744BP
Deposit date: Nov. 28, 2018
Depositary: Korea Research Institute of Bioscience and Biotechnology
Accession number: KCTC13745BP
Deposit date: Nov. 28, 2018
Depositary: Korea Research Institute of Bioscience and Biotechnology
Accession number: KCTC13746BP
Deposit date: Nov. 28, 2018

All of the references cited herein are incorporated by reference in their entirety.

Those skilled in the art will recognize, or be able to ascertain using no more than routine experimentation, many equivalents to the specific embodiments of the invention specifically described herein.

We claim:

1. An antibody or antigen-binding fragment thereof that binds specifically to a BAG2 polypeptide or fragment thereof, wherein the antibody or antigen-binding fragment thereof comprises
a heavy chain variable region comprising a complementarity determining region (VH-CDR)1 consisting of the amino acid sequence of SEQ ID NO: 33, VH-CDR2 consisting of the amino acid sequence of SEQ ID NO: 39, wherein the 6th and 7th Xaa of SEQ ID NO:39 are each Gly, and VH-CDR3 consisting of the amino acid sequence of SEQ ID NO: 45; and a light chain variable region comprising a complementarity determining region (VL-CDR)1 consisting of the amino acid sequence of SEQ ID NO: 51, VL-CDR2 consisting of the amino acid sequence of SEQ ID NO: 57, and VL-CDR3 consisting of the amino acid sequence of SEQ ID NO: 63;
a heavy chain variable region comprising a complementarity determining region (VH-CDR)1 consisting of the amino acid sequence of SEQ ID NO: 33, VH-CDR2 consisting of the amino acid sequence of SEQ ID NO: 39, wherein the 6th and 7th Xaa of SEQ ID NO:39 are Gly and Ala, respectively, and VH-CDR3 consisting of the amino acid sequence of SEQ ID NO: 45; and a light chain variable region comprising a complementarity determining region (VL-CDR)1 consisting of the amino acid sequence of SEQ ID NO: 51, VL-CDR2 consisting of the amino acid sequence of SEQ ID NO: 57, and VL-CDR3 consisting of the amino acid sequence of SEQ ID NO: 63;

a heavy chain variable region comprising a complementarity determining region (VH-CDR)1 consisting of the amino acid sequence of SEQ ID NO: 33, VH-CDR2 consisting of the amino acid sequence of SEQ ID NO: 39, wherein the 6th and 7th Xaa of SEQ ID NO:39 are each Ala and Gly, respectively, and VH-CDR3 consisting of the amino acid sequence of SEQ ID NO: 45; and a light chain variable region comprising a complementarity determining region (VL-CDR)1 consisting of the amino acid sequence of SEQ ID NO: 51, VL-CDR2 consisting of the amino acid sequence of SEQ ID NO: 57, and VL-CDR3 consisting of the amino acid sequence of SEQ ID NO: 63;

a heavy chain variable region comprising a VH-CDR1 consisting of the amino acid sequence of SEQ ID NO: 34, VH-CDR2 consisting of the amino acid sequence of SEQ ID NO: 40, and VH-CDR3 consisting of the amino acid sequence of SEQ ID NO: 46; and a light chain variable region comprising a VL-CDR1 consisting of the amino acid sequence of SEQ ID NO: 52, VL-CDR2 consisting of the amino acid sequence of SEQ ID NO: 58, and VL-CDR3 consisting of the amino acid sequence of SEQ ID NO: 64;

a heavy chain variable region comprising a VH-CDR1 consisting of the amino acid sequence of SEQ ID NO: 35, wherein the second Xaa of SEQ ID NO:35 is Tyr, VH-CDR2 consisting of the amino acid sequence of SEQ ID NO: 41, wherein the eighth Xaa of SEQ ID NO:41 is Ser, and VH-CDR3 consisting of the amino acid sequence of SEQ ID NO: 47 wherein the twelfth Xaa of SEQ ID NO:47 is Tyr; and a light chain variable region comprising a VL-CDR1 consisting of the amino acid sequence of SEQ ID NO: 53, wherein the third Xaa of SEQ ID NO:53 is Ile, VL-CDR2 consisting of the amino acid sequence of SEQ ID NO: 59, wherein the second Xaa of SEQ ID NO:59 is Ala, and VL-CDR3 consisting of the amino acid sequence of SEQ ID NO: 65;

a heavy chain variable region comprising a VH-CDR1 consisting of the amino acid sequence of SEQ ID NO: 35, wherein the second Xaa of SEQ ID NO:35 is Tyr, VH-CDR2 consisting of the amino acid sequence of SEQ ID NO: 41, wherein the eighth Xaa of SEQ ID NO:41 is Ser, and VH-CDR3 consisting of the amino acid sequence of SEQ ID NO: 47 wherein the twelfth Xaa of SEQ ID NO:47 is His; and a light chain variable region comprising a VL-CDR1 consisting of the amino acid sequence of SEQ ID NO: 53, wherein the third Xaa of SEQ ID NO:53 is Met, VL-CDR2 consisting of the amino acid sequence of SEQ ID NO: 59, wherein the second Xaa of SEQ ID NO:59 is Ala, and VL-CDR3 consisting of the amino acid sequence of SEQ ID NO: 65;

a heavy chain variable region comprising a VH-CDR1 consisting of the amino acid sequence of SEQ ID NO: 35, wherein the second Xaa of SEQ ID NO:35 is His, VH-CDR2 consisting of the amino acid sequence of SEQ ID NO: 41, wherein the eighth Xaa of SEQ ID NO:41 is Thr, and VH-CDR3 consisting of the amino acid sequence of SEQ ID NO: 47, wherein the twelfth Xaa of SEQ ID NO: 47 is His; and a light chain variable region comprising a VL-CDR1 consisting of the amino acid sequence of SEQ ID NO: 53, wherein the third Xaa of SEQ ID NO:53 is Met, VL-CDR2 consisting of the amino acid sequence of SEQ ID NO: 59, wherein the second Xaa of SEQ ID NO:59 is Ser, and VL-CDR3 consisting of the amino acid sequence of SEQ ID NO: 65;

a heavy chain variable region comprising a VH-CDR1 consisting of the amino acid sequence of SEQ ID NO: 36, VH-CDR2 consisting of the amino acid sequence of SEQ ID NO: 42, and VH-CDR3 consisting of the amino acid sequence of SEQ ID NO:48; and a light chain variable region comprising a VL-CDR1 consisting of the amino acid sequence of SEQ ID NO: 54, VL-CDR2 consisting of the amino acid sequence of SEQ ID NO: 60, and VL-CDR3 consisting of the amino acid sequence of SEQ ID NO: 66;

a heavy chain variable region comprising a VH-CDR1 consisting of the amino acid sequence of SEQ ID NO: 37, VH-CDR2 consisting of the amino acid sequence of SEQ ID NO: 43, and VH-CDR3 consisting of the amino acid sequence of SEQ ID NO: 49; and a light chain variable region comprising a VL-CDR1 consisting of the amino acid sequence of SEQ ID NO: 55, VL-CDR2 consisting of the amino acid sequence of SEQ ID NO: 61, and VL-CDR3 consisting of the amino acid sequence of SEQ ID NO: 67; or a heavy chain variable region comprising a VH-CDR1 consisting of the amino acid sequence of SEQ ID NO: 38, VH-CDR2 consisting of the amino acid sequence of SEQ ID NO: 44, and VH-CDR3 consisting of the amino acid sequence of SEQ ID NO: 50; and a light chain variable region comprising a VL-CDR1 consisting of the amino acid sequence of SEQ ID NO: 56, VL-CDR2 consisting of the amino acid sequence of SEQ ID NO: 62, and VL-CDR3 consisting of the amino acid sequence of SEQ ID NO: 68.

2. The antibody or antigen-binding fragment thereof of claim 1, being
a heavy chain variable region of SEQ ID NO: 21 and a light chain variable region of SEQ ID NO: 27; a heavy chain variable region of SEQ ID NO: 22 and a light chain variable region of SEQ ID NO: 28; a heavy chain variable region of SEQ ID NO: 23 and a light chain variable region of SEQ ID NO: 29; a heavy chain variable region of SEQ ID NO: 24 and a light chain variable region of SEQ ID NO: 30; a heavy chain variable region of SEQ ID NO: 25 and a light chain variable region of SEQ ID NO: 31; or a heavy chain variable region of SEQ ID NO: 26 and a light chain variable region of SEQ ID NO: 32.

3. The antibody or antigen-binding fragment thereof of claim 1, wherein the antibody or antigen-binding fragment thereof is a monoclonal antibody.

4. The antibody or antigen-binding fragment thereof of claim 1, wherein the antibody or antigen-binding fragment thereof is marked with a detectable label or a label capable of emitting a detectable signal.

5. The antibody or antigen-binding fragment thereof of claim 1, wherein the antibody is humanized.

6. The antibody or antigen-binding fragment thereof of claim 3, wherein the monoclonal antibody is monovalent, an Fab, or a single chain variable fragment antibody (scFv).

7. The antibody or antigen-binding fragment thereof of claim 3, wherein the monoclonal antibody is bi-valent, bi-specific, or tri-specific.

8. The antibody or antigen-binding fragment thereof of claim 3, wherein the monoclonal antibody is fused to a toxin, or a cytokine.

9. The antibody or antigen-binding fragment thereof of claim 8, wherein the monoclonal antibody is fused to a toxin, or a cytokine.

10. The antibody or antigen-binding fragment thereof of claim 1, wherein the antibody or antigen-binding fragment thereof is produced by a hybridoma cell selected from hybridoma cells deposited with accession numbers KCTC 13737BP, KCTC 13738BP, KCTC 13739BP, KCTC 13740BP, KCTC 13741BP, KCTC 13742BP, KCTC 13743BP, KCTC 13744BP, KCTC 13745BP, and KCTC 13746BP.

11. The antibody or antigen-binding fragment thereof of claim 1, wherein the antibody or antigen-binding fragment thereof comprises a plurality of antibodies or antigen-binding fragments thereof.

12. A polynucleotide comprising: a polynucleotide encoding the antibody or antigen-binding fragment of claim 1.

13. The polynucleotide of claim 12, wherein the polynucleotide is a vector.

14. The polynucleotide of claim 13, wherein a detectable label or a label capable of emitting a detectable signal is conjugated with the polynucleotide.

15. A host cell comprising the polynucleotide of claim 12.

16. A method of producing an antibody or an antigen-binding fragment thereof, the method comprising:
    culturing the host cell of claim 15; and
    separating an antibody or antigen-binding fragment thereof from the obtained culture.

17. The method of claim 16, further comprising marking the antibody or antigen-binding fragment thereof.

18. The antibody or antigen-binding fragment of claim 1, which comprises
    a heavy chain variable region comprising a complementarity determining region (VH-CDR)1 consisting of the amino acid sequence of SEQ ID NO: 33, VH-CDR2 consisting of the amino acid sequence of SEQ ID NO: 39, wherein the 6th and 7th Xaa of SEQ ID NO:39 are each Gly, and VH-CDR3 consisting of the amino acid sequence of SEQ ID NO: 45; and a light chain variable region comprising a complementarity determining region (VL-CDR)1 consisting of the amino acid sequence of SEQ ID NO: 51, VL-CDR2 consisting of the amino acid sequence of SEQ ID NO: 57, and VL-CDR3 consisting of the amino acid sequence of SEQ ID NO: 63.

19. The antibody or antigen-binding fragment of claim 1, which comprises
    a heavy chain variable region comprising a complementarity determining region (VH-CDR)1 consisting of the amino acid sequence of SEQ ID NO: 33, VH-CDR2 consisting of the amino acid sequence of SEQ ID NO: 39, wherein the 6th and 7th Xaa of SEQ ID NO:39 are Gly and Ala, respectively, and VH-CDR3 consisting of the amino acid sequence of SEQ ID NO: 45; and a light chain variable region comprising a complementarity determining region (VL-CDR)1 consisting of the amino acid sequence of SEQ ID NO: 51, VL-CDR2 consisting of the amino acid sequence of SEQ ID NO: 57, and VL-CDR3 consisting of the amino acid sequence of SEQ ID NO: 63.

20. The antibody or antigen-binding fragment of claim 1, which comprises
    a heavy chain variable region comprising a complementarity determining region (VH-CDR)1 consisting of the amino acid sequence of SEQ ID NO: 33, VH-CDR2 consisting of the amino acid sequence of SEQ ID NO: 39, wherein the 6th and 7th Xaa of SEQ ID NO:39 are each Ala and Gly, respectively, and VH-CDR3 consisting of the amino acid sequence of SEQ ID NO: 45; and a light chain variable region comprising a complementarity determining region (VL-CDR)1 consisting of the amino acid sequence of SEQ ID NO: 51, VL-CDR2 consisting of the amino acid sequence of SEQ ID NO: 57, and VL-CDR3 consisting of the amino acid sequence of SEQ ID NO: 63.

21. The antibody or antigen-binding fragment of claim 1, which comprises
    a heavy chain variable region comprising a VH-CDR1 consisting of the amino acid sequence of SEQ ID NO: 34, VH-CDR2 consisting of the amino acid sequence of SEQ ID NO: 40, and VH-CDR3 consisting of the amino acid sequence of SEQ ID NO: 46; and a light chain variable region comprising a VL-CDR1 consisting of the amino acid sequence of SEQ ID NO: 52, VL-CDR2 consisting of the amino acid sequence of SEQ ID NO: 58, and VL-CDR3 consisting of the amino acid sequence of SEQ ID NO: 64.

22. The antibody or antigen-binding fragment of claim 1, which comprises
    a heavy chain variable region comprising a VH-CDR1 consisting of the amino acid sequence of SEQ ID NO: 35, wherein the second Xaa of SEQ ID NO:35 is Tyr, VH-CDR2 consisting of the amino acid sequence of SEQ ID NO: 41, wherein the eighth Xaa of SEQ ID NO:41 is Ser, and VH-CDR3 consisting of the amino acid sequence of SEQ ID NO: 47 wherein the twelfth Xaa of SEQ ID NO:47 is Tyr; and a light chain variable region comprising a VL-CDR1 consisting of the amino acid sequence of SEQ ID NO: 53, wherein the third Xaa of SEQ ID NO:53 is Ile, VL-CDR2 consisting of the amino acid sequence of SEQ ID NO: 59, wherein the second Xaa of SEQ ID NO:59 is Ala, and VL-CDR3 consisting of the amino acid sequence of SEQ ID NO: 65.

23. The antibody or antigen-binding fragment of claim 1, which comprises
    a heavy chain variable region comprising a VH-CDR1 consisting of the amino acid sequence of SEQ ID NO: 35, wherein the second Xaa of SEQ ID NO:35 is Tyr, VH-CDR2 consisting of the amino acid sequence of SEQ ID NO: 41, wherein the eighth Xaa of SEQ ID NO:41 is Ser, and VH-CDR3 consisting of the amino acid sequence of SEQ ID NO: 47 wherein the twelfth Xaa of SEQ ID NO:47 is His; and a light chain variable region comprising a VL-CDR1 consisting of the amino acid sequence of SEQ ID NO: 53, wherein the third Xaa of SEQ ID NO:53 is Met, VL-CDR2 consisting of the amino acid sequence of SEQ ID NO: 59, wherein the second Xaa of SEQ ID NO:59 is Ala, and VL-CDR3 consisting of the amino acid sequence of SEQ ID NO: 65.

24. The antibody or antigen-binding fragment of claim 1, which comprises
    a heavy chain variable region comprising a VH-CDR1 consisting of the amino acid sequence of SEQ ID NO: 35, wherein the second Xaa of SEQ ID NO:35 is His, VH-CDR2 consisting of the amino acid sequence of SEQ ID NO: 41, wherein the eighth Xaa of SEQ ID NO:41 is Thr, and VH-CDR3 consisting of the amino acid sequence of SEQ ID NO: 47, wherein the twelfth Xaa of SEQ ID NO:47 is His; and a light chain variable region comprising a VL-CDR1 consisting of the amino acid sequence of SEQ ID NO: 53, wherein the third Xaa of SEQ ID NO:53 is Met, VL-CDR2 consisting of the amino acid sequence of SEQ ID NO: 59, wherein the second Xaa of SEQ ID NO:59 is Ser, and VL-CDR3 consisting of the amino acid sequence of SEQ ID NO: 65.

25. The antibody or antigen-binding fragment of claim 1, which comprises
a heavy chain variable region comprising a VH-CDR1 consisting of the amino acid sequence of SEQ ID NO: 36, VH-CDR2 consisting of the amino acid sequence of SEQ ID NO: 42, and VH-CDR3 consisting of the amino acid sequence of SEQ ID NO:48; and a light chain variable region comprising a VL-CDR1 consisting of the amino acid sequence of SEQ ID NO: 54, VL-CDR2 consisting of the amino acid sequence of SEQ ID NO: 60, and VL-CDR3 consisting of the amino acid sequence of SEQ ID NO: 66.

26. The antibody or antigen-binding fragment of claim 1, which comprises
a heavy chain variable region comprising a VH-CDR1 consisting of the amino acid sequence of SEQ ID NO: 37, VH-CDR2 consisting of the amino acid sequence of SEQ ID NO: 43, and VH-CDR3 consisting of the amino acid sequence of SEQ ID NO: 49; and a light chain variable region comprising a VL-CDR1 consisting of the amino acid sequence of SEQ ID NO: 55, VL-CDR2 consisting of the amino acid sequence of SEQ ID NO: 61, and VL-CDR3 consisting of the amino acid sequence of SEQ ID NO: 67.

27. The antibody or antigen-binding fragment of claim 1, which comprises
a heavy chain variable region comprising a VH-CDR1 consisting of the amino acid sequence of SEQ ID NO: 38, VH-CDR2 consisting of the amino acid sequence of SEQ ID NO: 44, and VH-CDR3 consisting of the amino acid sequence of SEQ ID NO: 50; and a light chain variable region comprising a VL-CDR1 consisting of the amino acid sequence of SEQ ID NO: 56, VL-CDR2 consisting of the amino acid sequence of SEQ ID NO: 62, and VL-CDR3 consisting of the amino acid sequence of SEQ ID NO: 68.

* * * * *

SEQUENCE LISTING

<160> NUMBER OF SEQ ID NOS: 86

<210> SEQ ID NO 1

```
<211> LENGTH: 369
<212> TYPE: DNA
<213> ORGANISM: Artificial Sequence
<220> FEATURE:
<223> OTHER INFORMATION: 2A11-VH

<400> SEQUENCE: 1
caggtccaac tgcagcagcc tggggctgag ctggtgaggc ctggggcttc agtgacgctg      60
tcctgcaagg cttcgggcta cacatttact gactatgaaa tgcactgggt gaagcagact     120
cctgtgcatg gcctggaatg gattggagtt attgatcctg aaactggtgc tactgcctac     180
aatcagaagt tcaagggcaa ggccacactg actgcagaca atcctccag tacagcctac      240 atggagctcc gcagcctgac atctgaggac tctgccgtct attactgtac aagagggaaa     300
ttttattact ccggtcggga ctatgctatg gactactggg gtcaaggaac ctcagtcacc     360
gtctcctca                                                             369

<210> SEQ ID NO 2
<211> LENGTH: 369
<212> TYPE: DNA
<213> ORGANISM: Artificial Sequence
<220> FEATURE:
<223> OTHER INFORMATION: 4C2-VH

<400> SEQUENCE: 2
caggtccaac tgcagcagcc tggggctgag ctggtgaggc ctggggcttc agtgacgctg      60
tcctgcaagg cttcgggcta cacatttact gactatgaaa tgcactgggt gaagcagact     120
cctgtgcatg gcctggaatg gattggagtt attgatcctg aaactggtgc tactgcctac     180
aatcagaagt tcaagggcaa ggccacactg actgcagaca atcctccag tacagcctac      240 atggagctcc gcagcctgac atctgaggac tctgccgtct attactgtac aagagggaaa     300
ttttattact ccggtcggga ctatgctatg gactactggg gtcaaggaac ctcagtcacc     360
gtctcctca                                                             369

<210> SEQ ID NO 3
<211> LENGTH: 369
<212> TYPE: DNA
<213> ORGANISM: Artificial Sequence
<220> FEATURE:
<223> OTHER INFORMATION: 8C4-VH

<400> SEQUENCE: 3
caggtccaac tgcagcagcc tggggctgag ctggtgaggc ctggggcttc agtgacgctg      60
tcctgcaagg cttcgggcta cacatttact gactatgaaa tgcactgggt gaagcagact     120
cctgtgcatg gcctggaatg gattggagtt attgatcctg aaactgctgg tactgcctac     180
aatcagaagt tcaagggcaa ggccacactg actgcagaca atcctccag tacagcctac      240 atggagctcc gcagcctgac atctgaggac tctgccgtct attactgtac aagagggaaa     300
ttttattact ccggtcggga ctatgctatg gactactggg gtcaaggaac ctcagtcacc     360
gtctcctca                                                             369

<210> SEQ ID NO 4
<211> LENGTH: 366
<212> TYPE: DNA
<213> ORGANISM: Artificial Sequence
<220> FEATURE:
<223> OTHER INFORMATION: 3B5-VH

<400> SEQUENCE: 4
```

```
gaggtccagc tgcaacagtc tggacctgag ctggtgaagc ctggggcttc agtgaagtta      60
tcctgcaagg cttctggtta ctcattcact gactacacct tttactgggt gaggcagagc     120
catggagaga gccttgagtg gattggatat attgatcctt acaatggtgg taatacttat     180
aaccggaagt tcaagggcaa ggccacattg actgttgaca gtcctccag  cacagccttc     240 atgcatctca acagcctgac atctgaagac tctgcagtct attactgtgc gagagggtac     300
tataggtacg gggggggggg ggactttgac tactggggcc aaggcaccac tctcacagtc     360
tcctca                                                                  366
```

```
<210> SEQ ID NO 5
<211> LENGTH: 357
<212> TYPE: DNA
<213> ORGANISM: Artificial Sequence
<220> FEATURE:
<223> OTHER INFORMATION: 9B3-VH

<400> SEQUENCE: 5
gaggtccagc tgcaacaatc tggagctgag ctggtaaggc ctgggacttc agtgaaggtg      60
tcctgcaagg cttctggata cgccttcact aattacatga tagagtggat aaaacagagg     120
cctggacagg gccttgagtg gattggagtg attaatcctg aagtggtgg  tagttattac     180 aatgagaagg tcaagggcaa ggcaacactg accgcagaca atcctccag  cactgcctac     240 atgcagttca gcagcctgac agctgatgac tctgcggtct atttctgtcg gatctatggt     300
aactacaagg ggtactttga ctattggggc caaggcacca ctctcacagt ctcctca       357
```

```
<210> SEQ ID NO 6
<211> LENGTH: 357
<212> TYPE: DNA
<213> ORGANISM: Artificial Sequence
<220> FEATURE:
<223> OTHER INFORMATION: 9B12-VH

<400> SEQUENCE: 6
caggtccaac tgcagcagtc tggagctgag ctggtaaggc ctgggacttc agtgaaggtg      60
tcctgcaagg cttctggata cgccttcact aattacatga tagagtggat aaaacagagg     120
cctggacagg gccttgagtg gattggagtg attaatcctg aagtggtgg  tagttataac     180 aatgagaagg tcaagggcaa ggcaacactg accgcagaca gatcctccag cactgcctac     240
atgcagttca gcagcctgac agctgatgac tctggggtct atttctgtcg gatctatggt     300
aactacaagg ggtactttga ccattggggc caaggcacca ctctcacagt ctcctca       357
```

```
<210> SEQ ID NO 7
<211> LENGTH: 357
<212> TYPE: DNA
<213> ORGANISM: Artificial Sequence
<220> FEATURE:
<223> OTHER INFORMATION: 3B10-VH

<400> SEQUENCE: 7
caggtccaac tgcagcagcc tggagctgag ctggcaaggc ctgggacttc agtgaaggtg      60
tcctgcaagg cttctggcca cgccttcact aattacatga tagagtggat aaaacagagg     120
cctggacagg gccttgagtg gattggagtg attaatcctg aagtggtgg  tacttataac     180 agtgagaagg tcaagggcaa ggcaacactg accgcagaca gatcctccag cactgcctac     240
atgcagctca gcagcctgac agctgatgac tctggggtct atttctgtcg gatctatggt     300
```
aactacaagg ggtactttga ccattggggc caaggcacca ctctcacagt ctcctca      357

<210> SEQ ID NO 8
<211> LENGTH: 363
<212> TYPE: DNA
<213> ORGANISM: Artificial Sequence
<220> FEATURE:
<223> OTHER INFORMATION: 10H7-VH

<400> SEQUENCE: 8
cagatccagt tggtgcagtc tggacctgag ctgaagaagc ctggagagac agtcaagatc      60
tcctgcaagg cttctggtta taccttcaca gactattcaa ttcactgggt gaggcaggct     120
ccaggaaagg gttttaagtg gatgggctgg ataaacactg agactggtga gccaacatat     180
gcagatgact tcaagggacg gtttgccctc tctttggaaa cctctgccag cactgcctac     240
ttgcagatca acaacctcaa aaatgaggac acggctacat atttctgtgc tagatttgac     300
tacggtacta gttactggta cttcgatgtc tggggcgcag ggaccacggt caccgtctcc     360
tca                                                                   363

<210> SEQ ID NO 9
<211> LENGTH: 351
<212> TYPE: DNA
<213> ORGANISM: Artificial Sequence
<220> FEATURE:
<223> OTHER INFORMATION: 3G8-VH

<400> SEQUENCE: 9
cagatccagt tggtgcagtc tggacctgag ctgaagaagc ctggagagac agtcaagatc      60
tcctgcaagg cttctgggta tagcttcaca agtatggaa tgaactgggt gaagcaggct     120
ccaggaaagg atatcaagtg gatggggtgg ataaacacca acactggaga ggcaacatat     180
ggtgaagagg tcaagggacg gtttgccttc tctttggaaa cctctgccag cactgcctat     240
ttgcagatca acaacctcaa aaatgaggac acggctacat atttctgtgc aagattggga     300
ttgaggtacc ttgactactg gggccaaggc accactctca cagtctcctc a             351

<210> SEQ ID NO 10
<211> LENGTH: 336
<212> TYPE: DNA
<213> ORGANISM: Artificial Sequence
<220> FEATURE:
<223> OTHER INFORMATION: 3F12-VH

<400> SEQUENCE: 10
caggtgcaac tgcaggagtc aggacctgac ctggtgaaac cttctcagtc actttcactc      60
acctgcactg tcactgggta ctccatcacc agtggttata ctggcactg gatccggcag     120
tttccaggaa acaaattgga atggatgggc tacatatatt atagaggtag cactaactac     180
aacccatctc tcaaaagtcg aatctctatc actcgagaca catccaagaa ccagttcttc     240
ctgctgttga atctgtgac tactgaggac acagccacat attactgtgc aagagaggct     300
tactggggcc aagggactct ggtcactgtc tcagca                               336

<210> SEQ ID NO 11
<211> LENGTH: 336
<212> TYPE: DNA
<213> ORGANISM: Artificial Sequence
<220> FEATURE:
<223> OTHER INFORMATION: 2A11-VL

<400> SEQUENCE: 11

```
gatgttttga tgacccaaac tccactctcc ctgcctgtca gtcttggaga tcaagcctcc    60
atctcttgca gatctagtca gagtattgta catagtaatg gaaacaccta tttagaatgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ttcaaggttc acaggttcct   300
ccgacgttcg gtggaggcac caagctggaa atcaaa                             336
```

<210> SEQ ID NO 12
<211> LENGTH: 336
<212> TYPE: DNA
<213> ORGANISM: Artificial Sequence
<220> FEATURE:
<223> OTHER INFORMATION: 4C2-VL

<400> SEQUENCE: 12

```
gatgttttga tgacccaaac tccactctcc ctgcctgtca gtcttggaga tcaagcctcc    60
atctcttgca gatctagtca gagtattgta catagtaatg gaaacaccta tttagaatgg   120
tacctgcaga agccaggcca gtctccaaag ctcctgttct acaaagtttc caaccgattt   180
tctggggtcc cagacaggtt cagtggcagt ggatcaggga cagatttcac actcaagatc   240
agcagagtgg aggctgagga tctgggagtt tatttctgct ttcaaggttc acaggttcct   300
ccgacgttcg gtggaggcac caagctggaa atcaaa                             336
```

<210> SEQ ID NO 13
<211> LENGTH: 336
<212> TYPE: DNA
<213> ORGANISM: Artificial Sequence
<220> FEATURE:
<223> OTHER INFORMATION: 8C4-VL

<400> SEQUENCE: 13

```
gatgttttga tgacccaaac tccactctcc ctgcctgtca gtcttggaga tcaagcctcc    60
atctcttgca gatctagtca gagtattgta catagtaatg gaaacaccta tttagaatgg   120
tacctgcaga agccaggcca gtctccaaag ctcctgttct acaaagtttc caaccgattt   180
tctggggtcc cagacaggtt cagtggcagt ggatcaggga cagatttcac actcaagatc   240
agcagagtgg aggctgagga tctgggagtt tatttctgct ttcaaggttc acaggttcct   300
ccgacgttcg gtggaggcac caagctggaa atcaaa                             336
```

<210> SEQ ID NO 14
<211> LENGTH: 336
<212> TYPE: DNA
<213> ORGANISM: Artificial Sequence
<220> FEATURE:
<223> OTHER INFORMATION: 3B5-VL

<400> SEQUENCE: 14

```
gatgttttga tgacccaaac tccactctcc ctgcctgtca gtcttggaga tcaagcctcc    60
atctcttgca gatccagtca gagccttgta cacagtaatg gaaacaccta tttacattgg   120
tacctgcaga agccaggcca gtctccaaag ctcctgatcc acaaagtttc caaccgattt   180
tctggggtcc cagacaggtt cagtggcagt ggatcaggga cagatttcac actcaagatc   240
agcagagtgg aggctgagga tctgggaatt tatttctgct ctcaaaatac acatattcct   300
ccgacgttcg ctggaggcac caagctggaa atcaaa                             336
```

<210> SEQ ID NO 15
<211> LENGTH: 357
<212> TYPE: DNA
<213> ORGANISM: Artificial Sequence
<220> FEATURE:
<223> OTHER INFORMATION: 9B3-VL

<400> SEQUENCE: 15

```
gaggtccagc tgcaacaatc tggagctgag ctggtaaggc ctgggacttc agtgaaggtg        60
tcctgcaagg cttctggata cgccttcact aattacatga tagagtggat aaaacagagg       120
cctggacagg gccttgagtg gattggagtg attaatcctg aagtggtgg tagttattac        180 aatgagaagg tcaagggcaa ggcaacactg accgcagaca atcctccag cactgcctac        240 atgcagttca gcagcctgac agctgatgac tctgcggtct atttctgtcg gatctatggt       300
aactacaagg ggtactttga ctattgggc caaggcacca ctctcacagt ctcctca          357
```

<210> SEQ ID NO 16
<211> LENGTH: 321
<212> TYPE: DNA
<213> ORGANISM: Artificial Sequence
<220> FEATURE:
<223> OTHER INFORMATION: 9B12-VL

<400> SEQUENCE: 16

```
gacattgtga tgacccagtc tccatcttcc atgtatgcat ctctaggaga gagagtcact        60
atcacttgca aggcgagtca ggacatgaat agctatttaa gctggttcca gcagaaacca       120
gggaaatctc ctaagaccct gatctatcgt gcaaacagat ggtagatgg ggtcccatca        180 aggttcagtg gcagtggatc tgggcaagat tattctctca ccatcagcag cctggagtat       240
gaagatatgg gaatttatta ttgtctacag aatgatgagt ttccattcac gttcggctcg       300
gggacaaagc tggaaatgaa g                                                  321
```

<210> SEQ ID NO 17
<211> LENGTH: 321
<212> TYPE: DNA
<213> ORGANISM: Artificial Sequence
<220> FEATURE:
<223> OTHER INFORMATION: 3B10-VL

<400> SEQUENCE: 17

```
gacattgtga tgacccagtc tccatcttcc atgtatgcat ctctaggaga gagagtcact        60
atcacttgca aggcgagtca ggacatgaat agctatttaa gctggttcca gcagaaacca       120
gggaaatctc ctaagaccct gatctatcgt tcaaacagat ggtagatgg ggtcccatca        180 aggttcagtg gcagtggatc tgggcaagat tattctctca ccatcagcag cctggactat       240
gaagatatgg gaatttatta ttgtctacag aatgatgagt ttccattcac gttcggctcg       300
gggacaaagc tggaaataaa a                                                  321
```

<210> SEQ ID NO 18
<211> LENGTH: 351
<212> TYPE: DNA
<213> ORGANISM: Artificial Sequence
<220> FEATURE:
<223> OTHER INFORMATION: 10H7-VL

<400> SEQUENCE: 18

```
gatgtccaga tgacccagtc tccatcctcc ctgtctgcat ctgtgggaga cagagccacc        60
atcacttgcc gggcaagtca gagcattagc agctatttaa attggtatca gcagaaaccc       120
```

| | |
|---|---|
| gggaaagccc ctaagctcct gatctatgct gcatccagtt tgcaaagtgg ggtcccatca | 180 |
| aggttcagtg gcagtggatc tgggacagat ttcactctca ccatcagcag tctgcaacct | 240 |
| gaagattttg caacttacta ctgtcaacag agttacacta ccccgctcac tttcggtgga | 300 |
| ggcaccaagc tggaaatcaa acgtggagga gccagcctcg tggaattcaa g | 351 |

<210> SEQ ID NO 19
<211> LENGTH: 333
<212> TYPE: DNA
<213> ORGANISM: Artificial Sequence
<220> FEATURE:
<223> OTHER INFORMATION: 3G8-VL

<400> SEQUENCE: 19

| | |
|---|---|
| gacattgtga tgacccagtc tcctgcttcc ttagttgtat ctctggggca gagggccacc | 60 |
| atctcatgca gggccagcaa aagtgtcagt acatctgact atagttatat gcactggtac | 120 |
| caacagaaac caggacagcc acccaaagtc ctcatctatc ttgcatccaa cctagaatct | 180 |
| ggggtccctg ccaggttcag tggcagtggg tctgggacag acttcaccct caacatccat | 240 |
| cctgtggagg aggaggatgc tgcaacctat tactgtcagc acaataggga gcttcctccc | 300 |
| acgttcggtg ctgggaccaa gctggagctg aaa | 333 |

<210> SEQ ID NO 20
<211> LENGTH: 336
<212> TYPE: DNA
<213> ORGANISM: Artificial Sequence
<220> FEATURE:
<223> OTHER INFORMATION: 3F12-VL

<400> SEQUENCE: 20

| | |
|---|---|
| gatgttttga tgacccaaac tccactcact ttgtcggtta cctttgggca gccagcctcc | 60 |
| atctcttgca ggtcaagtca gagcctctta gatagtgatg agagacata tttgaattgg | 120 |
| ttgttacaga ggccaggcca gtctccaaag cgcctaatct atctggtgtc taaactggac | 180 |
| tctggagtcc ctgacaggtt cactggcagt ggatcaggga cagatttcac actgaaaatc | 240 |
| agcagagtgg aggctgagga tttgggagtt tattattgct ggcaaggtac acattttccg | 300 |
| tacacgttcg gaggggggac caagctggaa ataaaa | 336 |

<210> SEQ ID NO 21
<211> LENGTH: 123
<212> TYPE: PRT
<213> ORGANISM: Artificial Sequence
<220> FEATURE:
<223> OTHER INFORMATION: 2A11,4C2,8C4-VH
<220> FEATURE:
<221> NAME/KEY: VARIANT
<222> LOCATION: (56)..(57)
<223> OTHER INFORMATION: Xaa is Gly or Ala

<400> SEQUENCE: 21

Gln Val Gln Leu Gln Gln Pro Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ile Ile Asp Pro Glu Thr Xaa Xaa Thr Ala Tyr Asn Gln Lys Phe
    50                  55                  60

```
Lys Gly Lys Ala Thr Leu Thr Ala Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Gly Lys Phe Tyr Tyr Ser Gly Arg Asp Tyr Ala Met Asp Tyr
            100                 105                 110

Trp Gly Gln Gly Thr Ser Val Thr Val Ser Ser
        115                 120
```

<210> SEQ ID NO 22
<211> LENGTH: 122
<212> TYPE: PRT
<213> ORGANISM: Artificial Sequence
<220> FEATURE:
<223> OTHER INFORMATION: 3B5-VH

<400> SEQUENCE: 22

```
Glu Val Gln Leu Gln Gln Ser Gly Pro Glu Leu Val Lys Pro Gly Ala
 1               5                  10                  15

Ser Val Lys Leu Ser Cys Lys Ala Ser Gly Tyr Ser Phe Thr Asp Tyr
                 20                  25                  30

Thr Phe Tyr Trp Val Arg Gln Ser His Gly Glu Ser Leu Glu Trp Ile
            35                  40                  45

Gly Tyr Ile Asp Pro Tyr Asn Gly Gly Asn Thr Tyr Asn Arg Lys Phe
 50                  55                  60

Lys Gly Lys Ala Thr Leu Thr Val Asp Lys Ser Ser Ser Thr Ala Phe
 65                  70                  75                  80

Met His Leu Asn Ser Leu Thr Ser Glu Asp Ser Ala Val Tyr Tyr Cys
                 85                  90                  95

Ala Arg Gly Tyr Tyr Arg Tyr Gly Gly Gly Asp Phe Asp Tyr Trp
            100                 105                 110

Gly Gln Gly Thr Thr Leu Thr Val Ser Ser
        115                 120
```

<210> SEQ ID NO 23
<211> LENGTH: 119
<212> TYPE: PRT
<213> ORGANISM: Artificial Sequence
<220> FEATURE:
<223> OTHER INFORMATION: 9B3,9B12,3B10-VH
<220> FEATURE:
<221> NAME/KEY: VARIANT
<222> LOCATION: (1)..(1)
<223> OTHER INFORMATION: Xaa is Glu or Gln
<220> FEATURE:
<221> NAME/KEY: VARIANT
<222> LOCATION: (7)..(7)
<223> OTHER INFORMATION: Xaa is Ser or Pro
<220> FEATURE:
<221> NAME/KEY: VARIANT
<222> LOCATION: (12)..(12)
<223> OTHER INFORMATION: Xaa is Val or Ala
<220> FEATURE:
<221> NAME/KEY: VARIANT
<222> LOCATION: (27)..(27)
<223> OTHER INFORMATION: Xaa is Tyr or His
<220> FEATURE:
<221> NAME/KEY: VARIANT
<222> LOCATION: (58)..(58)
<223> OTHER INFORMATION: Xaa is Ser or Thr
<220> FEATURE:
<221> NAME/KEY: VARIANT
<222> LOCATION: (61)..(61)
<223> OTHER INFORMATION: Xaa is Asn or Ser
<220> FEATURE:
<221> NAME/KEY: VARIANT

```
<222> LOCATION: (74)..(74)
<223> OTHER INFORMATION: Xaa is Arg or Lys
<220> FEATURE:
<221> NAME/KEY: VARIANT
<222> LOCATION: (83)..(83)
<223> OTHER INFORMATION: Xaa is Phe or Leu
<220> FEATURE:
<221> NAME/KEY: VARIANT
<222> LOCATION: (92)..(92)
<223> OTHER INFORMATION: Xaa is Gly or Ala
<220> FEATURE:
<221> NAME/KEY: VARIANT
<222> LOCATION: (108)..(108)
<223> OTHER INFORMATION: Xaa is His or Tyr

<400> SEQUENCE: 23

Xaa Val Gln Leu Gln Gln Xaa Gly Ala Glu Leu Xaa Arg Pro Gly Thr
1               5                   10                  15

Ser Val Lys Val Ser Cys Lys Ala Ser Gly Xaa Ala Phe Thr Asn Tyr
                20                  25                  30

Met Ile Glu Trp Ile Lys Gln Arg Pro Gly Gln Gly Leu Glu Trp Ile
            35                  40                  45

Gly Val Ile Asn Pro Gly Ser Gly Xaa Tyr Tyr Xaa Glu Lys Val
    50                  55                  60

Lys Gly Lys Ala Thr Leu Thr Ala Asp Xaa Ser Ser Thr Ala Tyr
65                  70                  75                  80

Met Gln Xaa Ser Ser Leu Thr Ala Asp Asp Ser Xaa Val Tyr Phe Cys
            85                  90                  95

Arg Ile Tyr Gly Asn Tyr Lys Gly Tyr Phe Asp Xaa Trp Gly Gln Gly
                100                 105                 110

Thr Thr Leu Thr Val Ser Ser
            115

<210> SEQ ID NO 24
<211> LENGTH: 121
<212> TYPE: PRT
<213> ORGANISM: Artificial Sequence
<220> FEATURE:
<223> OTHER INFORMATION: 10H7-VH

<400> SEQUENCE: 24

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Ile His Trp Val Arg Gln Ala Pro Gly Lys Gly Phe Lys Trp Met
            35                  40                  45

Gly Trp Ile Asn Thr Glu Thr Gly Glu Pro Thr Tyr Ala Asp Asp Phe
    50                  55                  60

Lys Gly Arg Phe Ala Leu Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
            85                  90                  95

Ala Arg Phe Asp Tyr Gly Thr Ser Tyr Trp Tyr Phe Asp Val Trp Gly
                100                 105                 110

Ala Gly Thr Thr Val Thr Val Ser Ser
            115                 120

<210> SEQ ID NO 25
<211> LENGTH: 117
<212> TYPE: PRT
```

```
<213> ORGANISM: Artificial Sequence
<220> FEATURE:
<223> OTHER INFORMATION: 3G8-VH

<400> SEQUENCE: 25

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Lys Tyr
            20                  25                  30

Gly Met Asn Trp Val Lys Gln Ala Pro Gly Lys Asp Ile Lys Trp Met
        35                  40                  45

Gly Trp Ile Asn Thr Asn Thr Gly Glu Ala Thr Tyr Gly Glu Glu Val
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Leu Arg Tyr Leu Asp Tyr Trp Gly Gln Gly Thr Thr
            100                 105                 110

Leu Thr Val Ser Ser
        115

<210> SEQ ID NO 26
<211> LENGTH: 112
<212> TYPE: PRT
<213> ORGANISM: Artificial Sequence
<220> FEATURE:
<223> OTHER INFORMATION: 3F12-VH

<400> SEQUENCE: 26

Gln Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile Tyr Tyr Arg Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Leu Leu Lys Ser Val Thr Thr Glu Asp Thr Ala Thr Tyr Tyr Cys
                85                  90                  95

Ala Arg Glu Ala Tyr Trp Gly Gln Gly Thr Leu Val Thr Val Ser Ala
            100                 105                 110

<210> SEQ ID NO 27
<211> LENGTH: 112
<212> TYPE: PRT
<213> ORGANISM: Artificial Sequence
<220> FEATURE:
<223> OTHER INFORMATION: 2A11,4C2,8C4-VL
<220> FEATURE:
<221> NAME/KEY: VARIANT
<222> LOCATION: (53)..(53)
<223> OTHER INFORMATION: Xaa is Ile or Phe

<400> SEQUENCE: 27

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
```

```
                    20                  25                  30

Asn Gly Asn Thr Tyr Leu Glu Trp Tyr Leu Gln Lys Pro Gly Gln Ser
                35                  40                  45

Pro Lys Leu Leu Xaa Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Phe Gln Gly
                 85                  90                  95

Ser Gln Val Pro Pro Thr Phe Gly Gly Gly Thr Lys Leu Glu Ile Lys
            100                 105                 110

<210> SEQ ID NO 28
<211> LENGTH: 112
<212> TYPE: PRT
<213> ORGANISM: Artificial Sequence
<220> FEATURE:
<223> OTHER INFORMATION: 3B5-VL

<400> SEQUENCE: 28

Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Leu Gln Lys Pro Gly Gln Ser
                35                  40                  45

Pro Lys Leu Leu Ile His Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Ile Tyr Phe Cys Ser Gln Asn
                 85                  90                  95

Thr His Ile Pro Pro Thr Phe Ala Gly Gly Thr Lys Leu Glu Ile Lys
            100                 105                 110

<210> SEQ ID NO 29
<211> LENGTH: 107
<212> TYPE: PRT
<213> ORGANISM: Artificial Sequence
<220> FEATURE:
<223> OTHER INFORMATION: 9B3,9B12,3B10-VL
<220> FEATURE:
<221> NAME/KEY: VARIANT
<222> LOCATION: (29)..(29)
<223> OTHER INFORMATION: Xaa is Met or Ile
<220> FEATURE:
<221> NAME/KEY: VARIANT
<222> LOCATION: (51)..(51)
<223> OTHER INFORMATION: Xaa is Ala or Ser
<220> FEATURE:
<221> NAME/KEY: VARIANT
<222> LOCATION: (79)..(79)
<223> OTHER INFORMATION: Xaa is Glu or Asp
<220> FEATURE:
<221> NAME/KEY: VARIANT
<222> LOCATION: (106)..(106)
<223> OTHER INFORMATION: Xaa is Met or Ile

<400> SEQUENCE: 29

Asp Ile Val Met Thr Gln Ser Pro Ser Ser Met Tyr Ala Ser Leu Gly
  1               5                  10                  15

Glu Arg Val Thr Ile Thr Cys Lys Ala Ser Gln Asp Xaa Asn Ser Tyr
                 20                  25                  30
```

```
Leu Ser Trp Phe Gln Gln Lys Pro Gly Lys Ser Pro Lys Thr Leu Ile
        35                  40                  45

Tyr Arg Xaa Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Xaa Tyr
65                  70                  75                  80

Glu Asp Met Gly Ile Tyr Tyr Cys Leu Gln Asn Asp Glu Phe Pro Phe
                85                  90                  95

Thr Phe Gly Ser Gly Thr Lys Leu Glu Xaa Lys
                100                 105

<210> SEQ ID NO 30
<211> LENGTH: 107
<212> TYPE: PRT
<213> ORGANISM: Artificial Sequence
<220> FEATURE:
<223> OTHER INFORMATION: 10H7-VL

<400> SEQUENCE: 30

Asp Val Gln Met Thr Gln Ser Pro Ser Ser Leu Ser Ala Ser Val Gly
1               5                   10                  15

Asp Arg Ala Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Leu
                85                  90                  95

Thr Phe Gly Gly Gly Thr Lys Leu Glu Ile Lys
                100                 105

<210> SEQ ID NO 31
<211> LENGTH: 111
<212> TYPE: PRT
<213> ORGANISM: Artificial Sequence
<220> FEATURE:
<223> OTHER INFORMATION: 3G8-VL

<400> SEQUENCE: 31

Asp Ile Val Met Thr Gln Ser Pro Ala Ser Leu Val Val Ser Leu Gly
1               5                   10                  15

Gln Arg Ala Thr Ile Ser Cys Arg Ala Ser Lys Ser Val Ser Thr Ser
            20                  25                  30

Asp Tyr Ser Tyr Met His Trp Tyr Gln Gln Lys Pro Gly Gln Pro Pro
        35                  40                  45

Lys Val Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Asn Arg
                85                  90                  95

Glu Leu Pro Pro Thr Phe Gly Ala Gly Thr Lys Leu Glu Leu Lys
                100                 105                 110
```

```
<210> SEQ ID NO 32
<211> LENGTH: 112
<212> TYPE: PRT
<213> ORGANISM: Artificial Sequence
<220> FEATURE:
<223> OTHER INFORMATION: 3F12-VL

<400> SEQUENCE: 32

Asp Val Leu Met Thr Gln Thr Pro Leu Thr Leu Ser Val Thr Phe Gly
1               5                   10                  15

Gln Pro Ala Ser Ile Ser Cys Arg Ser Ser Gln Ser Leu Leu Asp Ser
            20                  25                  30

Asp Gly Glu Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

<210> SEQ ID NO 33
<211> LENGTH: 8
<212> TYPE: PRT
<213> ORGANISM: Artificial Sequence
<220> FEATURE:
<223> OTHER INFORMATION: 2A11,4C2,8C4-VHCDR1

<400> SEQUENCE: 33

Gly Tyr Thr Phe Thr Asp Tyr Glu
1               5

<210> SEQ ID NO 34
<211> LENGTH: 8
<212> TYPE: PRT
<213> ORGANISM: Artificial Sequence
<220> FEATURE:
<223> OTHER INFORMATION: 3B5-VHCDR1

<400> SEQUENCE: 34

Gly Tyr Ser Phe Thr Asp Tyr Thr
1               5

<210> SEQ ID NO 35
<211> LENGTH: 8
<212> TYPE: PRT
<213> ORGANISM: Artificial Sequence
<220> FEATURE:
<223> OTHER INFORMATION: 9B3,9B12,3B10-VHCDR1
<220> FEATURE:
<221> NAME/KEY: VARIANT
<222> LOCATION: (2)..(2)
<223> OTHER INFORMATION: Xaa is Tyr or His

<400> SEQUENCE: 35

Gly Xaa Ala Phe Thr Asn Tyr Met
1               5

<210> SEQ ID NO 36
<211> LENGTH: 8
<212> TYPE: PRT
<213> ORGANISM: Artificial Sequence
<220> FEATURE:
```

```
<223> OTHER INFORMATION: 10H7-VHCDR1

<400> SEQUENCE: 36

Gly Tyr Thr Phe Thr Asp Tyr Ser
1               5

<210> SEQ ID NO 37
<211> LENGTH: 8
<212> TYPE: PRT
<213> ORGANISM: Artificial Sequence
<220> FEATURE:
<223> OTHER INFORMATION: 3G8-VHCDR1

<400> SEQUENCE: 37

Gly Tyr Ser Phe Thr Lys Tyr Gly
1               5

<210> SEQ ID NO 38
<211> LENGTH: 9
<212> TYPE: PRT
<213> ORGANISM: Artificial Sequence
<220> FEATURE:
<223> OTHER INFORMATION: 3F12-VHCDR1

<400> SEQUENCE: 38

Gly Tyr Ser Ile Thr Ser Gly Tyr Ser
1               5

<210> SEQ ID NO 39
<211> LENGTH: 8
<212> TYPE: PRT
<213> ORGANISM: Artificial Sequence
<220> FEATURE:
<223> OTHER INFORMATION: 2A11,4C2,8C4-VHCDR2
<220> FEATURE:
<221> NAME/KEY: VARIANT
<222> LOCATION: (6)..(7)
<223> OTHER INFORMATION: Xaa is Gly or Ala

<400> SEQUENCE: 39

Ile Asp Pro Glu Thr Xaa Xaa Thr
1               5

<210> SEQ ID NO 40
<211> LENGTH: 8
<212> TYPE: PRT
<213> ORGANISM: Artificial Sequence
<220> FEATURE:
<223> OTHER INFORMATION: 3B5-VHCDR2

<400> SEQUENCE: 40

Ile Asp Pro Tyr Asn Gly Gly Asn
1               5

<210> SEQ ID NO 41
<211> LENGTH: 8
<212> TYPE: PRT
<213> ORGANISM: Artificial Sequence
<220> FEATURE:
<223> OTHER INFORMATION: 9B3,9B12,3B5-VHCDR2
<220> FEATURE:
<221> NAME/KEY: VARIANT
<222> LOCATION: (8)..(8)
<223> OTHER INFORMATION: Xaa is Ser or Thr

<400> SEQUENCE: 41

Ile Asn Pro Gly Ser Gly Gly Xaa
1               5
```

```
<210> SEQ ID NO 42
<211> LENGTH: 8
<212> TYPE: PRT
<213> ORGANISM: Artificial Sequence
<220> FEATURE:
<223> OTHER INFORMATION: 10H7-VHCDR2

<400> SEQUENCE: 42

Ile Asn Thr Glu Thr Gly Glu Pro
1               5

<210> SEQ ID NO 43
<211> LENGTH: 8
<212> TYPE: PRT
<213> ORGANISM: Artificial Sequence
<220> FEATURE:
<223> OTHER INFORMATION: 3G8-VHCDR2

<400> SEQUENCE: 43

Ile Asn Thr Asn Thr Gly Glu Ala
1               5

<210> SEQ ID NO 44
<211> LENGTH: 7
<212> TYPE: PRT
<213> ORGANISM: Artificial Sequence
<220> FEATURE:
<223> OTHER INFORMATION: 3F12-VHCDR2

<400> SEQUENCE: 44

Ile Tyr Tyr Arg Gly Ser Thr
1               5

<210> SEQ ID NO 45
<211> LENGTH: 16
<212> TYPE: PRT
<213> ORGANISM: Artificial Sequence
<220> FEATURE:
<223> OTHER INFORMATION: 2A11,4C2,8C4-VHCDR3

<400> SEQUENCE: 45

Thr Arg Gly Lys Phe Tyr Tyr Ser Gly Arg Asp Tyr Ala Met Asp Tyr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: 3B5-VHCDR3

<400> SEQUENCE: 46

Ala Arg Gly Tyr Tyr Arg Tyr Gly Gly Gly Asp Phe Asp Tyr
1               5                   10                  15

<210> SEQ ID NO 47
<211> LENGTH: 12
<212> TYPE: PRT
<213> ORGANISM: Artificial Sequence
<220> FEATURE:
<223> OTHER INFORMATION: 9B3,9B12,3B10-VHCDR3
<220> FEATURE:
<221> NAME/KEY: VARIANT
<222> LOCATION: (12)..(12)
<223> OTHER INFORMATION: Xaa is Tyr or His

<400> SEQUENCE: 47
```

```
Arg Ile Tyr Gly Asn Tyr Lys Gly Tyr Phe Asp Xaa
1               5                   10

<210> SEQ ID NO 48
<211> LENGTH: 14
<212> TYPE: PRT
<213> ORGANISM: Artificial Sequence
<220> FEATURE:
<223> OTHER INFORMATION: 10H7-VHCDR3

<400> SEQUENCE: 48

Ala Arg Phe Asp Tyr Gly Thr Ser Tyr Trp Tyr Phe Asp Val
1               5                   10

<210> SEQ ID NO 49
<211> LENGTH: 10
<212> TYPE: PRT
<213> ORGANISM: Artificial Sequence
<220> FEATURE:
<223> OTHER INFORMATION: 3G8-VHCDR3

<400> SEQUENCE: 49

Ala Arg Leu Gly Leu Arg Tyr Leu Asp Tyr
1               5                   10

<210> SEQ ID NO 50
<211> LENGTH: 5
<212> TYPE: PRT
<213> ORGANISM: Artificial Sequence
<220> FEATURE:
<223> OTHER INFORMATION: 3F12-VHCDR3

<400> SEQUENCE: 50

Ala Arg Glu Ala Tyr
1               5

<210> SEQ ID NO 51
<211> LENGTH: 11
<212> TYPE: PRT
<213> ORGANISM: Artificial Sequence
<220> FEATURE:
<223> OTHER INFORMATION: 2A11,4C2,8C4-VLCDR1

<400> SEQUENCE: 51

Gln Ser Ile Val His Ser Asn Gly Asn Thr Tyr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: 3B5-VLCDR1

<400> SEQUENCE: 52

Gln Ser Leu Val His Ser Asn Gly Asn Thr Tyr
1               5                   10

<210> SEQ ID NO 53
<211> LENGTH: 6
<212> TYPE: PRT
<213> ORGANISM: Artificial Sequence
<220> FEATURE:
<223> OTHER INFORMATION: 9B3,9B12,3B10-VLCDR1
<220> FEATURE:
<221> NAME/KEY: VARIANT
<222> LOCATION: (3)..(3)
```

```
<223> OTHER INFORMATION: Xaa is Ile or Met

<400> SEQUENCE: 53

Gln Asp Xaa Asn Ser Tyr
1               5

<210> SEQ ID NO 54
<211> LENGTH: 6
<212> TYPE: PRT
<213> ORGANISM: Artificial Sequence
<220> FEATURE:
<223> OTHER INFORMATION: 10H7-VLCDR1

<400> SEQUENCE: 54

Gln Ser Ile Ser Ser Tyr
1               5

<210> SEQ ID NO 55
<211> LENGTH: 10
<212> TYPE: PRT
<213> ORGANISM: Artificial Sequence
<220> FEATURE:
<223> OTHER INFORMATION: 3G8-VLCDR1

<400> SEQUENCE: 55

Lys Ser Val Ser Thr Ser Asp Tyr Ser Tyr
1               5                   10

<210> SEQ ID NO 56
<211> LENGTH: 11
<212> TYPE: PRT
<213> ORGANISM: Artificial Sequence
<220> FEATURE:
<223> OTHER INFORMATION: 3F12-VLCDR1

<400> SEQUENCE: 56

Gln Ser Leu Leu Asp Ser Asp Gly Glu Thr Tyr
1               5                   10

<210> SEQ ID NO 57
<211> LENGTH: 3
<212> TYPE: PRT
<213> ORGANISM: Artificial Sequence
<220> FEATURE:
<223> OTHER INFORMATION: 2A11,4C2,8C4-VLCDR2

<400> SEQUENCE: 57

Lys Val Ser
1

<210> SEQ ID NO 58
<211> LENGTH: 3
<212> TYPE: PRT
<213> ORGANISM: Artificial Sequence
<220> FEATURE:
<223> OTHER INFORMATION: 3B5-VLCDR2

<400> SEQUENCE: 58

Lys Val Ser
1

<210> SEQ ID NO 59
<211> LENGTH: 3
<212> TYPE: PRT
<213> ORGANISM: Artificial Sequence
<220> FEATURE:
<223> OTHER INFORMATION: 9B3,9B12,3B10-VLCDR2
```

```
<220> FEATURE:
<221> NAME/KEY: VARIANT
<222> LOCATION: (2)..(2)
<223> OTHER INFORMATION: Xaa is Ala or Ser

<400> SEQUENCE: 59

Arg Xaa Asn
1

<210> SEQ ID NO 60
<211> LENGTH: 3
<212> TYPE: PRT
<213> ORGANISM: Artificial Sequence
<220> FEATURE:
<223> OTHER INFORMATION: 10H7-VLCDR2

<400> SEQUENCE: 60

Ala Ala Ser
1

<210> SEQ ID NO 61
<211> LENGTH: 3
<212> TYPE: PRT
<213> ORGANISM: Artificial Sequence
<220> FEATURE:
<223> OTHER INFORMATION: 3G8-VLCDR2

<400> SEQUENCE: 61

Leu Ala Ser
1

<210> SEQ ID NO 62
<211> LENGTH: 3
<212> TYPE: PRT
<213> ORGANISM: Artificial Sequence
<220> FEATURE:
<223> OTHER INFORMATION: 3F12-VLCDR2

<400> SEQUENCE: 62

Leu Val Ser
1

<210> SEQ ID NO 63
<211> LENGTH: 9
<212> TYPE: PRT
<213> ORGANISM: Artificial Sequence
<220> FEATURE:
<223> OTHER INFORMATION: 2A11,4C2,8C4-VLCDR3

<400> SEQUENCE: 63

Phe Gln Gly Ser Gln Val Pro Pro Thr
1               5

<210> SEQ ID NO 64
<211> LENGTH: 9
<212> TYPE: PRT
<213> ORGANISM: Artificial Sequence
<220> FEATURE:
<223> OTHER INFORMATION: 3B5-VLCDR3

<400> SEQUENCE: 64

Ser Gln Asn Thr His Ile Pro Pro Thr
1               5

<210> SEQ ID NO 65
<211> LENGTH: 9
<212> TYPE: PRT
```

<213> ORGANISM: Artificial Sequence
<220> FEATURE:
<223> OTHER INFORMATION: 9B3,9B12,3B10-VLCDR3

<400> SEQUENCE: 65

Leu Gln Asn Asp Glu Phe Pro Phe Thr
1               5

<210> SEQ ID NO 66
<211> LENGTH: 9
<212> TYPE: PRT
<213> ORGANISM: Artificial Sequence
<220> FEATURE:
<223> OTHER INFORMATION: 10H7-VLCDR3

<400> SEQUENCE: 66

Gln Gln Ser Tyr Thr Thr Pro Leu Thr
1               5

<210> SEQ ID NO 67
<211> LENGTH: 9
<212> TYPE: PRT
<213> ORGANISM: Artificial Sequence
<220> FEATURE:
<223> OTHER INFORMATION: 3G8-VLCDR3

<400> SEQUENCE: 67

Gln His Asn Arg Glu Leu Pro Pro Thr
1               5

<210> SEQ ID NO 68
<211> LENGTH: 9
<212> TYPE: PRT
<213> ORGANISM: Artificial Sequence
<220> FEATURE:
<223> OTHER INFORMATION: 3F12-VLCDR3

<400> SEQUENCE: 68

Trp Gln Gly Thr His Phe Pro Tyr Thr
1               5

<210> SEQ ID NO 69
<211> LENGTH: 211
<212> TYPE: PRT
<213> ORGANISM: Homo sapiens

<400> SEQUENCE: 69

Met Ala Gln Ala Lys Ile Asn Ala Lys Ala Asn Glu Gly Arg Phe Cys
1               5                   10                  15

Arg Ser Ser Met Ala Asp Arg Ser Ser Arg Leu Leu Glu Ser Leu
            20                  25                  30

Asp Gln Leu Glu Leu Arg Val Glu Ala Leu Arg Glu Ala Ala Thr Ala
        35                  40                  45

Val Glu Gln Glu Lys Glu Ile Leu Leu Glu Met Ile His Ser Ile Gln
    50                  55                  60

Asn Ser Gln Asp Met Arg Gln Ile Ser Asp Gly Glu Arg Glu Glu Leu
65                  70                  75                  80

Asn Leu Thr Ala Asn Arg Leu Met Gly Arg Thr Leu Thr Val Glu Val
                85                  90                  95

Ser Val Glu Thr Ile Arg Asn Pro Gln Gln Gln Glu Ser Leu Lys His
            100                 105                 110

Ala Thr Arg Ile Ile Asp Glu Val Val Asn Lys Phe Leu Asp Asp Leu
        115                 120                 125

Gly Asn Ala Lys Ser His Leu Met Ser Leu Tyr Ser Ala Cys Ser Ser
        130                 135                 140

Glu Val Pro His Gly Pro Val Asp Gln Lys Phe Gln Ser Ile Val Ile
145                 150                 155                 160

Gly Cys Ala Leu Glu Asp Gln Lys Lys Ile Lys Arg Arg Leu Glu Thr
                165                 170                 175

Leu Leu Arg Asn Ile Glu Asn Ser Asp Lys Ala Ile Lys Leu Leu Glu
            180                 185                 190

His Ser Lys Gly Ala Gly Ser Lys Thr Leu Gln Gln Asn Ala Glu Ser
        195                 200                 205

Arg Phe Asn
    210

<210> SEQ ID NO 70
<211> LENGTH: 636
<212> TYPE: DNA
<213> ORGANISM: Homo sapiens

<400> SEQUENCE: 70
atggctcagg cgaagatcaa cgctaaagcc aacgagggc gcttctgccg ctcctcctcc      60
atggctgacc gctccagccg cctgctggag agcctggacc agctggagct cagggttgaa     120
gctttgagag aagcagcaac tgctgttgag caagagaaag aaatccttct ggaaatgatc     180
cacagtatcc aaaatagcca ggacatgagg cagatcagtg acggagaaag agaagaatta     240
aatctgactg caaaccgttt gatgggaaga actctcaccg ttgaagtgtc agtagaaaca     300
attagaaacc cccagcagca agaatcccta agcatgcca caaggattat tgatgaggtg      360
gtcaataagt ttctggatga tttgggaaat gccaagagtc atttaatgtc gctctacagt     420
gcatgttcat ctgaggtgcc acatgggcca gttgatcaga gtttcaatc catagtaatt     480 ggctgtgctc ttgaagatca aagaaaatt aagagaagat tagagactct gcttagaaat     540
attgaaaact ctgacaaggc catcaagcta ttagagcatt ctaaaggagc tggttccaaa     600
actctgcaac aaaatgctga agcagattc aattag                               636

<210> SEQ ID NO 71
<211> LENGTH: 270
<212> TYPE: DNA
<213> ORGANISM: Artificial Sequence
<220> FEATURE:
<223> OTHER INFORMATION: GST-Bag F1 vector

<400> SEQUENCE: 71
atggctcagg cgaagatcaa cgctaaagcc aacgagggc gcttctgccg ctcctcctcc      60
atggctgacc gctccagccg cctgctggag agcctggacc agctggagct cagggttgaa     120
gctttgagag aagcagcaac tgctgttgag caagagaaag aaatccttct ggaaatgatc     180
cacagtatcc aaaatagcca ggacatgagg cagatcagtg acggagaaag agaagaatta     240
aatctgactg caaaccgttt gatgggaaga                                      270

<210> SEQ ID NO 72
<211> LENGTH: 360
<212> TYPE: DNA
<213> ORGANISM: Artificial Sequence
<220> FEATURE:
<223> OTHER INFORMATION: GST-Bag F2 vector

<400> SEQUENCE: 72

```
atggctcagg cgaagatcaa cgctaaagcc aacgaggggc gcttctgccg ctcctcctcc        60
atggctgacc gctccagccg cctgctggag agcctggacc agctggagct cagggttgaa       120
gctttgagag aagcagcaac tgctgttgag caagagaaag aaatccttct ggaaatgatc       180
cacagtatcc aaaatagcca ggacatgagg cagatcagtg acggagaaag agaagaatta       240
aatctgactg caaaccgttt gatgggaaga actctcaccg ttgaagtgtc agtagaaaca       300
attagaaacc cccagcagca agaatcccta agcatgcca caaggattat tgatgaggtg        360
```

<210> SEQ ID NO 73
<211> LENGTH: 450
<212> TYPE: DNA
<213> ORGANISM: Artificial Sequence
<220> FEATURE:
<223> OTHER INFORMATION: GST-Bag F3 vector

<400> SEQUENCE: 73

```
atggctcagg cgaagatcaa cgctaaagcc aacgaggggc gcttctgccg ctcctcctcc        60
atggctgacc gctccagccg cctgctggag agcctggacc agctggagct cagggttgaa       120
gctttgagag aagcagcaac tgctgttgag caagagaaag aaatccttct ggaaatgatc       180
cacagtatcc aaaatagcca ggacatgagg cagatcagtg acggagaaag agaagaatta       240
aatctgactg caaaccgttt gatgggaaga actctcaccg ttgaagtgtc agtagaaaca       300
attagaaacc cccagcagca agaatcccta agcatgcca caaggattat tgatgaggtg        360
gtcaataagt ttctggatga tttgggaaat gccaagagtc atttaatgtc gctctacagt       420
gcatgttcat ctgaggtgcc acatgggcca                                        450
```

<210> SEQ ID NO 74
<211> LENGTH: 540
<212> TYPE: DNA
<213> ORGANISM: Artificial Sequence
<220> FEATURE:
<223> OTHER INFORMATION: GST-Bag F4 vector

<400> SEQUENCE: 74

```
atggctcagg cgaagatcaa cgctaaagcc aacgaggggc gcttctgccg ctcctcctcc        60
atggctgacc gctccagccg cctgctggag agcctggacc agctggagct cagggttgaa       120
gctttgagag aagcagcaac tgctgttgag caagagaaag aaatccttct ggaaatgatc       180
cacagtatcc aaaatagcca ggacatgagg cagatcagtg acggagaaag agaagaatta       240
aatctgactg caaaccgttt gatgggaaga actctcaccg ttgaagtgtc agtagaaaca       300
attagaaacc cccagcagca agaatcccta agcatgcca caaggattat tgatgaggtg        360
gtcaataagt ttctggatga tttgggaaat gccaagagtc atttaatgtc gctctacagt       420
gcatgttcat ctgaggtgcc acatgggcca gttgatcaga agtttcaatc catagtaatt       480
ggctgtgctc ttgaagatca gaagaaaatt aagagaagat tagagactct gcttagaaat       540
```

<210> SEQ ID NO 75
<211> LENGTH: 122
<212> TYPE: PRT
<213> ORGANISM: Artificial Sequence
<220> FEATURE:
<223> OTHER INFORMATION: 3B5 subclone 1: VH region

<400> SEQUENCE: 75

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ser Phe Thr Asp Tyr
            20                  25                  30

Thr Phe Tyr Trp Val Arg Gln Ala Pro Gly Gln Arg Leu Glu Trp Ile
        35                  40                  45

Gly Tyr Ile Asp Pro Tyr Asn Ala Gly Asn Thr Tyr Asn Arg Lys Phe
    50                  55                  60

Lys Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Arg Tyr Gly Gly Gly Asp Phe Asp Tyr Trp
            100                 105                 110

Gly Gln Gly Thr Leu Val Thr Val Ser Ser
            115                 120

<210> SEQ ID NO 76
<211> LENGTH: 112
<212> TYPE: PRT
<213> ORGANISM: Artificial Sequence
<220> FEATURE:
<223> OTHER INFORMATION: 3B5 subclone 1: VL region

<400> SEQUENCE: 76

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Ile Pro Pro Thr Phe Gly Gly Gly Thr Lys Val Glu Ile Lys
            100                 105                 110

<210> SEQ ID NO 77
<211> LENGTH: 122
<212> TYPE: PRT
<213> ORGANISM: Artificial Sequence
<220> FEATURE:
<223> OTHER INFORMATION: 3B5 subclone 2: VH region

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Thr Phe Tyr Trp Val Arg Gln Ala Pro Gly Gln Arg Leu Glu Trp Ile
        35                  40                  45

Gly Tyr Ile Asp Pro Tyr Asn Ala Gly Asn Thr Tyr Asn Arg Lys Phe
    50                  55                  60

Lys Gly Lys Val Thr Ile Thr Val Asp Lys Ser Ala Ser Thr Ala Tyr
65                  70                  75                  80

Met Glu Leu Asn Ser Leu Arg Ser Glu Asp Thr Ala Val Tyr Tyr Cys
                85                  90                  95
```

```
Ala Arg Gly Tyr Tyr Arg Tyr Gly Gly Gly Asp Phe Asp Tyr Trp
            100                 105                 110

Gly Gln Gly Thr Leu Val Thr Val Ser Ser
            115                 120
```

<210> SEQ ID NO 78
<211> LENGTH: 112
<212> TYPE: PRT
<213> ORGANISM: Artificial Sequence
<220> FEATURE:
<223> OTHER INFORMATION: 3B5 subclone 2: VL region

<400> SEQUENCE: 78

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Ile Pro Pro Thr Phe Gly Gly Gly Thr Lys Val Glu Ile Lys
            100                 105                 110
```

<210> SEQ ID NO 79
<211> LENGTH: 119
<212> TYPE: PRT
<213> ORGANISM: Artificial Sequence
<220> FEATURE:
<223> OTHER INFORMATION: 3B10 subclone 1: VH region

<400> SEQUENCE: 79

```
Gln Val Gln Leu Val Gln Ser Gly Ala Glu Val Lys Lys Pro Gly Ala
1               5                   10                  15

Ser Val Lys Val Ser Cys Lys Ala Ser Gly His Ala Phe Thr Asn Tyr
            20                  25                  30

Met Ile Glu Trp Val Arg Gln Ala Pro Gly Gln Gly Leu Glu Trp Met
        35                  40                  45

Gly Val Ile Asn Pro Gly Ser Gly Gly Thr Tyr Asn Ser Glu Lys Val
    50                  55                  60

Lys Gly Arg Val Thr Leu Thr Ala Asp Arg Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Arg Ile Tyr Gly Asn Tyr Lys Gly Tyr Phe Asp His Trp Gly Gln Gly
            100                 105                 110

Thr Leu Val Thr Val Ser Ser
        115
```

<210> SEQ ID NO 80
<211> LENGTH: 107
<212> TYPE: PRT
<213> ORGANISM: Artificial Sequence
<220> FEATURE:
<223> OTHER INFORMATION: 3B10 subclone 1: VL region

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Met Asn Ser Tyr
            20                  25                  30

Leu Ser Trp Phe Gln Gln Lys Pro Gly Lys Ala Pro Lys Ser Leu Ile
        35                  40                  45

Tyr Arg Ser Asn Arg Leu Val Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Asp Glu Phe Pro Phe
                85                  90                  95

Thr Phe Gly Gln Gly Thr Lys Leu Glu Ile Lys
            100                 105

<210> SEQ ID NO 81
<211> LENGTH: 117
<212> TYPE: PRT
<213> ORGANISM: Artificial Sequence
<220> FEATURE:
<223> OTHER INFORMATION: 3B10 subclone 2: VH region

<400> SEQUENCE: 81

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Lys Tyr
            20                  25                  30

Gly Met Asn Trp Val Lys Gln Ala Pro Gly Gln Gly Leu Glu Trp Met
        35                  40                  45

Gly Trp Ile Asn Thr Asn Thr Gly Glu Ala Thr Tyr Gly Glu Glu Val
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Leu Gly Leu Arg Tyr Leu Asp Tyr Trp Gly Gln Gly Thr Leu
            100                 105                 110

Val Thr Val Ser Ser
        115

<210> SEQ ID NO 82
<211> LENGTH: 110
<212> TYPE: PRT
<213> ORGANISM: Artificial Sequence
<220> FEATURE:
<223> OTHER INFORMATION: 3B10 subclone 2: VL region

<400> SEQUENCE: 82

Ile Gln Met Thr Gln Ser Pro Ser Ser Leu Ser Ala Ser Val Gly Asp
1               5                   10                  15

Arg Val Thr Ile Thr Cys Arg Ala Ser Lys Ser Val Thr Ser Asp
            20                  25                  30

Tyr Ser Tyr Met His Trp Tyr Gln Gln Lys Pro Gly Lys Ala Pro Lys
        35                  40                  45

Leu Leu Ile Tyr Leu Ala Ser Asn Leu Glu Ser Gly Val Pro Ser Arg
50                  55                  60

```
Phe Ser Gly Ser Gly Ser Gly Thr Asp Phe Thr Leu Thr Ile Ser Ser
 65                  70                  75                  80

Leu Gln Pro Glu Asp Phe Ala Thr Tyr Tyr Cys Gln His Asn Arg Glu
                 85                  90                  95

Leu Pro Pro Thr Phe Gly Gln Gly Thr Lys Leu Glu Ile Lys
            100                 105                 110

<210> SEQ ID NO 83
<211> LENGTH: 117
<212> TYPE: PRT
<213> ORGANISM: Artificial Sequence
<220> FEATURE:
<223> OTHER INFORMATION: 3G8 subclone 1: VH region

<400> SEQUENCE: 83

Gln Val Gln Leu Val Gln Ser Gly Ser Glu Leu Lys Lys Pro Gly Ala
  1               5                  10                  15

Ser Val Lys Val Ser Cys Lys Ala Ser Gly Tyr Ser Phe Thr Lys Tyr
                 20                  25                  30

Gly Met Asn Trp Val Arg Gln Ala Pro Gly Gln Gly Leu Glu Trp Met
             35                  40                  45

Gly Trp Ile Asn Thr Asn Thr Gly Glu Ala Thr Tyr Gly Glu Glu Val
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Leu Gly Leu Arg Tyr Leu Asp Tyr Trp Gly Gln Gly Thr Leu
            100                 105                 110

Val Thr Val Ser Ser
            115

<210> SEQ ID NO 84
<211> LENGTH: 111
<212> TYPE: PRT
<213> ORGANISM: Artificial Sequence
<220> FEATURE:
<223> OTHER INFORMATION: 3G8 subclone 1: VL region

<400> SEQUENCE: 84

Asp Ile Gln Met Thr Gln Ser Pro Ser Ser Leu Ser Ala Ser Val Gly
  1               5                  10                  15

Asp Arg Val Thr Ile Thr Cys Arg Ala Ser Lys Ser Val Ser Thr Ser
                 20                  25                  30

Asp Tyr Ser Tyr Met His Trp Tyr Gln Gln Lys Pro Gly Lys Ala Pro
             35                  40                  45

Lys Leu Leu Ile Tyr Leu Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Asn Arg
                 85                  90                  95

Glu Leu Pro Pro Thr Phe Gly Gln Gly Thr Lys Leu Glu Ile Lys
            100                 105                 110

<210> SEQ ID NO 85
<211> LENGTH: 117
<212> TYPE: PRT
```

```
<213> ORGANISM: Artificial Sequence
<220> FEATURE:
<223> OTHER INFORMATION: 3G8 subclone 2: VH region

<400> SEQUENCE: 85

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Lys Tyr
                20                  25                  30

Gly Met Asn Trp Val Lys Gln Ala Pro Gly Gln Gly Leu Glu Trp Met
            35                  40                  45

Gly Trp Ile Asn Thr Asn Thr Gly Glu Ala Thr Tyr Gly Glu Glu Val
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Leu Gly Leu Arg Tyr Leu Asp Tyr Trp Gly Gln Gly Thr Leu
            100                 105                 110

Val Thr Val Ser Ser
            115

<210> SEQ ID NO 86
<211> LENGTH: 111
<212> TYPE: PRT
<213> ORGANISM: Artificial Sequence
<220> FEATURE:
<223> OTHER INFORMATION: 3G8 subclone 2: VL region

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
                20                  25                  30

Asp Tyr Ser Tyr Met His Trp Tyr Gln Gln Lys Pro Gly Lys Ala Pro
            35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Asn Arg
                85                  90                  95

Glu Leu Pro Pro Thr Phe Gly Gln Gly Thr Lys Leu Glu Ile Lys
            100                 105                 110
```